US008497355B2

(12) United States Patent
Igawa et al.

(10) Patent No.: US 8,497,355 B2
(45) Date of Patent: Jul. 30, 2013

(54) ANTI-GLYPICAN-3 ANTIBODY HAVING IMPROVED KINETICS IN PLASMA

(75) Inventors: Tomoyuki Igawa, Shizuoka (JP); Taichi Kuramochi, Shizuoka (JP); Hirotake Shiraiwa, Shizuoka (JP); Hiroyuki Tsunoda, Shizuoka (JP); Tatsuhiko Tachibana, Shizuoka (JP); Takahiro Ishiguro, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 301 days.

(21) Appl. No.: 12/733,933

(22) PCT Filed: Sep. 26, 2008

(86) PCT No.: PCT/JP2008/002690

§ 371 (c)(1),
(2), (4) Date: Jun. 3, 2010

(87) PCT Pub. No.: WO2009/041062

PCT Pub. Date: Apr. 2, 2009

(65) Prior Publication Data

US 2010/0239577 A1 Sep. 23, 2010

(30) Foreign Application Priority Data

Sep. 28, 2007 (JP) ................................ 2007-256063

(51) Int. Cl.

| | |
|---|---|
| ***C07K 16/30*** | (2006.01) |
| ***A61K 39/395*** | (2006.01) |
| ***C07H 21/04*** | (2006.01) |
| ***C12P 21/08*** | (2006.01) |
| ***C12N 15/13*** | (2006.01) |

(52) U.S. Cl.

USPC ................ 530/388.85; 530/387.3; 530/388.8; 424/133.1; 424/155.1; 424/156.1; 536/23.53; 435/69.1; 435/70.1; 435/328; 435/330

(58) Field of Classification Search

USPC ............... 424/130.1–177.1; 530/387.1–391.9
See application file for complete search history.

(56) References Cited

U.S. PATENT DOCUMENTS

| | | | |
|---|---|---|---|
| 7,797,974 | B2 | 9/2010 | Krüger et al. |
| 2005/0032759 | A1 | 2/2005 | Massimini et al. |
| 2006/0088899 | A1 | 4/2006 | Alvarez et al. |
| 2007/0087005 | A1 | 4/2007 | Lazar et al. |
| 2007/0185069 | A1 | 8/2007 | Plum et al. |
| 2007/0190599 | A1 | 8/2007 | Nakano et al. |
| 2008/0124330 | A1 | 5/2008 | Nakano et al. |
| 2008/0166756 | A1 | 7/2008 | Tsuchiya et al. |
| 2009/0263392 | A1 | 10/2009 | Igawa et al. |
| 2009/0324589 | A1 | 12/2009 | Igawa et al. |
| 2011/0002922 | A1 | 1/2011 | Aburatani et al. |
| 2011/0104157 | A1 | 5/2011 | Kinoshita et al. |

FOREIGN PATENT DOCUMENTS

| | | | |
|---|---|---|---|
| CN | 1688692 | A | 10/2005 |
| CN | 1842540 | A | 10/2006 |
| CN | 101068836 | A | 11/2007 |
| EP | 125023 | | 4/1984 |
| EP | 239400 | | 8/1994 |
| EP | 1411118 | A1 | 4/2004 |
| EP | 1800693 | A1 | 6/2007 |
| EP | 1816140 | | 8/2007 |
| EP | 1829962 | | 9/2007 |
| EP | 1982718 | | 10/2008 |
| JP | 1-59878 | | 12/1989 |
| JP | 02-028200 | | 1/1990 |
| JP | 2004-503582 | | 2/2004 |
| JP | 2008-501677 | | 1/2008 |
| JP | 2008-504970 | | 2/2008 |
| WO | WO 92/01047 | | 1/1992 |
| WO | WO 92/03918 | | 3/1992 |
| WO | WO 92/20791 | | 11/1992 |
| WO | WO 93/06213 | | 4/1993 |
| WO | WO 93/11236 | | 6/1993 |
| WO | WO 93/12227 | | 6/1993 |
| WO | WO 93/19172 | | 9/1993 |
| WO | WO 94/02602 | | 2/1994 |
| WO | WO 95/01438 | | 1/1995 |
| WO | WO 95/15388 | | 6/1995 |
| WO | WO 95/15393 | | 6/1995 |

(Continued)

OTHER PUBLICATIONS

Ishiguro et al., Cancer Res. 2008; 23:9832-38.*
Strom et al., The Oncologist, 2007; 12:1084-95.*
Brand et al., Anticancer Res. 2006; 26:463-70.*
International Search Report issued in connection with corresponding International Application No. PCT/JP2008/002690, Dec. 15, 2008.
English Abstract of European Patent EP 0329185 which corresponds to JP 2028200, Jan. 30, 1990.
Extended European Search report issued in corresponding EP Application No. 08834671.3, dated Sep. 9, 2010.

(Continued)

*Primary Examiner* — Sheela J Huff
*Assistant Examiner* — Jessica H Roark
(74) *Attorney, Agent, or Firm* — Davidson, Davidson & Kappel, LLC

(57) ABSTRACT

A method of modulating the plasma half-life of anti-glypican 3 antibody, a pharmaceutical composition comprising as an active ingredient the anti-glypican 3 antibody that has a plasma half-life that has been modulated, a method of preparing the anti-glypican 3 antibody and a pharmaceutical composition comprising the anti-glypican 3 antibody as an active ingredient are provided. Disclosed is a method of modulating the plasma half-life of anti-glypican 3 antibody by modifying an amino acid residue that is exposed on the surface of the anti-glypican 3 antibody; and anti-glypican 3 antibody that has a plasma half-life that has been modulated by amino acid residue modification, a pharmaceutical composition comprising as an active ingredient the anti-glypican 3 antibody, and a method of preparing the anti-glypican 3 antibody and producing a pharmaceutical composition comprising the anti-glypican 3 antibody as an active ingredient.

16 Claims, 9 Drawing Sheets

FOREIGN PATENT DOCUMENTS

| | | | |
|---|---|---|---|
| WO | WO 96/02576 | | 2/1996 |
| WO | WO 96/33735 | | 10/1996 |
| WO | WO 96/34096 | | 10/1996 |
| WO | WO 98/13388 | | 4/1998 |
| WO | WO 98/46777 | | 10/1998 |
| WO | WO 99/18212 | | 4/1999 |
| WO | WO 02/05791 | | 1/2002 |
| WO | WO 03/000883 | | 1/2003 |
| WO | WO 2004/035752 | | 4/2004 |
| WO | WO 2005/117980 | | 12/2005 |
| WO | WO 2006/006693 | | 1/2006 |
| WO | 2006/046751 | | 5/2006 |
| WO | 2006/067913 | | 6/2006 |
| WO | WO 2006/067913 | | 6/2006 |
| WO | 2007/005612 | | 1/2007 |
| WO | WO 2007/053573 | | 5/2007 |
| WO | WO 2007/091622 | | 8/2007 |
| WO | WO 2007/099988 | | 9/2007 |
| WO | WO 2007/114319 | | 10/2007 |
| WO | WO 2007/114325 | | 10/2007 |
| WO | WO 2007/137170 | A2 | 11/2007 |

OTHER PUBLICATIONS

Gangopadhyay, A., et al. "Modification of Antibody Isoelectric Point Affects Biodistribution of 111-Indium-Labeled Antibody", Nuclear Medicine and Biology, Elsevier, NY, US, vol. 23, No. 3, Apr. 1, 1996, pp. 257-261.
Khwali, L.A., et al. "Improved Tumor Localization and Radioimaging with Chemically Modified Monoclonal Antibodies", Cancer Biotherapy and Radiopharmaceuticals, Liebert, US, vol. 11, No. 3, Jun. 1, 1996, pp. 203-215.
Onda, M., et al. "Lowering the Isoelectric Point of the Fv Portion of Recombinant Immunotoxins Leads to Decreased Nonspecific Animal Toxicity without Affecting Antitumor Activity", Cancer Research, American Association for Cancer Research, US. vol. 61, No. 13, Jul. 1, 2001, pp. 5070-5077.
Zhu A, et al., "Efficacy, safety, and changes in angiogenic markers following sunitinib monotherapy in patients with advanced hepatocellular carcinoma: Experience from a phase II study" 99thAACR annual meeting. San Diego, CA, USA Apr. 12-16, 2008.
Llovet, J.M, et al., "Hepatocellular carcinoma", Lancet, vol. 362, 1907-17 (2003).
Bosch, FX, et al., "Primary Liver Cancer: Worldwide Incidence and Trends" Gastroenterology 127. S5-16 (2004).
Takenaka, K., et al., "Results of 280 Liver Resections for Hepatocellular Carcinoma", Arch Surg 131, 71-6 (1996).
Yeo, W, et al., "Randomized Phase III Study of Doxorubicin Versus Cisplatin/Interferon α-2b/Doxorubicin/Fluorouracil (PIAF) Combination Chemotherapy for Unresectable Hepatocellular Carcinoma", J Natl. Cancer Inst. 97, 1532-8 (2005).
Furuse, J., et al., "Phase I study of sorafenib in Japanese patients with hepatocellular carcinoma", Cancer Sci., Oct. 22 (E-Pub), 159-165 (2007).
Philip, P.A., et al, "Phase II Study of Erlotinib (OSI-774) in Patients with Advanced Hepatocellular Cancer", J. Clin. Oncol. vol. 23, No. 7, pp. 6657-6663 (2005).
Thomas, M.B., et al., "A Phase II Open-label Study of OSI-774 (NSC 718781) in Unresectable Hepatocellular Carcinoma", J. Clin. On. 2005 ASCO Annual Meeting Proceedings, 23, 16S (2005).
Mendel DB, et al., "In Vivo Antitumor Activity of SU11248, a Novel Tyrosine Kinase Inhibitor Targeting vascular Endothelial Growth Factor and Platelet-derived Growth Factor Receptors: Determination of a Pharmacokinetic/Pharmacodynamic Relationship", Clin Cancer Res (2003), 9, 327-37.
Masafumi Ikeda et al., "Drug Therapy for Primary Liver Cancer and Kinase Inhibitor Sorafenib", Hematology & Oncology, Jan. 28, 2008, vol. 56, No. 1, pp. 70 to 75, Issn: 0915-8529 (with English translation).
International Search Report and Written Opinion issued in corresponding PCT/JP2009/001249, Mar. 19, 2009.
Reichert, Janice M et al., "Monoclonal antibody successes in the clinic", Nature Biotechnology (2005) 23, 1073-8.
Reichert, Janice M and Valge-Archer, Viia E., "Development trends for monoclonal antibody cancer therapeutics", Nat. Rev. Drug Disc. (2007) 6, 349-356.
Nesterova, Albina et al., "Glypican-3 as a Novel Target for an Antibody-Drug Conjugate"., AACR Abstract No. 656 (2007), Los Angeles, CA Apr. 14-18 (Abstract).
Kim SJ, et al., "Antibody engineering for the development of therapeutic antibodies"., Mol Cells. (2005) 20(1), 17-29.
Hinton PR, et al., An engineered human IgG1 antibody with longer serum half-life., J Immunol. (2006) 176(1), 346-56.
Ghetie V, et al., "Increasing the serum persistence of an IgG fragment by random mutagenesis"., Nat Biotechnol. (1997) 15(7), 637-40.
Zuckier LS, et al., "Chimeric human-mouse IgG antibodies with shuffled constant region exons demonstrate that multiple domains contribute to in vivo half-life", Cancer Res. (1998) 58(17), 3905-8.
Lobo, Evelyn D, et al., "Antibody pharmacokinetics and pharmacodynamics", J Pharm Sci. (2004) 93(11),2645-68.
Yamasaki, Yasuomi, et al., "Pharmacokinetic analysis of in vivo disposition of succinylated proteins targeted to liver nonparenchymal cells via scavenger receptors: Importance of molecular size and negative charge density for in vivo recognition by receptors", Pharmacol Exp Ther. (2002) 301(2),467-77.
Poduslo, Joseph F. and Curran, Geoffrey L., "Polyamine modification increases the permeability of proteins at the blood-nerve and blood-brain barriers", Neurochem. (1996) 66(4), 1599-609.
Ghetie, Victor and Ward, E. Sally., "FcRn: the MHC class I-related receptor that is more than an IgG transporter" Immunol Today. (1997) 18(12),592-8.
He, Xing-Yue, et al., "Humanization and pharmacokinetics of a monoclonal antibody with specificity for both E- and P-selectin" J Immunol. (1998) ,160(2) , 1029-35.
Katayose, Yu, et al., "MUCI-specific targeting immunotherapy with bispecific antibodies: inhibition of xenografted human bile duct carcinoma growth" Cancer Res. (1996) 56(18), 4205-12.
Binz H. Kaspar, et al., "Engineering novel binding proteins from nonimmunoglobulin domains", Nat Biotechnol. (2005) 23(10), 1257-68.
Gobburu, Jogarao V.S., et al., "Pharmacokinetics/dynamics of 5c8, a monoclonal antibody to CD154 (CD40 Ligand) suppression of an immune response in monkeys", J Pharmacol Exp Ther. (1998) 286(2),925-30.
Kashmiri, S.V.S., et al, "Generation, characterization, and in vivo studies of humanized anticarcinoma antibody CC49", Hybridoma. (1995) 14(5), 461-73.
Graves, Scott S., et al., "Molecular modeling and preclinical evaluation of the humanized NR-LU-13 antibody", Clin Cancer Res. (1999) 5(4),899-908.
Rajpal, Arvind, et al., "A general method for greatly improving the affinity of antibodies by using combinatorial libraries", Proc Natl Acad Sci USA. (2005) 102(24), 8466-71.
Ewert, Stefan, et al, "Stability improvement of antibodies for extracellular and intracellular applications: CDR grafting to stable frameworks and structure-based framework engineering", Methods. (2004) 34(2), 184-99.
Couto, Joseph R, et al., "Anti-BA46 monoclonal antibody Mc3: humanization using a novel positional consensus and in vivo and in vitro characterization", Cancer Res. (1995) 55(8), 1717-22.
Ono, Koichiro, et al., "The humanized anti-HM1.24 antibody effectively kills multiple myeloma cells by human effector cell-mediated cytotoxicity", Mol Immunol. (1999) 36(6), 387-395.
Vaisitti T, et al., "Cationization of monoclonal antibodies: Another step towards the "magic bullet"?" J Biol Regul Homeost Agents. (2005) 19(3-4), 105-12.
Pardridge, William M, et al., "Enhanced endocytosis in cultured human breast carcinoma cells and in vivo biodistribution in rats of a humanized monoclonal antibody after cationization of the protein" J Pharmacol Exp Ther. (1998) 286(1), 548-54.
Ober, Raimund J, et al., "Differences in promiscuity for antibody-FcRn interactions across species: implications for therapeutic antibodies" Int Immunol. (2001) 13(12), 1551-9.
Harlow, Ed and Lane, David, "Cell Staining", Cold Spring Harbor laboratory, (1988), 359-420.
Cell Quest Software User's Guide (BD Biosciences)(1994)173-174.

Kabat et al., Sequences of Proteins of Immunological Interest (1987), National Institute of Health, Bethesda, Md. Publ. No. 91-3242 (1991), p. 103 & 310.
Chothia, Cyrus et al., "Conformations of immunoglobulin hypervariable regions", Nature (1989) 342, 877-883.
Sato, Koh et al., "Reshaping a human antibody to inhibit the interleukin 6-dependent tumor cell growth", Cancer Res. (1993) 53, 851-6.
Amit, A.G., et al., "Three-dimensional structure of an antigen-antibody complex at 2.8 a resolution", Science (1986) 233, 747-53.
Chothia, Cyrus and Lesk, Arthur M., "Canonical structures for the hypervariable regions of immunoglobulins", J. Mol. Bio. (1987) 196, 901-17.
Abhinandan, K. R. and Martin, Andrew C. R., "Analyzing the "Degree of humanness" of antibody sequences", J. Mol. Bio (2007) 369, 852-862.
Clackson, Tim, et al., "Making antibody fragments using phage display libraries", Nature (1991) 352,624-8.
Marks, James D., et al., "By-passing immunization human antibodies from V-gene libraries displayed on phage", J. Mol. Biol. (1991) 222,581-97.
Waterhouse, Peter, et al., "Combinatorial infection and in vivo recombination: a strategy for making large phage antibody repertoires", Nucleic Acids Res. (1993) 21, 2265-6.
Griffiths, Andrew D., et al., "Isolation of high affinity human antibodies directly from large synthetic repertoires", EMBO J. (1994) 13,3245-60.
Vaughan, Tristan J. et al., "Human antibodies with sub-nanomolar affinities isolated from a large non-immunized phage display library", Nature Biotechnology (1996) 14,309-14.
Current Protocols in Immunology, Chapter 7, Immunologic studies in humans. Editor, John E. Coligan et al., John Wiley & Sons, Inc., (1993).
Kunkel, Thomas A., "Rapid and efficient site-specific mutagenesis without phenotypic selection", Proc. Natl. Acad. Sci. USA, Genetics, (1985) 82, 488-492.
Susumu, Maeda, et al., "Production of human α-interferon in silkworm using a baculovirus vector", Nature (1985) 315,592-4.
Ebert, Karl M., et al., "Induction of human tissue plasminogen activator in the mammary gland of transgenic goats", Bio/Technology (1994) 12,699-702.
Valle, Giorgio, et al., "Synthesis and secretion of mouse immunoglobulin chains from Xenopus oocytes", Nature (1981) 291, 338-340).
Puck, Theodore T., et al., "Genetics of somatic mammalian cells", J. Exp. Med. (1958) 108,945-59.
Current Protocols in Molecular Biology, Chapter 9 Introduction of DNA into Mammalian Cells edited by Ausubel et al. (1987) John Wiley & Sons, sections 9.1-9.9.
Current Protocols in Molecular Biology, Chapter 11 Immunology edited by Ausubel et al. (1987) Publish. John Wiley & Sons, sections 11.4-11.11.
Huijuan, Li, et al., "Optimization of humanized IgGs in glycoengineered Pichia pastoris", Nature Biotechnology (2006) 24, 210-5.
Yutaka, Takebe, et al., "Srα promoter: an efficient and versatile mammalian cDNA expression system composed of the simian virus 40 early promoter and the R-U5 segment of human T-cell leukemia virus type 1 long terminal repeat", Mol. Cell Biol. (1988) 8, 466-472.
Cox, Kevin M., et al., "Glycan optimization of a human monoclonal antibody in the aquatic plant Lemna minor", Nature Biotechnology (2006) 24, 1591-7.
Ferrara, Claudia et al., "Modulation of therapeutic antibody effector functions by glycosylation engineering: Influence of golgi enzyme localization domain and co-expression of heterologous β1, 4-*N*-acetylglucosaminyltransferase IIII and Golgi α-mannosidase", Biotechnol. Bioeng. (2006) 93(5),851-61.
Ma, Julian K-C., et al., "Assembly of monoclonal antibodies with IgG1 and IgA heavy chain domains in transgenic tobacco plants", Eur. J. Immunol. (1994) 24, 131-8.
Ghirlando, Rodolfo et al., "Glycosylation of human IgG-Fc: influences on structure revealed by differential scanning micro-calorimetry", Immunology Letters (1999), 47-52.
Boer, Poppo H., et al., Polymorphisms in the coding and noncoding regions of murine Biochemical Genetics (1990) 28,299-308.
Weitzhandler, Michael et al., "Analysis of carbohydrates on IgG Preparations", Journal of Pharmaceutical Sciences (1994) 83(12), 1670-5.
Schenk, Barbara et al., "MPDU1 mutations underlie a novel human congenital disorder of glycosylation, designated type If", The Journal of Clinical Investigation (2001), 108(11), 1687-95.
Bigge, J. C. et al., "Nonselective and efficient fluorescent labeling of glycans using 2-amino benzamide and anthranilic acid", Analytical Biochemistry (1995) 230(2), 229-238.
Tsurushita, Naoya, et al., "Design of humanized antibodies: from anti- Tac to Zenapax", Methods. (2005) 36(1), 69-83.
Galfre, G. and Milstein, C., "Preparation of monoclonal antibodies: Strategies and procedures", Methods Enzymol. (1981) 73, 3-46.
Pavlou Alex K and Belsey, Mark J., "The therapeutic antibodies market to 2008", Eur J Pharm Biopharm. (2005) 59(3), 389-96.
Hwang, William Ying Khee, et al., "Use of human germline genes in a CDR homology-based approach to antibody humanization", Methods (2005) 36, 35-42.
Adams, Camellia W, et al., "Humanization of a recombinant monoclonal antibody to produce a therapeutic HER dimerization inhibitor, pertuzumab", Cancer Immunol Immunother. (2006) 55(6), 717-27.
Pharmacokinetics Analysis by Practice, (Nanzando )pp. 7-8, 53-58, 85-96 (2003) together with partial English translation (pp. 7-8 and 54-55).
Dall'Acqua, William F., et al., "Antibody humanization by framework shuffling", Methods. (2005) 36(1), 43-60.
Goding, Monoclonal Antibodies: Principles and Practice, Chapter 3.2.1 Production of Monoclonal Antibodies to Purification, Fragmentation and Isotopic Labelling of Monoclonal Antibodies to Chapter 4.2.3, Academic Press (1986) 59-103.
Yamane-Ohnuki, Naoko, et al., "Establishment of *FUT8* knockout Chinese hamster ovary cells: An ideal host cell line for producing completely defucosylated antibodies with enhanced antibody-dependent cellular cytotoxicity", Biotechnol. Bioeng. (2004) 87(5), 614-22.
Yagi, Takeshi, et al., "Homologous recombination at c-*fyn* locus of mouse embryonic stem cells with use of diphtheria toxin A-fragment gene in negative selection", Proc. Natl. Acad. Sci. USA, Genetics, (1990) 87, 9918-22.
Mendez, MJ, et a., "Functional transplant of megabase human immunoglobulin loci recapitulates human antibody response in mice", Nat. Genet. (1997) 15, 146-56 (Abstract).
Office Action dated Oct. 19, 2012, issued by the Ukrainian Patent Office in connection with corresponding Ukrainian Patent Application No. a201013035/M.
Chinese Office Action, issued on Aug. 24, 2012, for corresponding Chinese Application No. 200980119069.3.
Allison Gandy, "Sorafenib New First-Line Option for Advanced Liver Cancer," 2007, http://www.medscape.com/viewarticle/558023, Jun. 11, 2007.

Richard A. Lake et al. "Immunotherapy and Chemotherapy—a Practical Partnership," Nature Reviews|Cancer; vol. 5; 2005, pp. 397-405.
Khaldoun Almhanna et al. "Treatment Approaches for Hepatocellular Carcinoma," Clinical Medicine: Oncology; 2007, pp. 11-19, vol 1.
Anke Wichert et al. "Glypican-3 is Involved in Cellular Protection Against Mitoxantrone in Gastric Carcinoma Cells," Oncogene, vol. 23, 2004, pp. 945-955.
Tetsuya Nakatsura et al. "Glypican-3, Overexpressed Specifically in Human Hepatocellular Carcinoma, is a Novel Tumor Marker," Biochemical and Biophysical Research Communications, vol. 306, 2003, pp. 16-25.
Extended European Search Report dated Feb. 4, 2013, issued by the European Patent Office in connection with corresponding European Patent Application No. 09727052.4.
Office Action, issued on Mar. 18, 2013, for corresponding Russian Patent Application No. 2010145177.
Office Action, issued on Mar. 21, 2013, for corresponding Peruvian Patent Application No. 413-2009.
Queen, C., et al., "A Humanized Antibody that Binds to the Interleukin 2 Receptor," Proc. Natl. Acad. Sci. USA vol. 86, pp. 10029-10033, Dec., 1989.

* cited by examiner

A

B

ANTI-GLYPICAN-3 ANTIBODY HAVING IMPROVED KINETICS IN PLASMA

RELATED APPLICATIONS

This application is a U.S. national phase application of PCT/JP2008/002690, filed on Sep. 26, 2008 which claims priority of Japanese Patent Application No. 2007-256063. filed on Sep. 28, 2007, the disclosures of which are herein incorporated by reference.

BACKGROUND OF THE INVENTION

1. Field of the Invention

The present invention relates to a method of improving the plasma (blood) kinetics of anti-glypican 3 antibodies, a pharmaceutical composition comprising an anti-glypican 3 antibody that has improved plasma kinetics as an active ingredient, and a method of preparing the same.

2. Description of the Related Art

Antibodies are stable in the plasma and exhibit few side effects and for these reasons their use as drugs has been receiving attention. Among the several antibody isotypes, a large number of IgG isotype therapeutic antibodies are on the market and a large number of therapeutic antibodies are also currently under development (Janice M. Reichert, Clark J. Rosensweig, Laura B. Faden, and Matthew C. Dewitz, Monoclonal antibody successes in the clinic, *Nature Biotechnology* (2005) 23, 1073-8; Pavlou A. K. and Belsey M. J., The therapeutic antibodies market to 2008; *Eur. J. Pharm. Biopharm.* (2005) 59(3), 389-96; and Janice M. Reichert and Viia E. Valge-Archer, Development trends for monoclonal antibody cancer therapeutics, *Nat. Rev. Drug Disc.* (2007) 6, 349-356). Anti-glypican 3 antibodies are known to exhibit antitumor activity by exercising cytotoxicity against, for example, liver cancer cells and lung cancer cells (WO 2003/000883). Antibody-drug conjugates comprising an anti-glypican 3 antibody attached to a cytotoxic substance are also known to exhibit antitumor activity against liver cancer, ovarian cancer, melanoma, and so forth (Albina Nesterova, Paul J. Carter, and Leia M. Smith, Glypican 3 as a Novel Target for an Antibody-Drug Conjugate, AACR Abstract No. 656 (2007), Los Angeles, Calif., April, 4-18).

In addition, technologies to enhance the effector functions are being developed for producing second-generation therapeutic antibodies. For example, it is known that the antibody-dependent cellular cytotoxicity (ADCC) activity and the complement-dependent cytotoxicity (CDC) activity are enhanced by an amino acid substitution in which the amino acids constituting the Fc region of IgG isotype antibodies (referred to as IgG antibodies) are replaced by different amino acids (Kim S. J., Park Y., and Hong H. J., Antibody engineering for the development of therapeutic antibodies, *Mol. Cells* (2005) 20(1), 17-29). When an anti-glypican 3 antibody is produced in fucose transporter-deleted CHO cells, fucose is not attached to the branched sugar chains attached to the anti-glypican 3 antibody. Such an anti-glypican 3 antibody has a significantly higher ADCC activity than the anti-glypican 3 antibody that contains fucose in the branched-chain of the sugar chain, and is thought to exhibit a greater antitumor activity as a therapeutic antibody (WO 2006/067913).

In addition to such technologies for enhancing the effector functions, other technologies are also known in which the plasma half-life of an antibody is increased or decreased by amino acid substitution on the amino acids constituting the Fc region of the antibody (Hinton P. R., Xiong J. M., Johlfs M. G., Tang M. T., Keller S., and Tsurushita N., An engineered human IgG1 antibody with longer serum half-life, *J. Immunol. (*2006) 176(1), 346-56; and Ghetie V., Popov S., Borvak J., Radu C., Matesoi D., Medesan C., Ober R. J., and Ward E. S., Increasing the serum persistence of an IgG fragment by random mutagenesis, *Nat. Biotechnol.* (1997) 15(7), 637-40). If a technology that prolongs the plasma half-life of antibodies is applied to therapeutic antibodies, it is expected that the dose of the administered therapeutic antibody is reduced and its interval of administration is extended, which will enable the provision of less expensive therapeutic antibodies with a high convenience factor.

In specific terms, the plasma half-life can be extended by substituting an amino acid of the Fc region of an IgG antibody with another amino acid resulting in improving the IgG antibody's affinity for the neonatal Fc receptor, which is known to be a salvage receptor for the IgG antibody. In addition, it is also known that the plasma half-life is increased by shuffling the individual domains (CH1, CH2, CH3) constituting the constant region of the antibody (Zuckier L. S., Chang C. J., Scharff M. D., and Morrison S. L., Chimeric human-mouse IgG antibodies with shuffled constant region exons demonstrate that multiple domains contribute to in vivo half-life, *Cancer Res.* (1998) 58(17), 3905-8). However, since the amino acid sequence of the constant region of the IgG antibody is conserved in humans, an antibody having an artificial amino acid substitution as described above in the amino acids constituting the constant region may cause side effects by exhibiting immunogenicity in the human body. It is therefore preferred that only a small number of amino acids be substituted.

Technologies involving amino acid substitution in the variable region (also referred to as V region) of IgG antibodies reported to date include humanization technology (Tsurushita N., Hinton P. R., and Kumar S., Design of humanized antibodies: from anti-Tac to Zenapax, Methods (2005) 36(1), 69-83), affinity maturation where amino acids in the complementarity-determining region (CDR) is substituted in order to increase the binding activity (Rajpal A., Beyaz N., Haber L., Cappuccilli G., Yee H., Bhatt R. R., Takeuchi T., Lerner R. A., and Crea R., A general method for greatly improving the affinity of antibodies by using combinatorial libraries, Proc. Natl. Acad. Sci. USA (2005) 102(24), 8466-71) and amino acid substitution in the amino acids constituting the framework region (FR) for improving the physicochemical stability (Ewert S., Honegger A., and Pluckthun A., Stability improvement of antibodies for extracellular and intracellular applications: CDR grafting to stable frameworks and structure-based framework engineering, Methods (2004) 34(2), 184-99). Unlike the case with amino acid substitution in the constant region (also referred to as C region), amino acid substitution in the variable region is generally used for improving the characteristics (e.g., stability) and enhancing the function (e.g., antigen binding activity) of antibodies. Since the amino acid sequence constituting the CDR of humanized antibodies is derived from the amino acid sequence of a nonhuman animal species, the risk of generating immunogenicity by introducing an artificial amino acid substitution in this sequence is thought to be lower than amino acid substitutions in a sequence in other regions. Moreover, with regard to an artificial amino acid substitution in the amino acid sequence constituting the FR of humanized antibodies, it is thought that such a substitution poses little risk of generating immunogenicity if the FR amino acid sequence obtained as a consequence of substitution is the same as any of the plurality of human antibody FR amino acid sequences that are published in, for example, the Kabat database (ftp.ebi.ac.uk/pub/databases/kabat/), the IMGT database (imgt.cines.fr/), and so forth. Furthermore, the immunogenicity can be reduced by reselecting a human antibody sequence that is very similar to the FR amino acid sequence obtained as a consequence of substitution, from the plurality of human antibody FR amino sequences that are published in the Kabat database, the IMGT database, and so forth (WO 1999/018212).

In contrast, the only methods known for improving the plasma half-life of IgG antibodies are, as described above, amino acid substitution of amino acids constituting the Fc region, which is a part of the constant region, and no methods have been reported to date that bring about an improvement in the plasma half-life of IgG antibodies by amino acid substitution of the amino acids constituting the variable region, which is believed to carry little risk of invoking immunogenicity. The reason for this is, in part, that the plasma half-life of IgG antibodies are believed to largely depend on antigen-dependent depletion and binding to the neonatal Fc receptor, a salvage receptor for IgG antibodies (Lobo E. D., Hansen R. J., and Balthasar J. P., Antibody pharmacokinetics and pharmacodynamics, *J. Pharm. Sci.* (2004) 93(11), 2645-68), and that the functions and properties of the variable region may not have a significant influence on the plasma half-life.

It has also been reported that the isoelectric point (pI) of IgG antibody is lowered by anionization of IgG antibody by succinylation (Yamasaki Y., Sumimoto K., Nishikawa M., Yamashita F., Yamaoka K., Hashida M., and Takakura Y., Pharmacokinetic analysis of in vivo disposition of succinylated proteins targeted to liver nonparenchymal cells via scavenger receptors: importance of molecular size and negative charge density for in vivo recognition by receptors, *Pharmacol. Exp. Ther.* (2002) 301(2), 467-77); and that the pI of IgG antibody is raised by cationization of the IgG antibody by modification with polyamine (Poduslo J. F. and Curran G. L., Polyamine modification increases the permeability of proteins at the blood-nerve and blood-brain barriers, *Neurochem.* (1996) 66(4), 1599-609). However, in both cases there was no increase in the plasma half-life of the modified IgG antibody, but rather the plasma half-life was decreased. Thus, an increase in the plasma half-life of IgG antibodies cannot be realized by modification of the pI of the IgG antibody by the above-described chemical modification of the IgG antibody.

SUMMARY OF THE INVENTION

The present invention was pursued in view of the circumstances described above. An object of the present invention is to provide a method of modulating the plasma (blood) half-life of anti-glypican 3 antibody, an anti-glypican 3 antibody having a modulated plasma half-life and a pharmaceutical composition comprising the antibody as an active ingredient, as well as a method of preparing the anti-glypican 3 antibody and the pharmaceutical composition. Another object of the present invention is to provide a method for modulating cytotoxicity of an antibody by modulating the plasma half-life of the antibody having cytotoxicity, an antibody with modulated cytotoxicity and a pharmaceutical composition, comprising the antibody, as well as a method of preparing the antibody and the pharmaceutical composition.

The present inventors carried out focused investigations into methods for modulating the plasma half-life of an antibody (e.g. anti-glypican 3 antibody). As a result, the present inventors discovered that the plasma half-life of an antibody (e.g. anti-glypican 3 antibody) can be modulated by modifying—among the amino acid residues constituting the variable region and the constant region of an antibody (e.g. anti-glypican 3 antibody)—amino acid residues exposed on the surface of this antibody molecule and thereby controlling the surface charge of the antibody molecule. Specifically, among the amino acid residues in the amino acid sequence constituting the variable region and the constant region of an antibody (e.g. anti-glypican 3 antibody), particular amino acid residues were identified that can modulate the plasma half-life of the antibody (e.g. anti-glypican 3 antibody) through modifying the surface charge on the antibody molecule without affecting the structure or function of the antibody, e.g., the antigen binding activity. The present inventors also confirmed that an antibody (e.g. anti-glypican 3 antibody) having a half-life modulated in this manner in fact retains its antigen binding activity. The present inventors also found that modulation of the plasma half-life of an antibody (e.g. anti-glypican 3 antibody) increases the tumor proliferation inhibiting activity on cancer cells exhibited by cytotoxic antibodies, such as the anti-glypican 3 antibody.

The present invention relates to a method of modulating the plasma half-life of an antibody (e.g. anti-glypican 3 antibody) by modifying an amino acid residue that is exposed on the surface of the antibody, an antibody (e.g. anti-glypican 3 antibody) that has a modulated plasma half-life by amino acid residue modification, a pharmaceutical composition comprising the antibody as an active ingredient, and a method of preparing such a pharmaceutical composition. More specifically, the present invention provides the following:

[1] A method for preparing an anti-glypican 3 antibody with modulated plasma kinetics, said method comprising the steps of:

(a) culturing a host cell bearing a nucleic acid that encodes the anti-glypican 3 antibody under conditions allowing for expression of the nucleic acid, wherein the anti-glypican 3 antibody has an amino acid sequence altered to causes a modification in the charge of at least one amino acid residue that can be exposed on the surface of the antibody; and (b) recovering the anti-glypican 3 antibody from the host cell culture;

[2] The method according to [1], wherein the modulation of the plasma kinetics is increase or decrease in a parameter selected from the plasma half life, the mean plasma residence time, and the plasma clearance;

[3] The method according to [1], wherein the modification in the charge of the amino acid residue is achieved by amino acid substitution;

[4] The method according to [1], wherein the amino acid residue that can be exposed on the surface of the anti-glypican 3 antibody is located in a region in the anti-glypican 3 antibody other than the FcRn binding region;

[5] The method according to [4], wherein the FcRn binding region comprises the Fc region;

[6] The method according to [4], wherein the FcRn binding region comprises the amino acid residues of the EU numbers 250, 253, 310, 311, 314, 428, 435, 436 according to the Kabat numbering;

[7] The method according to [1], wherein the anti-glypican 3 antibody is an IgG antibody;

[8] The method according to [1]-[7], wherein the amino acid residue whose charge is modified is an amino acid residue present in the heavy chain variable region or the light chain variable region;

[9] The method according to [8], wherein the anti-glypican 3 antibody comprises a complementarity-determining region (CDR) derived from a non-human animal, a framework region (FR) derived from human, and a constant region derived from human, and wherein the modification in the charge of the amino acid residue is achieved by substitution of at least one amino acid residue that can be exposed on the antibody surface in the CDR or FR of the antibody with an amino acid residue that has a charge different from that of the amino acid residue;

[10] The method according to [9], wherein the modification in the charge of the amino acid residue is achieved by:

(1) at least one substitution in the heavy chain variable region shown in SEQ ID NO: 1 selected from:

(a) substitution of Q that is the 43rd amino acid residue with K, (b) substitution of D that is the 52nd amino acid residue with N, and (c) substitution of Q that is the 107th amino acid residue with R;

and/or (2) at least one substitution in the light chain variable region shown in SEQ ID NO: 7 selected from:

(d) substitution of E that is the 17th amino acid residue with Q, (e) substitution of Q that is the 27th amino acid residue with R, and (f) substitution of Q that is the 105th amino acid residue with R;

[11] The method according to [9], wherein the modification in the charge of the amino acid residue is achieved by:

(1) at least one substitution in the heavy chain variable region shown in SEQ ID NO: 1 selected from:

(a) substitution of K that is the 19th amino acid residue with T, (b) substitution of Q that is the 43rd amino acid residue with E, (c) substitution of Q that is the 62nd amino acid residue with E, (d) substitution of K that is the 63rd amino acid residue with S, (e) substitution of K that is the 65th amino acid residue with Q, and (f) substitution of G that is the 66th amino acid residue with D;

and/or (2) at least one substitution in the light chain variable region shown in SEQ ID NO: 7 selected from:

(g) substitution of R that is the 24th amino acid residue with Q, (h) substitution of Q that is the 27th amino acid residue with E, (i) substitution of K that is the 79th amino acid residue with T, (j) substitution of R that is the 82nd amino acid residue with S, and (k) substitution of K that is the 112nd amino acid residue with E;

[12] The method according to [11], further comprising at least one modification in the heavy chain constant region shown in SEQ ID NO: 31 selected from:

(a) substitution of H that is the 151st amino acid residue with Q, (b) substitution of K that is the 157th amino acid residue with Q, (c) substitution of R that is the 238th amino acid residue with Q, (d) substitution of D that is the 239th amino acid residue with E, (e) substitution of L that is the 241st amino acid residue with M, and (f) substitution of Q that is the 302nd amino acid residue with E;

[13] The method according to [9]-[12], wherein the anti-glypican 3 antibody has a reduced content of fucose attached to the Fc region of the antibody;

[14] An anti-glypican 3 antibody prepared by the method according to [1]-[13];

[15] A method for preparing an antibody with modulated plasma kinetics, said method comprising the steps of:

(a) culturing a host cell bearing a nucleic acid that encodes the antibody under conditions allowing for expression of the nucleic acid, wherein the antibody has an amino acid sequence altered to causes a modification in the charge of at least one amino acid residue in the constant region in the antibody other than the FcRn binding region; and (b) recovering the antibody from the host cell culture;

[16] The method according to [15], wherein the modulation of the plasma kinetics is increase or decrease in a parameter selected from the plasma half life, the mean plasma residence time, and the plasma clearance;

[17] The method according to [15], wherein the modification in the charge of the amino acid residue is achieved by amino acid substitution;

[18] The method according to [17], wherein the antibody is an IgG antibody;

[19] The method according to [18], wherein the antibody is an IgG1 antibody;

[20] The method according to [17], wherein the modification in the charge of the amino acid residue is achieved by substitution of at least one amino acid residue of an IgG1 antibody with a corresponding amino acid residue of an IgG4 antibody;

[21] The method according to [15]-[20], wherein the FcRn binding region comprises the amino acid residues of the EU numbers 250, 253, 310, 311, 314, 428, 435, and 436 according to the Kabat numbering;

[22] The method according to [20], wherein the modification in the charge of the amino acid residue is achieved by at least one substitution in the heavy chain constant region shown in SEQ ID NO: 31 selected from:

(a) substitution of H that is the 151st amino acid residue with Q, (b) substitution of K that is the 157th amino acid residue with Q, (c) substitution of R that is the 238th amino acid residue with Q, (d) substitution of D that is the 239th amino acid residue with E, (e) substitution of L that is the 241st amino acid residue with M, and (f) substitution of Q that is the 302nd amino acid residue with E;

[23] The method according to [15]-[22], wherein the antibody is an anti-glypican 3 antibody;

[24] A method of stabilizing an anti-glypican 3 antibody that comprises a complementarity-determining region (CDR) derived from a non-human animal, a framework region (FR) derived from human, and a constant region derived from human, said method comprising the steps of:

(a) culturing a host cell bearing a nucleic acid that encodes the anti-glypican 3 antibody under conditions allowing for expression of the nucleic acid, wherein the anti-glypican 3 antibody has an amino acid sequence altered to increase in the Tm value of the antibody by a modification of at least one amino acid residue; and (b) recovering the antibody from the host cell culture;

[25] The method according to [24], wherein the amino acid residue is present in the FR1 region and/or the FR2 region of the heavy chain or the light chain;

[26] The method according to [25], wherein an amino acid residue in the FR2 region of the heavy chain is substituted with an amino acid residue of the FR2 region of the VH4 subclass;

[27] The method according to [25], wherein an amino acid residue in the FR2 region of the light chain is substituted with an amino acid residue of the FR2 region of the VK3 subclass;

[28] The method according to [24]-[27], wherein the substitution of the amino acid residue is achieved by:

(1) at least one substitution in the heavy chain variable region shown in SEQ ID NO: 1 selected from:

(a) substitution of V that is the 37th amino acid residue with I, (b) substitution of A that is the 40th amino acid residue with P, (c) substitution of M that is the 48th amino acid residue with I, and (d) substitution of L that is the 51st amino acid residue with I;

and/or (2) at least one substitution in the light chain variable region shown in SEQ ID NO: 7 selected from:

(e) substitution of L that is the 42nd amino acid residue with Q, (f) substitution of S that is the 48th amino acid residue with A, and (g) substitution of Q that is the 50th amino acid residue with R;

[29] A method for preparing an antibody with modulated cytotoxicity, comprising the steps of:

(a) culturing a host cell bearing a nucleic acid that encodes the antibody under conditions allowing for expression of the nucleic acid, wherein the antibody has an amino acid sequence altered to causes a modification in the charge of at least one amino acid residue that can be exposed on the surface of a cytotoxic antibody; and (b) recovering the antibody from the host cell culture;

[30] The method according to [29], wherein the modification in the charge of the amino acid residue is achieved by amino acid substitution;

[31] The method according to [29], wherein the amino acid residue that can be exposed on the surface of the antibody is located in a region in the antibody other than the FcRn binding region;

[32] The method according to [31], wherein the FcRn binding region comprises the Fc region;

[33] The method according to [31], wherein the FcRn binding region comprises the amino acid residues of the EU numbers 250, 253, 310, 311, 314, 428, 435, 436 according to the Kabat numbering;

[34] The method according to [29], wherein the antibody is an IgG antibody;

[35] The method according to [29]-[34], wherein the amino acid residue whose charge is modified is an amino acid residue present in the constant region of the antibody;

[36] The method according to [29]-[34], wherein the amino acid residue whose charge is modified is an amino acid residue present in the heavy chain variable region or the light chain variable region of the antibody;

[37] The method according to [36], wherein the antibody is an antibody that comprises a complementarity-determining region (CDR) derived from a non-human animal, a framework region (FR) derived from human, and a constant region derived from human, and wherein the modification in the charge of the amino acid residue is achieved by substitution of at least one amino acid residue that can be exposed on the antibody surface in the CDR or FR of the antibody with an amino acid residue that has a charge different from that of the amino acid residue;

[38] The method according to [37], wherein the modification in the charge of the amino acid residue is achieved by:

(1) at least one substitution in the heavy chain variable region shown in SEQ ID NO: 1 selected from:

(a) substitution of K that is the 19th amino acid residue with T, (b) substitution of Q that is the 43rd amino acid residue with E, (c) substitution of Q that is the 62nd amino acid residue with E, (d) substitution of K that is the 63rd amino acid residue with S, (e) substitution of K that is the 65th amino acid residue with Q, and (f) substitution of G that is the 66th amino acid residue with D;

and/or, (2) at least one substitution in the light chain variable region shown in SEQ ID NO: 7 selected from:

(g) substitution of R that is the 24th amino acid residue with Q, (h) substitution of Q that is the 27th amino acid residue with E, (i) substitution of K that is the 79th amino acid residue with T, (j) substitution of R that is the 82nd amino acid residue with S, and (k) substitution of K that is the 112nd amino acid residue with E;

[39] The method according to [38], further comprising at least one substitution in the heavy chain constant region shown in SEQ ID NO: 31 selected from:

(a) substitution of H that is the 151st amino acid residue with Q, (b) substitution of K that is the 157th amino acid residue with Q, (c) substitution of R that is the 238th amino acid residue with Q, (d) substitution of D that is the 239th amino acid residue with E, (e) substitution of L that is the 241st amino acid residue with M, and (f) substitution of Q that is the 302nd amino acid residue with E;

[40] The method according to [36], wherein the antibody comprises a complementarity-determining region (CDR) derived from a non-human animal; a framework region (FR) derived from human, and a constant region derived from human, and wherein the modification in the charge of the amino acid residue is achieved by substitution of at least one amino acid residue that can be exposed on the antibody surface in the constant region of the antibody with an amino acid residue that has a charge different from that of the amino acid residue;

[41] The method according to [40], wherein the substitution is at least one substitution in the heavy chain constant region shown in SEQ ID NO: 31 selected from:

(a) substitution of H that is the 151st amino acid residue with Q, (b) substitution of K that is the 157th amino acid residue with Q, (c) substitution of R that is the 238th amino acid residue with Q, (d) substitution of D that is the 239th amino acid residue with E, (e) substitution of L that is the 241st amino acid residue with M, and (f) substitution of Q that is the 302nd amino acid residue with E;

[42] The method according to [37]-[41], wherein the antibody has a reduced content of fucose attached to the Fc region of the antibody;

[43] An antibody prepared by the method according to [29]-[42];

[44] The antibody according to [43], wherein the antibody is an anti-glypican 3 antibody;

[45] An antibody comprising:

(1) a heavy chain variable region shown in SEQ ID NO: 1 in which the amino acid sequence comprises at least one substitution selected from:

(a) substitution of K that is the 19th amino acid residue with T, (b) substitution of Q that is the 43rd amino acid residue with E, (c) substitution of Q that is the 62nd amino acid residue with E, (d) substitution of K that is the 63rd amino acid residue with S, (e) substitution of K that is the 65th amino acid residue with Q, and (f) substitution of G that is the 66th amino acid residue with D;

and/or (2) a light chain variable region shown in SEQ ID NO: 7 in which the amino acid sequence comprises at least one substitution selected from:

(g) substitution of R that is the 24th amino acid residue with Q, (h) substitution of Q that is the 27th amino acid residue with E, (i) substitution of K that is the 79th amino acid residue with T, (j) substitution of R that is the 82nd amino acid residue with S, and (k) substitution of K that is the 112nd amino acid residue with E;

[46] The antibody according to [45], comprising the heavy chain shown in SEQ ID NO: 3 and the light chain shown in SEQ ID NO: 9;

[47] The antibody according to [45], comprising the heavy chain shown in SEQ ID NO: 5 and the light chain shown in SEQ ID NO: 11;

[48] The antibody according to [45] which comprises a heavy chain variable region shown in SEQ ID NO: 27 and a light chain variable region shown in SEQ ID NO: 28;

[49] The antibody according to [45] which comprises a heavy chain variable region shown in SEQ ID NO: 27 and a light chain variable region shown in SEQ ID NO: 29;

[50] The antibody according to [45]-[49] comprising a constant region of a human antibody;

[51] The antibody according to [50], wherein the constant region comprises a sequence shown in SEQ ID NO: 32 or SEQ ID NO: 33;

[52] An antibody comprising:

(1) a heavy chain variable region shown in SEQ ID NO: 1 in which the amino acid sequence comprises at least one substitution selected from:

(a) substitution of Q that is the 43rd amino acid residue with K, (b) substitution of D that is the 52nd amino acid residue with N, and (c) substitution of Q that is the 107th amino acid residue with R;

and (2) a light chain variable region shown in SEQ ID NO: 7 in which the amino acid sequence comprises at least one substitution selected from:

(d) substitution of E that is the 17th amino acid residue with Q, (e) substitution of Q that is the 27th amino acid residue with R, and (f) substitution of Q that is the 105th amino acid residue with R;

[53] The antibody according to [52], comprising the heavy chain variable region shown in SEQ ID NO: 4 and the light chain variable region shown in SEQ ID NO: 10;

[54] The antibody according to [52], comprising the heavy chain variable region shown in SEQ ID NO: 6 and the light chain variable region shown in SEQ ID NO: 12;

[55] The antibody according to [52]-[54] comprising a constant region of a human antibody;

[56] An antibody comprising at least one substitution in the amino acid sequence of the heavy chain constant region shown in SEQ ID NO: 31 selected from:

(a) substitution of H that is the 151st amino acid residue with Q, (b) substitution of K that is the 157th amino acid residue with Q, (c) substitution of R that is the 238th amino acid residue with Q, (d) substitution of D that is the 239th amino acid residue with E, (e) substitution of L that is the 241st amino acid residue with M, and (f) substitution of Q that is the 302nd amino acid residue with E;

[57] An antibody comprising a heavy chain constant region shown in SEQ ID NO: 33;

[58] The antibody according to [45]-[57], wherein the antibody has a reduced content of fucose attached to the Fc region of the antibody;

[59] A composition comprising the antibody according to [45]-[58] and a pharmaceutically acceptable carrier.

[60] An anticancer agent comprising as an active ingredient the antibody according to [45]-[58];

[61] The anticancer agent according to [60], wherein the cancer is liver cancer;

[62] A nucleic acid that encodes a polypeptide of the antibody according to [45]-[58];

[63] A host cell comprising the nucleic acid according to [62];

[64] The host cell according to [63], wherein the host cell is a fucose transporter-deficient animal cell, a fucosyltransferase-deleted animal cell, or an animal cell in which a complex branched sugar chain modification is modified;

[65] A method for preparing an antibody comprising culturing the host cell according to [63] or [64] and recovering a polypeptide from the cell culture.

BRIEF DESCRIPTION OF THE DRAWINGS

FIG. 7A shows the antitumor activity of the H0L0 antibody, Hspu2.2Lspu2.2 (Hu2.2Lu2.2) antibody, and Hspd1.8Lspd1.6 (Hd1.8Ld1.6) antibody in a human liver cancer-transplant mouse model when each test antibody was administered to the model at a dose of 5 mg/kg, wherein the black diamond shows the activity for the administration of vehicle, the black triangle shows the effect of the administration of the Hspd1.8Lspd1.6 (Hd1.8Ld1.6) antibody, the white circle shows the effect of the administration of the Hspu2.2Lspu2.2 (Hu2.2Lu2.2) antibody, and the black square shows the effect of the administration of the H0L0 antibody;

FIG. 7B shows the antitumor activity of the H0L0 antibody, Hspu2.2Lspu2.2 (Hu2.2Lu2.2) antibody, and Hspd1.8Lspd1.6 (Hd1.8Ld1.6) antibody in a human liver cancer-transplant mouse model when each test antibody was administered to the model at a dose of 1 mg/kg, wherein the black diamond shows the activity for the administration of vehicle, the black triangle shows the effect of the administration of the Hspd1.8Lspd1.6 (Hd1.8Ld1.6) antibody, the white circle shows the effect of the administration of the Hspu2.2Lspu2.2 (Hu2.2Lu2.2) antibody, and the black square shows the effect of the administration of the H0L0 antibody;

FIG. 8A shows the plasma concentration of the antibody for the H0L0 antibody, Hspu2.2Lspu2.2 (Hu2.2Lu2.2) antibody, and Hspd1.8Lspd1.6 (Hd1.8Ld1.6) antibody administered to a human liver cancer-transplant mouse model when each test antibody was administered to the model at a dose of 5 mg/kg, wherein the black triangle shows the plasma concentration of the Hspd1.8Lspd1.6 (Hd1.8Ld1.6) antibody, the white circle shows the plasma concentration of the Hspu2.2Lspu2.2 (Hu2.2Lu2.2) antibody, and the black square shows the plasma concentration of the H0L0 antibody;

FIG. 8B shows the plasma concentration of the antibody, for the H0L0 antibody, Hspu2.2Lspu2.2 (Hu2.2Lu2.2) antibody, and Hspd1.8Lspd1.6 (Hd1.8Ld1.6) antibody in a human liver cancer-transplant mouse model when each test antibody was administered to the model at a dose of 1 mg/kg, wherein the black triangle shows the plasma concentration of the Hspd1.8Lspd1.6 (Hd1.8Ld1.6) antibody, the white circle shows the plasma concentration of the Hspu2.2Lspu2.2 (Hu2.2Lu2.2) antibody, and the black square shows the plasma concentration of the H0L0 antibody.

DESCRIPTION OF THE PREFERRED EMBODIMENTS

Figure 1:
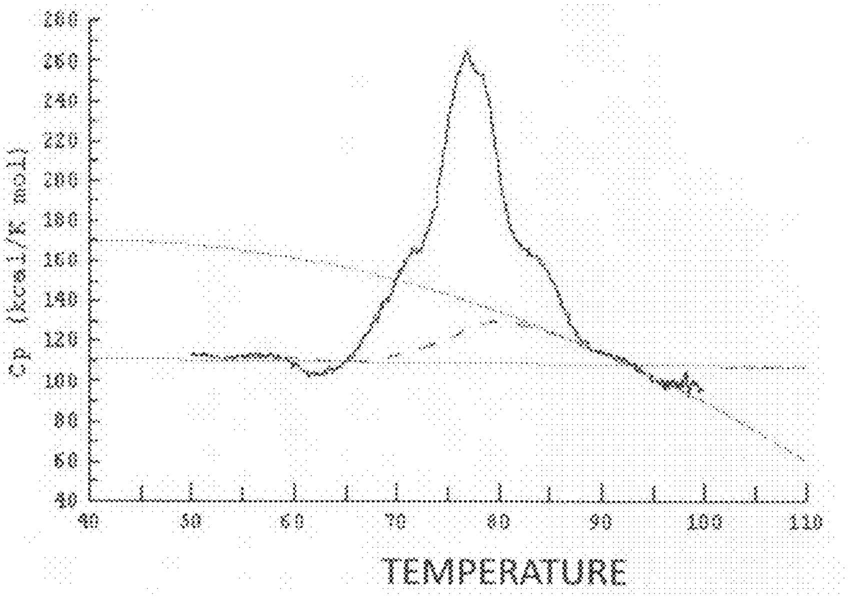
FIG. 1 is a chart obtained from the differential scanning calorimetric (DSC) measurement of the Hspu2.2Lspu2.2 (Hu2.2Lu2.2) antibody.

The present invention provides a method of modulating the plasma kinetics of an antibody (e.g. anti-glypican 3 antibody). In a preferred embodiment of the present invention, the method comprises the modification in the charge of at least one amino acid residue that can be exposed on the surface of the antibody (e.g. anti-glypican 3 antibody). That is, the plasma kinetics of an antibody (e.g. anti-glypican 3 antibody) can be modulated by modifying the charge of an amino acid residue in the antibody to cause a change in the isoelectric point (pI) thereof. The antibody (e.g. anti-glypican 3 antibody) having modulated plasma kinetics is able to exhibit an antitumor activity on cancer cells that is superior to that of the unmodulated antibody.

Among the several antibody isotypes, the principle metabolic pathways of the IgG antibody do not proceed via renal excretion due to the sufficiently high molecular weight of the IgG antibody. The IgG antibody, which contains the Fc region as a part of its molecule, is known to have a long in vivo half-life due to recycling by a salvage pathway mediated by the neonatal Fc receptor (FcRn), which is expressed by endothelial cells in, for example, the vascular system. It is thought that the IgG antibody is metabolized mainly by metabolic pathways in endothelial cells (He X. Y., Xu Z., Melrose J., Mullowney A., Vasquez M., Queen C., Vexler V., Klingbeil C., Co M. S., and Berg E. L., Humanization and pharmacokinetics of a monoclonal antibody with specificity for both E- and P-selectin, *J. Immunol.* (1998), 160(2), 1029-35). That is, it is thought that the IgG antibody is recycled through binding to the FcRn of IgG antibody nonspecifically taken up by the endothelial cell, while the IgG antibody that cannot be bound is metabolized. IgG antibody having the Fc region modified to lower the binding activity to FcRn exhibits a shorter half-life in the plasma. In contrast, the plasma half-life of the IgG antibody can be increased by modifying amino acid residues constituting the Fc region of the IgG antibody so as to increase the binding activity to FcRn (He X. Y., Xu Z., Melrose J., Mullowney A., Vasquez M., Queen C., Vexler V., Klingbeil C., Co M. S., and Berg E. L., Humanization and pharmacokinetics of a monoclonal antibody with specificity for both E- and P-selectin, *J. Immunol.* (1998), 160(2), 1029-35; and LinksOber R J, Radu C G, Ghetie V, Ward E S. Differences in promiscuity for antibody-FcRn interactions across species: implications for therapeutic antibodies. *Int Immunol.* (2001) 13(12), 1551-9). As described above, the known methods for modulating the plasma kinetics of the IgG antibody involved modification of the binding activity to FcRn by modification of amino acid residues constituting the Fc region. Specific examples of the above amino acid residues include the amino acid residues H250, H253, H310, H311, H314, H428, H435 and H436, according to the Kabat numbering. In addition, the amino acid residues H254, H255, H257, H288, H296, H307, H309, H315, H415, H433, which indirectly involve the interaction between IgG antibodies and FcRn, were thought to be the target for modification. These amino acid residues correspond to, for example, the 130, 133, 190, 191, 194, 308, 315 and 316th amino acid residues, and the 134, 135, 137, 168, 176, 187, 189, 195, 295 and 313rd amino acid residues in SEQ ID NO:30, as well as the 133, 136, 193, 194, 197, 311, 318 and 319th amino acid residues and the 137, 138, 140, 171, 179, 190, 192, 198, 298 and 316th amino acid residues in SEQ ID NO:31, respectively. However, as shown in the examples provided below, it has now found by the present invention that the plasma half-life of an antibody (e.g. anti-glypican 3 antibody) depends on the pI with a high correlation. Thus, it is now shown that the plasma half-life of the antibody (e.g. anti-glypican 3 antibody) can be modulated without modifying the amino acid residues constituting FcRn binding region, whose modification would invoke the immunogenicity, in particular the amino acid residues H250, H253, H310, H311, H314, H428, H435 and H436, as well as H254, H255, H257, H288, H296, H307, H309, H315, H415 and H433 according to the Kabat numbering. It was also a surprising result that the modification in the amino acid residues other than H250, H253, H310, H311, H314, H428, H435 and H436, as well as H254, H255, H257, H288, H296, H307, H309, H315, H415 and H433 exhibited a decrease in the pI value and change in the biding activity to FcRn.

While not wishing to be bound to a particular theory, the present inventors hold the following view at the present time. The rate of nonspecific uptake of the IgG antibody by endothelial cells is thought to depend on physicochemical Coulombic interaction between the IgG antibody and the negatively charged cell surface. It is therefore thought that decrease (increase) in the Coulombic interaction by lowering (raising) the pI of the IgG antibody may cause decrease (increase) in nonspecific uptake by the endothelial cell, which in turn causes decrease (increase) in metabolism at the endothelial cell resulted in the modulation of plasma kinetics. As used herein, “decreasing the Coulombic interaction” means an increase in the Coulombic forth as expressed in a repulsive force. Since Coulombic interaction between the antibody and the cell surface negative charge of the endothelial cell is a physicochemical interaction, it is believed that this interaction does not primarily depend on the amino acid sequence per se that constitutes the antibody. Therefore, the method of modulating the plasma kinetics discovered in the present invention can be broadly applied to any antibodies or anti-glypican 3 antibodies but not limited to only a specific antibody or anti-glypican 3 antibody.

When an IgG antibody is used as the antibody (e.g. anti-glypican 3 antibody) of the present invention, any subtype may be used as long as it is an IgG-type antibody molecule. A bispecific IgG antibody may also be used. When the antibody (e.g. anti-glypican 3 antibody) of the present invention is a bispecific antibody, the antibody can also specifically bind both the corresponding antigen (glypican 3 molecule in the case of anti-glypican 3 antibody) and an epitope other than that antigen. For example, in order to recruit NK cells, cytotoxic T-cells, LAK cells, and so forth, a surface antigen that specifically binds to these cells may be suitably used as another antigen. It has been shown that cytotoxicity by LAK cells is exhibited against bile duct cancer using a bispecific antibody produced from the MUSE11 antibody recognizing MUC1 (an adenocarcinoma-related antigen), and OKT3 antibody recognizing LAK cell surface antigen (Katayose Y., Kudo T., Suzuki M., Shinoda M., Saijyo S., Sakurai N., Saeki H., Fukuhara K., Imai K., and Matsuno S., MUC1-specific targeting immunotherapy with bispecific antibodies: inhibition of xenografted human bile duct carcinoma growth, *Cancer Res.* (1996) 56(18), 4205-12). The antibody (e.g. anti-glypican 3 antibody) having improved plasma kinetics of the present invention can be suitably used in place of the MUSE11 antibody recognizing MUC1. In addition, antibody that recognizes different epitopes of the antigen to which the antibody binds (glypican 3 molecule in the case of anti-glypican 3 antibody) can also be suitably used as the bispecific antibody (e.g. anti-glypican 3 antibody) of the present invention. In the case of low molecular weight antibodies for which renal excretion is the main metabolic pathway, such as scFv and Fab, the plasma kinetics of such antibodies cannot be modulated by the pI as described above. However, the present invention can be applied to any antibody molecule type if it is an Fc-coupled protein for which renal excretion is not the main metabolic pathway. Examples of such molecules include scFv-Fc, dAb-Fc and Fc fusion proteins. Since the main metabolic pathway of these molecules is not via metabolism by renal excretion, the plasma kinetics of these molecules can be modulated by changing the pI according to the method of the present invention. Antibody-like molecules are included in the antibody molecules envisaged by the invention. Antibody-like molecules are molecules that function by binding to a target molecule (Binz H. K., Amstutz P., and Pluckthun A., Engineering novel binding proteins from nonimmunoglobulin domains, *Nat. Biotechnol.* (2005) 23(10), 1257-68); and examples include DARPins, Affibody, and Avimer.

The term "modulated plasma kinetics" as used herein means that the plasma kinetics are modified in a desired direction when the plasma kinetics of the antibody after modification of the amino acids constituting the antibody (e.g. anti-glypican 3 antibody) are compared with the plasma kinetics of the antibody prior to modification. Thus, when it is desired to increase the plasma half-life of the antibody (e.g. anti-glypican 3 antibody), "modulation of the plasma kinetics" refers to an increase in the plasma half-life of the antibody. When it is desired to decrease the plasma half-life of the antibody (e.g. anti-glypican 3 antibody), "modulation of the plasma kinetics" refers to decrease in the plasma half-life of the antibody.

Whether the plasma kinetics of the antibody (e.g. anti-glypican 3 antibody) of the present invention have been modified in the desired direction, that is, whether the plasma kinetics have been modulated as desired, can be appropriately evaluated by pharmacokinetic tests using, for example, mouse, rat, rabbit, dog, monkey, and so forth. In addition, an "extension of the plasma half-life" or a "decrease of the plasma half-life" as used herein may also be comprehended via parameters other than the plasma half-life parameter, such as the mean plasma residence time and the plasma clearance (*Pharmacokinetics Analysis by Practice*, (Nanzando)). For example, the "modulation of the plasma kinetics" according to the present invention can be suitably evaluated with these parameters by carrying out noncompartmental analysis according to the instructions accompanying the WinNonlin (Pharsight) in vivo pharmacokinetic analysis software.

The phrase "amino acid residue that can be exposed on the surface" as used herein generally denotes an amino acid residue that resides on the surface of the polypeptide constituting the antibody (e.g. anti-glypican 3 antibody). The phrase "amino acid residue that resides on the surface of the polypeptide" refers to an amino acid residue whose side chain can come into contact with solvent molecules (typically water molecules). All of its side chain need not come into contact with solvent molecules. If even a portion of the side chain of an amino acid residue comes into contact with solvent molecules, such an amino acid residue is considered to be an amino acid residue that resides on the surface. Those skilled in the art can construct a homology model of the polypeptide or antibody using commercially available homology modeling software. Based on this homology model, amino acid residues on the surface of the polypeptide constituting the antibody (e.g. anti-glypican 3 antibody) can be appropriately selected as an "amino acid residue that resides on the surface of the polypeptide".

The "amino acid residue that can be exposed on the surface" is not particularly limited in the present invention, but is preferably an amino acid residue residing outside the FcRn binding region of the antibody (e.g. anti-glypican 3 antibody). The FcRn binding region is preferably the Fc region, but also include, for example, a region consisting of one or more amino acid residues H250, H253, H310, H311, H314, H428, H435 and H436 according to the Kabat numbering. In addition, the amino acid residues H254, H255, H257, H288, H296, H307, H309, H315, H415, H433, which indirectly involve the interaction between IgG antibodies and FcRn, were thought to be the target for modification. These amino acid residues correspond to, for example, the 130, 133, 190, 191, 194, 308, 315 and 316th amino acid residues, and the 134, 135, 137, 168, 176, 187, 189, 195, 295 and 313rd amino acid residues in SEQ ID NO:30, as well as the 133, 136, 193, 194, 197, 311, 318 and 319th amino acid residues and the 137, 138, 140, 171, 179, 190, 192, 198, 298 and 316th amino acid residues in SEQ ID NO:31, respectively.

The amino acid residue to be subjected to charge modification in the antibody (e.g. anti-glypican 3 antibody) according to the present invention is preferably an amino acid residue constituting the heavy chain (H chain) variable region or the light chain (L chain) variable region of the antibody. Preferred specific examples of these variable regions are the complementarity-determining region (CDR) and framework region (FR).

Those skilled in the art can appropriately select a surface amino acid residue in the antibody's variable region based on a homology model built by homology modeling. Thus, a surface amino acid residue in the antibody's variable region can be suitably selected from H1, H3, H5, H8, H10, H12, H13, H15, H16, H19, H23, H25, H26, H39, H42, H43, H44, H46, H68, H71, H72, H73, H75, H76, H81, H82b, H83, H85, H86, H105, H108, H110, and H112, which are amino acid residues according to the Kabat numbering. For example, in the FR of the humanized anti-glypican 3 antibody heavy chain shown in SEQ ID NO: 1, the surface amino residues may include, but not limited to, the amino acid residues at positions 1, 3, 5, 8, 10, 12, 13, 15, 16, 19, 23, 25, 26, 39, 42, 43, 44, 46, 69, 72, 73, 74, 76, 77, 82, 85, 87, 89, 90, 107, 110, 112, and 114. A surface amino acid residue in the heavy chain CDR can also be selected using the same homology model. Thus, H97, an amino acid residue according to the Kabat numbering, is exposed at the surface for almost all antibodies. For example, the serine at position 101 in the heavy chain CDR of the humanized anti-glypican 3 antibody shown in SEQ ID NO: 1 corresponds to that amino acid residue. Suitable examples of other amino acid residues in the heavy chain CDR of the humanized anti-glypican 3 antibody shown in SEQ ID NO: 1 are the amino acid residues at positions 52, 54, 62, 63, 65, and 66.

With respect to the light chain FR, surface amino acid residues in the antibody's variable region can be suitably selected from L1, L3, L7, L8, L9, L11, L12, L16, L17, L18, L20, L22, L38, L39, L41, L42, L43, L45, L46, L49, L57, L60, L63, L65, L66, L68, L69, L70, L74, L76, L77, L79, L80, L81, L85, L100, L103, L105, L106, and L107 of amino acid residues according to the Kabat numbering. For example, surface amino acids may include, but not limited to, 1, 3, 7, 8, 9, 11, 12, 16, 17, 18, 20, 22, 43, 44, 45, 46, 48, 49, 50, 54, 62, 65, 68, 70, 71, 73, 74, 75, 79, 81, 82, 84, 85, 86, 90, 105, 108, 110, 111, and 112 of the humanized anti-glypican 3 antibody shown in SEQ ID NO: 7. Surface amino acid residues in the light chain CDR can be selected using the same homology model as the homology model with which the surface amino acid residues in the heavy chain CDR were determined. Suitable examples of amino acid residues in the CDR of the humanized anti-glypican 3 antibody light chain shown in SEQ ID NO: 7 are the amino acid residues at positions 24, 27, 33, 55, and 59.

The term "modification" in an amino acid residue in the method of the present invention specifically denotes, inter alia, substitution of an original amino acid residue with another amino acid residue, deletion of an original amino acid residue, and addition of a new amino acid residue, and preferably indicates the substitution of an original amino acid residue with another amino acid residue. Thus, "modification in the charge of an amino acid residue" in the present invention is preferably an amino acid substitution.

In order to carry out "modification in the charge of an amino acid residue" on the anti-glypican 3 antibody of the present invention, for example, the charge is preferably modified for at least one amino acid residue selected from the amino acid residues at positions 19, 43, 52, 54, 62, 63, 65, 66, and 107 in the heavy chain variable region constituting the humanized anti-glypican 3 antibody shown in SEQ ID NO: 1. In addition, the charge is preferably modified, for example, for at least one amino acid residue selected from the amino acid residues at positions 17, 24, 27, 33, 55, 59, 79, 82, 105 and 112 in the light chain variable region constituting the humanized anti-glypican 3 antibody shown in SEQ ID NO: 7. Among the amino acid residues listed above, amino acid residues other than those modified in its charge need not be modified as long as the desired modulating effect on the plasma kinetics is being obtained; however, such amino acid residues may conventionally modified so as to have no charge or to have the same type of charge as the modified amino residue(s).

Charge-bearing amino acids are known to be present. In general, lysine (K), arginine (R), and histidine (H) are known as positively charged amino acids. Aspartic acid (D) and glutamic acid (E) are known as negatively charged amino acids. The amino acids other than these are known as the uncharged amino acids.

Preferably the aforementioned "modified amino acid residue" is conventionally selected from, but not limited to, the amino acid residues present in either of the following groups (a) and (b).

(a) glutamic acid (E), aspartic acid (D)

(b) lysine (K), arginine (R), and histidine (H)

When the original (pre-modification) amino acid residue already bears a charge, modification so as to provide an uncharged amino acid residue is also a preferred embodiment of the present invention. Thus, modification in the present invention encompasses (1) substitution of a charged amino acid with an uncharged amino acid, (2) substitution of a charged amino acid with an amino acid bearing an opposite charge, and (3) substitution of an uncharged amino acid with a charged amino acid.

Modification of an amino acid residue constituting the antibody (e.g. anti-glypican 3 antibody) so as to change the isoelectric point (pI) of the antibody is preferred for the present invention. In addition, in those instances where a plurality of amino acid residues will be modified, the amino acid residues subjected to modification may include a small number of uncharged amino acid residues.

Suitable examples of the "modification in the charge of an amino acid residue" in the anti-glypican 3 antibody of the present invention are as follows. With regard to a modification that increases the pI value, for example, at least one substitution selected from Q43K, D52N, and Q107R in the heavy chain variable region constituting the humanized anti-glypican 3 antibody shown in SEQ ID NO: 1 can be made, and a modification to the amino acid sequence shown in SEQ ID NO: 4 or 6 is particularly preferred. In addition, for example, at least one substitution selected from E17Q, Q27R, and Q105R in the light chain variable region constituting the humanized anti-glypican 3 antibody shown in SEQ ID NO: 7 can be made, and a modification to the amino acid sequence shown in SEQ ID NO: 10 or 12 is particularly preferred. With regard, on the other hand, to a modification that decreases the pI value, at least one substitution selected from K19T, Q43E, G62E, K63S, K65Q, and G66D in the heavy chain variable region constituting the humanized anti-glypican 3 antibody shown in SEQ ID NO: 1 can be made, and modification to the amino acid sequence shown in SEQ ID NO: 3, 5 or 27 is particularly preferred. In addition, for example, at least one substitution selected from R24Q, Q27E, K79T, R82S and K112E in the light chain variable region constituting the humanized anti-glypican 3 antibody shown in SEQ ID NO: 7 can be made, and modification to the amino acid sequence shown in SEQ ID NO: 9, 11, 28 or 29 is particularly preferred. In addition, the modification that decreases the pI value also include substitution of one or more amino acid residues in the heavy chain constant region designated by H268, H274, H355, H356, H358 and H419 according to the Kabat numbering. Preferred examples of substitution is at least one modification in the heavy chain constant region shown in SEQ ID NO: 31 includes, for example, substitution of H that is the 151st amino acid residue with Q, substitution of K that is the 157th amino acid residue with Q, substitution of R that is the 238th amino acid residue with Q, substitution of D that is the 239th amino acid residue with E, substitution of L that is the 241st amino acid residue with M, and substitution of Q that is the 302nd amino acid residue with E. The above substitution resulted in a chimera of the constant region of IgG1 and the constant region of IgG4 of a human antibody. Thus such a substitution allows for preparation of a modified antibody with a desired pI value without affecting the immunogenicity of the antibody.

There are no particular limitations in the present invention on the number of amino acid residues subjected to modification; when, for example, the variable region of the antibody is being modified, preferably the fewest number of amino acid residues necessary to achieve the desired modulated plasma kinetics is modified, in order to avoid lowering the binding activity to antigen and in order to avoid raising the immunogenicity. It may also be suitable to implement a suitable combination with an amino acid residue modification that causes a decline in immunogenicity and/or an amino acid residue modification that causes an increase in the binding activity to antigen.

Known techniques can be used to measure the antigen binding activity of the antibody. For example, enzyme-linked immunosorbent assay (ELISA), enzyme immunoassay (EIA), radioimmunoassay (RIA), or a fluorescent immunoassay can be used. These methods are described in a common textbook, *Antibodies: A Laboratory Manual*, Ed Harlow and David Lane, Cold Spring Harbor laboratory, 1988.

The methods described on pages 359 to 420 of *Antibodies: A Laboratory Manual* (Ed Harlow and David Lane, Cold Spring Harbor laboratory, 1988) are examples of methods that can be used to measure an antibody's binding activity to cells. The binding activity may be evaluated based on a FACS (fluorescence activated cell sorting) or ELISA principle using the cells as an antigen. In the ELISA format, an antibody's binding activity to cells is quantitatively evaluated by comparing the signal levels generated by an enzymatic reaction. Thus, a test antibody is added to an ELISA plate on which the over-expressing cells have been immobilized and the antibody bound to the cells is detected by an enzyme-labeled antibody that recognizes the test antibody. In the case of FACS, the binding activity to cells can be compared by constructing a dilution series with the test antibody and comparing the antibody binding titers for the over-expressing cells.

Binding between an antigen expressed on the surface of cells suspended in a buffer and not anchored on a carrier (such as an ELISA plate) and an antibody for this antigen can be measured by the FACS format. Flow cytometers used in such measurements may include FACSCanto™ II, FACSAria™, FACSArray™, FACSVantage™ SE, and FACSCalibur™ (all from BD Bioscience) and the EPICS ALTRA HyPerSort, Cytomics FC 500, EPICS XL-MCL ADC, EPICS XL ADC, and Cell Lab Quanta/Cell Lab Quanta SC (all from Beckman Coulter).

In an example of a suitable method for measuring the binding activity of a test anti-glypican 3 antibody to an antigen, the test antibody is reacted with a cell expressing glypican 3; the cells are stained with an FITC-labeled secondary antibody that recognizes the test antibody; the fluorescent intensity is measured with FACSCalibur (BD); and analyzed using CELL QUEST software (BD). According to this method, the test antibody bound to the glypican 3 on the surface of glypican 3-expressing cells is stained by FITC-labeled secondary antibody that specifically recognizes the test antibody, and the fluorescent intensity if measured by FACSCalibur, then the geometric mean value (test geo-mean value) obtained by analysis of the resulting fluorescent intensity is compared with the control geo-mean value obtained from a control antibody using the CELL QUEST software. The computational formulas that yield the geo-mean value (geometric mean) are described in the CELL QUEST Software User's Guide (BD Biosciences).

In order to avoid increasing the in vivo immunogenicity for the human receiving the antibody, the modified amino acid sequence is preferably, but not limited to, a human sequence (sequence seen in a naturally occurring antibody of human origin). In addition, mutations can be suitably introduced at locations other than the modifications introduced to change the isoelectric point, so as to modify each of the plurality of FRs (FR1, FR2, FR3, FR4) into a human sequence. A method that converts each of the FRs into a human sequence in this manner is reported by Ono K., Ohtomo T., Yoshida K., Yoshimura Y., Kawai S., Koishihara Y., Ozaki S., Kosaka M., and Tsuchiya M., The humanized anti-HM1.24 antibody effectively kills multiple myeloma cells by human effector cell-mediated cytotoxicity, *Mol. Immunol.* (1999) 36(6), 387-395. In addition, in order to change the isoelectric point of the antibody, each of the FR sequence may be converted to another human FR sequence in order to change the charge of a particular FR (for example, FR3 may be exchanged with another human FR in order to lower the isoelectric point of the antibody). Such a humanization method is reported in Dall'Acqua W. F., Damschroder M. M., Zhang J., Woods R. M., Widjaja L., Yu J., and Wu H., Antibody humanization by framework shuffling, *Methods* (2005) 36(1), 43-60.

In those instances where the desired modulated plasma kinetics are not achieved by a modest modification of the surface charge, an antibody (e.g. anti-glypican 3 antibody) exhibiting the desired modulated plasma kinetics can be suitably obtained by the repetitive execution of surface charge modification and evaluation of plasma kinetics.

The plasma kinetics of chimeric EP5C7.g4, a chimeric anti-E, P-selectin antibody (IgG4), have been compared with those of HuEP5C7.g4, a humanized antibody (IgG4), and the two were shown to have the same plasma kinetics in the rhesus monkey (He X. Y., Xu Z., Melrose J., Mullowney A., Vasquez M., Queen C., Vexler V., Klingbeil C., Co M. S., and Berg E. L., Humanization and pharmacokinetics of a monoclonal antibody with specificity for both E- and P-selectin, *J. Immunol.* (1998), 160(2), 1029-35). In additison, the plasma kinetics of ch5d8, a chimeric anti-CD154 antibody, have been compared with those of the humanized antibody Hu5c8 in cynomolgus monkey and the two were shown to have the same plasma kinetics (Gobburu J. V., Tenhoor C., Rogge M. C., Frazier D. E. Jr., Thomas D., Benjamin C., Hess D. M., and Jusko W. J., Pharmacokinetics/dynamics of 5c8, a monoclonal antibody to CD154 (CD40 ligand) suppression of an immune response in monkeys, *J. Pharmacol. Exp. Ther.* (1998) 286(2), 925-30). The plasma kinetics of the chimeric antibody cCC49 were shown to be the same as those of the humanized antibody HuCC49 in mice (Kashmiri S. V., Shu L., Padlan E. A., Milenic D. E., Schlom J., and Hand P. H., Generation, characterization, and in vivo studies of humanized anticarcinoma antibody CC49, *Hybridoma* (1995) 14(5), 461-73). The plasma kinetics and distribution of mouse antibody and humanized antibody were shown to be the same in evaluations in mice (Graves S. S., Goshorn S. C., Stone D. M., Axworthy D. B., Reno J. M., Bottino B., Searle S., Henry A., Pedersen J., Rees A. R., and Libby R. T., Molecular modeling and preclinical evaluation of the humanized NR-LU-13 antibody, *Clin. Cancer Res.* (1999) 5(4), 899-908; Couto J. R., Blank E. W., Peterson J. A., and Ceriani R. L., Anti-BA46 monoclonal antibody Mc3: humanization using a novel positional consensus and in vivo and in vitro characterization, *Cancer Res.* (1995) 55(8) 1717-22). It is thought that the plasma kinetics and distribution of the chimeric antibodies and humanized antibodies are the same due to the fact that the murine Fc and human Fc are both cross-reactive with the murine FcRn. As shown by these examples, the plasma kinetics are the same between chimeric antibodies and humanized antibodies that have the same CDR. This means that humanization by the known methods provided in Ghetie V., Popov S., Borvak J., Radu C., Matesoi D., Medesan C., Ober R. J., and Ward E. S., Increasing the serum persistence of an IgG fragment by random mutagenesis, *Nat. Biotechnol.* (1997) 15(7), 637-40) and so forth, may provide the same plasma kinetics as the chimeric antibody, and thus a humanized antibody having modulated plasma kinetics therefore cannot be prepared by the known methods.

In contrast, when a chimeric antibody (e.g. chimeric anti-glypican 3 antibody) is humanized according to the method of the present invention, the pI of the antibody is modified by modification to an amino acid residue that can be exposed on the surface of the chimeric antibody to construct a humanized antibody (e.g. humanized anti-glypican 3 antibody) that exhibits modulated plasma kinetics (i.e., an increase or decrease in its plasma half-life) in comparison to the original chimeric antibody. For the purpose of modulating the plasma kinetics, the modification of amino acid that can be exposed on the surface of the humanized antibody (e.g. humanized anti-glypican 3 antibody) may be carried out at the same time as the humanization of the antibody, or the pI of the humanized antibody may be modified by modification of surface-exposed amino acid starting from the humanized antibody (e.g. humanized anti-glypican 3 antibody).

It has been established that trastuzumab, bevacizumab, and pertuzumab, which are three humanized antibodies that have been humanized using the same human antibody FR sequence, have about the same plasma kinetics (Adams C. W., Allison D. E., Flagella K., Presta L., Clarke J., Dybdal N., McKeever K., and Sliwkowski M. X., Humanization of a recombinant monoclonal antibody to produce a therapeutic HER dimerization inhibitor, pertuzumab, *Cancer Immunol Immunother*. (2006) 55(6), 717-27). Thus, the plasma kinetics are about the same when antibodies are humanization using the same FR sequence. According to the method of the present invention, the plasma kinetics of the antibody (e.g. anti-glypican 3 antibody) can be modulated in the humanization step where the pI of the antibody (e.g. anti-glypican 3 antibody) is modified by adding a modification to an amino acid residue that can be exposed on the surface of the antibody.

The method of the present invention can also be applied to human antibodies. A human antibody (e.g. human anti-glypican 3 antibody) having modulated plasma kinetics relative to the plasma kinetics of the initially prepared human antibody (i.e., an increase or decrease in the former's plasma half-life) can be constructed by modification of the pI of a human antibody (e.g. human anti-glypican 3 antibody) by adding a modification to an amino acid residue that can be exposed on the surface of a human antibody constructed from a human antibody library, a human antibody-producing mouse, and so forth.

The plasma half-life of an antibody is increased by lowering the pI value of the antibody. In contrast, it is known that the plasma half-life is decreased and the antibody's tissue translocation characteristics are improved by raising the antibody's pI value (Vaisitti T., Deaglio S., and Malavasi F., Cationization of monoclonal antibodies: another step towards the "magic bullet"?, *J. Biol. Regul Homoest. Agents* (2005) 19(3-4), 105-12; Pardridge W. M., Buciak J., Yang J., and Wu D., Enhanced endocytosis in cultured human breast carcinoma cells and in vivo biodistribution in rats of a humanized monoclonal antibody after cationization of the protein, *J Pharmacol Exp Ther*. (1998) 286(1), 548-54). However, due to fact that such an antibody exhibits an increased immunogenicity and an enhanced internalization into the cell, additional improvements are required for application as an antibody that exhibits anti-cancer effect via a mechanism such as a cytotoxic activity, because internalization into the cell is a hindrance to the manifestation of its cytotoxic activity, such as ADCC activity, CDC activity, and so forth. Thus, with regard to antibody that exhibits anti-cancer effect via a mechanism such as a cytotoxic activity, where internalization into the cell is a hindrance to the manifestation of its cytotoxic activity, such as ADCC activity, CDC activity, and so forth, it had not been determined whether an increase in the pI value of an antibody or a reduction in the pI value of an antibody causes enhancement of the tumor-inhibiting effect. In the present invention, modified humanized anti-glypican 3 antibody with a reduced pI value and modified humanized anti-glypican 3 antibody with an increased pI value were constructed, and then the question of which modification has the higher tumor-inhibiting activity was examined by subjecting both antibodies to comparative testing of the antitumor effect. As a result, it was surprisingly shown that the humanized anti-glypican 3 antibody with the reduced pI value exhibited the better effect against liver cancer.

The term "anti-glypican 3 antibody" as used herein encompasses anti-glypican 3 antibody obtained by subjecting anti-glypican 3 antibody that has already been subjected to amino acid residue charge modification as described above, to additional modification of its amino acid sequence, for example, by subjecting the amino acid residues constituting this anti-glypican 3 antibody to substitution, deletion, addition, and/or insertion. In addition, the term "anti-glypican 3 antibody" as used herein also encompasses anti-glypican 3 antibody obtained starting from anti-glypican 3 antibody that has already been subjected to amino acid residue substitution, deletion, addition, and/or insertion, or to modification of its amino acid sequence by, for example, chimerization, humanization, and so forth, and additionally subjecting the amino acid residues constituting this anti-glypican 3 antibody to charge modification.

A preferred example of a modification whose goal is to improve the characteristics of the antibody (e.g. anti-glypican 3 antibody) of the present invention is a modification whose goal is to raise the stability of the antibody (referred to below as a stability modification). In aqueous solution, the antibody equilibrates between two states, its native state and an inactive denatured state. The stability of the native state, as shown by the second law of thermodynamics ($\Delta G=\Delta H-T\Delta S$), depends on the Gibbs free energy change $\Delta G$ of the system and the balance between the components of $\Delta G$, i.e., the enthalpy change $\Delta H$ (attributable to changes in, for example, hydrophobic interactions and hydrogen bond in the polypeptide chain) and the entropy change $\Delta S$ (attributable to changes in solvation and the degrees of freedom in the three-dimensional structure). A positive value for $\Delta G$ indicates that the native state of the protein is more stable than the protein's denatured state, and the stability of the native state of the protein rises as $\Delta G$ assumes larger positive values. The forces contributing to this stability must be disrupted in order to denature the protein. For example, exposing the protein solution to high temperatures results in an increase in the degrees of freedom in the three-dimensional structure and a weakening of the factors that contribute to protein stabilization, causing a thermal denaturation of the protein. In this case the $-T\Delta S$ term governs the denaturation. The $\Delta H$ of the unfolding due to thermal denaturation of the protein can be directly measured by differential scanning calorimetry (DSC), as is specifically described in the examples provided herein. The DSC curve for the protein thermal denaturation process takes the form of an endothermic peak that frames a temperature, known as the denaturation midpoint (Tm), that is characteristic of the test protein. The denaturation enthalpy change is obtained by integration of this peak. The Tm value is generally an indicator of thermal stability. The change in the heat capacity ($\Delta Cp$) can also be measured during thermal denaturation of the protein by DSC. The change in the heat capacity that occurs during denaturation is caused mainly by hydration that occurs when amino acid residues that are not exposed on the molecule's surface when the protein is in its native state become exposed to solvent molecules during the course of protein denaturation.

As described above, amino acid residue "modification" in the method of the present invention specifically encompasses, inter alia, substitution of an original amino acid residue with another amino acid residue, deletion of an original amino acid residue, and the addition of a new amino acid residue. The substitution of an original amino acid residue with another amino acid residue is preferred. Thus, modification by amino acid substitution is preferably used in the present invention when a modification of antibody stability is sought. The. Tm value of the antibody (e.g. anti-glypican 3 antibody) is increased as a result of the execution of the stability modification on the amino acid residues constituting the antibody. Thus, the Tm value is suitably used as an indicator of the stability modification of the antibody (e.g. anti-glypican 3 antibody) has occurred.

In order to carry out the aforementioned "stability modification" with the anti-glypican 3 antibody of the present invention, modification is preferably carried out, for example, on at least one amino acid residue selected from the amino acid residues at positions 37, 40, 48, and 51 in the humanized anti-glypican 3 antibody heavy chain variable region shown in SEQ ID NO: 1. In addition, modification is preferably carried out on at least one amino acid residue selected from the amino acid residues at positions 2, 25, 42, 48, 50, 83, and 84 in the humanized anti-glypican 3 antibody light chain variable region shown in SEQ ID NO: 7. The amino acid residues other than the aforementioned amino acid residues on which stability modification has been carried out, need not be modified as long as the desired Tm value has been obtained; however, it can be appropriate to carry out a suitable modification thereon so as to provide a Tm value that is about the same as or higher than the Tm value of the humanized anti-glypican 3 antibody subjected to the modification.

The stability modification can be carried out by randomly modifying amino acid residues constituting the antibody (e.g. humanized anti-glypican 3 antibody) subjected to the modification. In addition, stability modification can also be carried out by replacing a portion of the amino acid sequence constituting the humanized antibody (e.g. antibody anti-glypican 3 antibody) subjected to the modification, with an amino acid sequence found in an antibody that already has a high Tm value and that corresponds—from the standpoint of the correlation of antibody three-dimensional structure—with said portion of the amino acid sequence constituting the humanized antibody (e.g. humanized anti-glypican 3 antibody) subjected to the modification. There are no limitations on the position of the amino acid residue or residues undergoing substitution; however, amino acid residue or residues in the FR are preferably modified. Amino acid residue modification can even be carried out as appropriate in the CDR region as long as there is no associated reduction in the binding activity for the antigen. In addition, the number of amino acid residues subjected to modification is not particularly limited, and modification can even be implemented by replacing a particular segment of the FR with a desired segment. With regard to such segments, all of the segments within the FR (FR1, FR2, FR3 FR4) can be modified, or one or more of the segments modification may be combined.

The FR2 of the heavy chain or the light chain is a preferred example in those instances where a segment of the FR is modified. A preferred specific example in this regard is an amino acid residue modification in which humanized anti-glypican 3 antibody heavy chain FR2 in the VH1b subclass (shown in SEQ ID NO: 1) is modified to the VH4 subclass, i.e., V37I (valine at position 37 is replaced by isoleucine) as well as A40P, M48I, and L51I modifications. Other preferred specific examples are a modification of humanized anti-glypican 3 antibody light chain FR2 region in the VK2 subclass (shown in SEQ ID NO: 7) to the VK3 subclass, i.e., L42Q, S48A, and Q50R modifications. Also preferred is V2I modification, which corresponds to modification to a germline sequence for FR1.

The execution of substitution, deletion, addition, and/or insertion with respect to the amino acid residues constituting the antibody (e.g. anti-glypican 3 antibody) and the modification of the amino acid sequence by, for example, chimerization and humanization, can be carried out as appropriate by any method known to those skilled in the art. The execution of substitution, deletion, addition, and/or insertion with respect to the amino acid residues constituting the antibody's variable region and constant region can similarly be carried out as appropriate during construction of the antibody (e.g. anti-glypican 3 antibody) of the present invention as a recombinant antibody.

Any antibodes of animal origin, e.g., mouse antibody, human antibody, rat antibody, rabbit antibody, goat antibody, camel antibody may preferably be used as the antibody (e.g. anti-glypican 3 antibody) of the present invention. Also preferred for use is a modified antibody (e.g. anti-glypican 3 antibody) as obtained by substitution in the amino acid sequence of chimeric antibody and humanized antibody. Also preferred for use are antibody modifications in which any of various molecules is attached.

"Chimeric antibody" refers to an antibody constructed by combining sequences originating from different animals. Suitable examples in this regard are antibodies constructed from the heavy chain and light chain variable regions from mouse antibody and the heavy chain and light chain constant regions from human antibody. Methods for constructing chimeric antibodies are known. For example, recombinant DNA is generated by the in-frame fusion of DNA encoding a mouse antibody variable region and DNA encoding a human antibody constant region, and can be incorporated into a conventional expression vector. A host cell transfected or transformed with this vector is cultured and the chimeric antibody can be prepared or isolated from a culture medium by appropriate means.

Humanized antibodies are also known as reshaped human antibodies. These are antibodies in which a complementarity-determining region (CDR) from an antibody isolated from a nonhuman mammal, such as mouse, is ligated to a framework region (FR) from a human antibody. The DNA sequence encoding the humanized antibody can be synthesized by an overlapping PCR reaction using a plurality of oligonucleotides as primers. The starting materials and procedures for overlapping PCR reactions are described, for example, in WO 98/13388 and elsewhere. DNA encoding the variable region of a humanized antibody of the present invention is obtained by overlapping PCR from a plurality of oligonucleotides constructed so as to have nucleotide sequences that overlap with each other, which is in turn ligated with DNA encoding a human antibody constant region so as to form an in-frame codon sequence. The DNA ligated as described is then operably inserted into an expression vector followed by transfection into a host.

Methods for identifying CDRs are known (Kabat et al., Sequences of Proteins of Immunological Interest (1987), National Institute of Health, Bethesda, Md.; Chothia et al., *Nature* (1989) 342, 877). General genetic recombination procedures therefor are also known (refer to EP 125023 A and WO 96/02576). Once a CDR from an antibody of a nonhuman animal, for example, a murine antibody, has been determined, these known methods can be used to construct DNA encoding a recombinant antibody in which the CDR and FR from a human antibody are ligated. The human antibody FRs ligated with the CDR are selected in such a manner that the CDR forms a high-quality antigen binding site. As necessary, an amino acid residue or residues in the antibody variable regions FRs may be modified as appropriate so as to enable the CDR of the reshaped human antibody to form a suitable antigen binding site (Sato et al., *Cancer Res*. (1993) 53, 851-6). The amino acid residues in the FRs subjected to modification may include residues that directly bind to the antigen by noncovalent bonds (Amit et al., *Science* (1986) 233, 747-53), residues that influence or act on the CDR structure (Chothia et al., *J. Mol. Biol*. (1987) 196, 901-17), and residues related to VH-VL (heavy chain variable region-light chain variable region) interactions (EP 239400 B).

The humanized antibody encoded by the DNA is produced by the host cell that has been transformed or transfected by the generally used expression vector into which the DNA has been inserted and is isolated from the culture medium yielded by the culture of the host cell.

When the antibody of the present invention is a chimeric antibody, humanized antibody or human antibody, a constant region of human antibody origin is preferably used as the constant region of the antibody. For example, when the anti-glypican 3 antibody of the present invention is a chimeric anti-glypican 3 antibody, humanized anti-glypican 3 antibody or human anti-glypican 3 antibody, a constant region of human antibody origin is preferably used as the constant region of the anti-glypican 3 antibody. For example, Cγ1, Cγ2, Cγ3, and Cγ4 are each suitable for use as the heavy chain constant region, while Cκ and Cλ are each suitable for use as the light chain constant region. In addition, the human antibody constant region can be modified as appropriate in order to improve the antibody (e.g. anti-glypican 3 antibody) or improve the stability of its production. Chimeric antibody (e.g. chimeric anti-glypican 3 antibody) of the present invention suitably comprises a variable region from an antibody of a nonhuman mammal and a constant region from a human antibody. On the other hand, the humanized antibody preferably comprises a CDR from an antibody of a nonhuman mammal and a constant region and FR from a human antibody. For example, a humanized anti-glypican 3 antibody preferably comprises a CDR from an anti-glypican 3 antibody of a nonhuman mammal and a constant region and FR from a human antibody. The human antibody suitably comprises a CDR from an antibody of human origin and a constant region and FR from a human antibody. For example, the human anti-glypican 3 antibody suitably comprises a CDR from an anti-glypican 3 antibody of human origin and a constant region and FR from a human antibody. The human antibody constant region is composed of an amino acid sequence that is characteristic of the particular isotype, i.e., IgG (IgG1, IgG2, IgG3, IgG4), IgM, IgA, IgD, and IgE. The constant region from antibody belonging to any of these isotypes is suitably used as the constant region of the humanized antibody (e.g. anti-glypican 3 antibody) of the present invention. The use of the constant region from human IgG is preferred, but not limited. There are also no particular limitations on the human antibody FR used as the FR of the humanized antibody (e.g. humanized anti-glypican 3 antibody) or human antibody (e.g. human anti-glypican 3 antibody), and the FR from antibody belonging to any isotype is suitably used.

With the aim of lowering the immunogenicity, all or a portion of the amino acid residues constituting the FR can also be replaced by germline sequences using the method described in Ono K. et al., loc. cit., or a similar method. Based on the rational prediction that germline sequences will have a low immunogenicity, the amino acid sequence constituting the FR of the humanized antibody may be compared, by alignment, with germline amino acid sequences (Abhinandan K. R. and Martin C. R., *J. Mol. Biol.* (2007) 369, 852-862). The amino acid residues of the humanized antibody FR that differ in this comparison can be replaced, within a range that does not impair the antigen binding characteristics, with amino acid residues from a germline sequence. The following are specific examples for the amino acid residues constituting the heavy chain variable region shown in SEQ ID NO: 1: modification that replaces the L at position 70 with I, modification that replaces the T at position 87 with R, and modification that replaces the T at position 97 with A. In addition, a modification that replaces the S at position 25 with A is an example for the amino acid residues constituting the light chain variable region shown in SEQ ID NO: 7.

With regard to the variable region and constant region of the modified chimeric antibody, humanized antibody, and human antibody of the present invention, deletion, substitution, insertion, and/or addition can be carried out as appropriate at one or more of the amino acids constituting the variable region and/or constant region of the antibody that was subjected to modification, insofar as binding specificity for the antigen is exhibited. In particular, the variable region and constant region of the modified chimeric anti-glypican 3 antibody, humanized anti-glypican 3 antibody, and anti-glypican 3 human antibody of the present invention, deletion, substitution, insertion, and/or addition can be carried out as appropriate at one or more of the amino acids constituting the variable region and/or constant region of the anti-glypican 3 antibody that was subjected to modification, insofar as binding specificity for the antigen glypican 3 molecule is exhibited.

Because chimeric anti-glypican 3 antibodies utilizing human-derived sequences, humanized anti-glypican 3 antibodies, and human anti-glypican 3 antibodies have a reduced immunogenicity in the human body, they are believed to be useful for application as therapeutic antibodies that are administered to humans, for example, with a therapeutic objective.

Known sequences can be used in the method of the present invention for the sequences that encode the antibody heavy chain and light chain for introduction of mutation. In addition, novel antibody gene sequences can be obtained by methods known to those skilled in the art. For example, genes can be suitably obtained from antibody libraries. Moreover, genes can also be obtained by cloning using known procedures, e.g., RT-PCR using as template mRNA from a monoclonal antibody-producing hybridoma.

Numerous antibody libraries are already known within the sphere of antibody libraries. Moreover, as methods for constructing antibody libraries are also known, those skilled in the art will be able to obtain or construct relevant antibody libraries. Examples of suitable antibody libraries are the antibody phage libraries disclosed in the literature, for example, Clackson et al., *Nature* (1991) 352, 624-8; Marks et al., *J. Mol. Biol.* (1991) 222, 581-97; Waterhouses et al., *Nucleic Acids Res.* (1993) 21, 2265-6; Griffiths et al., *EMBO J.* (1994) 13, 3245-60; Vaughan et al., *Nature Biotechnology* (1996) 14, 309-14; and Japanese Patent Application Laid-open No. 2008-504970. A method of constructing a library in eukaryotic cells (WO 95/15393) and known methods such as ribosome display and so forth are also suitably used. Technology for obtaining human antibodies by panning techniques using a human antibody library as the starting material is also known to those skilled in the art. Thus, single-chain antibody (scFv), comprising the variable regions of human antibody heavy and light chains fused in-frame, is expressed on a phage surface using phage display techniques. Genes encoding antigen-binding scFv are isolated from this phage by selecting for phage that binds to the antigen. Identification of the sequence of such genes enables the determination of the DNA sequence that encodes the heavy and light chain variable regions of a human anti-glypican 3 antibody that binds to the antigen glypican 3. Human anti-glypican 3 antibody is suitably prepared by inserting the antibody gene having this sequence in a suitable expression vector and allowing for expression in a suitable host cell as described below. Such methods are well-known in the art and include those disclosed in WO 92/01047, WO 92/20791, WO 93/06213, WO 93/11236, WO 93/19172, WO 95/01438, and WO 95/15388.

Known technologies can be used to obtain an antibody-encoding gene from a hybridoma that produces the antibody, particularly to obtain an anti-glypican 3 antibody-encoding gene from a hybridoma that produces anti-glypican 3 monoclonal antibody. Briefly, an animal is immunized with glypican 3 (the desired sensitizing antigen) using a standard immunization technique and the immunocytes obtained from the animal are subjected to cell fusion with known parent cells by a standard cell fusion technique, which is described in detail below. Using standard screening techniques, the monoclonal antibody-producing cells (hybridomas) are screened, and cDNA for the variable region (V region) of anti-glypican 3 antibody can be synthesized with reverse transcriptase using the mRNA isolated from the selected hybridoma as a template. An anti-glypican 3 antibody gene is suitably prepared by the in-frame fusion of this cDNA with DNA encoding the desired antibody constant region (C region).

Specific examples are provided in the following, but the present invention is not limited to these examples. The sensitizing antigen used to generate the antibody of the present invention may be the complete immunogenic antigen or may be an incomplete antigen, including, for example, a nonimmunogenic hapten. For example, the full length glypican 3 protein or a partial polypeptide or peptide thereof can be suitably used. The soluble GPC3 core polypeptide shown in SEQ ID NO: 13 is a preferred example. Otherwise, the use of substances comprising polysaccharide, nucleic acid, lipid, and so forth as an antigen is also known. Antigen to which the anti-glypican 3 antibody of the present invention binds is not particularly limited to the embodiments described above. Antigen production is suitably carried out by methods known to those skilled in the art. For example, a method using baculovirus (for example, WO 98/46777 and so forth) can be suitably used. When the antigen has a low immunogenicity, the animal can suitably be immunized with such an antigen attached to a very large immunogenic molecule, such as albumin. When the sensitizing antigen is a molecule that spans the cell membrane, such as glypican 3, a polypeptide fragment from the molecule's extracellular domain is suitably used as necessary as the sensitizing antigen. Or, a cell expressing such a molecule on the cell surface is suitably used as the sensitizing antigen. In addition, when the sensitizing antigen is an insoluble molecule, solubilization may be effected by attaching the molecule with another water-soluble molecule and the solubilized molecule may then be suitably used as the sensitizing antigen.

Antibody-producing cells (e.g. anti-glypican 3 antibody-producing cells) are suitably obtained by immunizing an animal using a suitable sensitizing antigen as described above. Or, antibody-producing cells (e.g. anti-glypican 3 antibody-producing cells) can be obtained by in vitro immunization of lymphocytes that are capable of producing antibody. Various vertebrates and mammals can be used as the animal to be immunized. In particular, rodents, lagomorphs, and primates can be generally used as the animal to be immunized. The rodents may include mouse, rat, and hamster; the lagomorphs may include rabbit; and the primates may include monkeys such as the cynomolgus monkey, rhesus monkey, hamadryas baboon, and chimpanzee. In addition, transgenic animals that maintain a repertoire of human antibody genes in their genome are also known, and human antibody can be suitably obtained using such animals (WO 96/34096; Mendez et al., *Nat. Genet*. (1997) 15, 146-56). Rather than using such transgenic animals, a desired human antibody that exhibits binding activity to a desired antigen may be suitably obtained by, for example, sensitizing human lymphocytes in vitro with the desired antigen or with cells that express the desired antigen followed by cell fusion with human myeloma cells, for example, U266 (Japanese Patent Publication No. Hei 1-59878). In addition, a desired human antibody (e.g. human anti-glypican 3 antibody) can be suitably obtained by the immunization with a desired of antigen of a transgenic animal that maintains the entire repertoire of human antibody genes in its genome (WO 93/12227, WO 92/03918, WO 94/02602, WO 96/34096, and WO 96/33735).

Immunization of the animal is carried out, for example, by suitable dilution and suspension of the sensitizing antigen in phosphate-buffered saline (PBS), physiological saline solution, and so forth; as necessary emulsification by the admixture of adjuvant; and then intraperitoreal or subcutaneous injection of the sensitizing antigen into the animal. This is followed preferably by several administrations of the sensitizing antigen mixed with Freund's incomplete adjuvant on a 4 to 21 day interval. The production in the immunized animal of antibody against the sensitizing antigen can be measured using known analytical techniques, for example, enzyme-linked immunosorbent assay (ELISA) and flow cytometry (FACS).

A hybridoma can be prepared by fusing an anti-glypican 3 antibody-producing cell obtained from an animal or lymphocyte immunized with the sensitizing antigen of interest, with myeloma cells using a fusing agent conventionally used for cell fusion, e.g., polyethylene glycol (Goding, *Monoclonal Antibodies: Principles and Practice*, Academic Press (1986) 59-103). Hybridoma production can be suitably carried out according to, for example, the method of Milstein et al. (G. Kohler and C. Milstein, *Methods Enzymol. (*1981) 73, 3-46). Culture and proliferation of the hybridoma cells prepared by this method yields monoclonal antibody that is produced by the hybridoma and specifically binds to glypican 3. The binding specificity exhibited by this monoclonal antibody for glypican 3 can be suitably measured by known analytical techniques, such as immunoprecipitation, radioimmunoassay (RIA), enzyme-linked immunosorbent assay (ELISA), flow cytometry (FACS), and so forth. As necessary, a hybridoma that produces anti-glypican 3 antibody with the desired specificity, affinity, or activity may then be suitably subcloned by, for example, limiting dilution, and the monoclonal antibody produced by this hybridoma can be isolated.

The gene encoding the selected antibody can then be cloned from the aforementioned hybridoma or antibody-producing cell (e.g., sensitized lymphocyte) using a probe capable of specifically binding to the gene (for example, oligonucleotide complementary to the sequence encoding the antibody's constant region). Cloning can also be carried out by RT-PCR using mRNA isolated from the hybridoma or antibody-producing cell (e.g., sensitized lymphocyte) as a template. Immunoglobulins are divided into 5 different classes, i.e., IgA, IgD, IgE, IgG, and IgM, based on differences in their structure and function. Furthermore, the individual classes are divided into several subclasses (isotypes) (for example, IgG1, IgG2, IgG3, and IgG4; IgA1 and IgA2; and so forth). The antibody of the present invention may originate from antibody belonging to any of these classes and subclasses and is not particularly limited to any class or subclass; however, antibody belonging to the IgG class is particularly preferred.

Genes encoding the amino acid sequences constituting the heavy chain and light chain of the antibody (e.g. anti-glypican 3 antibody) can be modified as appropriate by the techniques of genetic engineering. For example, a recombinant antibody that has been subjected to artificial modification with the aim of, for example, reducing the xeno-immunogenicity against humans (e.g., chimeric antibody such as chimeric anti-glypican 3 antibody, humanized antibody such as humanized anti-glypican 3 antibody, and so forth), can be suitably produced by modification of the nucleic acid residues that encode the amino acid sequence constituting the antibody, for example, a mouse antibody, rat antibody, rabbit antibody, hamster antibody, sheep antibody, camel antibody, and so forth. A chimeric antibody is an antibody constituted of the heavy chain and light chain variable regions of antibody originating from a nonhuman mammal such as mouse, and the heavy chain and light chain constant regions of human antibody. A chimeric antibody can be obtained as follows: DNA encoding the variable region of a mouse-originated antibody is ligated with DNA encoding the constant region of a human antibody and inserted into an expression vector, and the resulting recombinant vector is introduced into a host and allowed for expression. Humanized antibody is also known as reshaped human antibody and is an antibody in which the complementarity-determining region (CDR) of an antibody (e.g. anti-glypican 3 antibody) isolated from a nonhuman mammal such as mouse is ligated with a human antibody framework region so as to form an in-frame codon sequence. The DNA sequence encoding a humanized antibody can be synthesized by an overlapping PCR reaction using a plurality of oligonucleotides as templates. The starting materials and procedures for the overlapping PCR reaction are described in, for example, WO 98/13388 and elsewhere.

The DNA encoding the variable region of the recombinant antibody (e.g. recombinant anti-glypican 3 antibody) of the present invention is obtained by overlapping PCR from a plurality of oligonucleotides constructed so as to have nucleotide sequences that overlap with each other, which is in turn ligated with DNA encoding human antibody constant region so as to form an in-frame codon sequence. The DNA ligated in this manner is then inserted in an operable manner into an expression vector, and introduced into a host. The antibody (e.g. anti-glypican 3 antibody) encoded by the DNA is expressed by culturing the host. The expressed antibody (e.g. anti-glypican 3 antibody) is isolate by purifying from the host culture medium (EP 239400, WO 96/02576, and so forth). The FRs of the humanized antibody (e.g. anti-glypican 3 antibody) ligated with CDR are selected in such a manner that the complementarity-determining region forms a high-quality antigen-binding site for the antigen. As necessary, the amino acid sequence may be modified by suitable substitution of the amino acid residues constituting the antibody variable region FRs, so as to enable the complementarity-determining region of reshaped antibody to form a suitable antigen-binding site for the antigen (K. Sato et al., *Cancer Res.* (1993) 53, 851-856)

In addition to modifications related to humanization as discussed above, further modifications can be introduced, for example, to improve the biochemical characteristics of the antibody, e.g., the binding activity with the antigen recognized by the antibody (e.g. anti-glypican 3 antibody). Modifications in the context of the present invention can be suitably carried out by known methods such as site-specific mutagenesis (refer, for example, to Kunkel, *Proc. Natl. Acad. Sci. USA* (1985) 82, 488), PCR mutation, cassette mutation, and so forth. The amino acid sequence of the modified antibody with improved biochemical characteristics generally has at least 70%, more preferably at least 80%, and even more preferably at least 90% (for example, at least 95%, 97%, 98%, 99%, and so forth) identity and/or similarity with the amino acid sequence constituting the antibody subjected to the modification (that is, the antibody on which the modified antibody is based). As used herein, the sequence identity and/or similarity refers to the proportion of amino acid residues that are identical (identical residues) or similar (amino acid residues classified into the same group based on the general characteristics of the amino acid side chain) after aligning the sequences and inserting gaps as necessary in such a manner that the sequence identity assumes a maximum. The naturally occurring amino acid residues can generally be classified into the following groups based on the properties of the side chain: (1) hydrophobic: alanine, isoleucine, valine, methionine, and leucine; (2) neutral hydrophilic: asparagine, glutamine, cysteine, threonine, and serine; (3) acidic: aspartic acid and glutamic acid; (4) basic: arginine, histidine, and lysine; (5) residues that affect chain orientation: glycine and proline; and (6) aromatic: tyrosine, tryptophan, and phenylalanine.

A specific suitable embodiment of a modification for enhancing antibody function includes an improvement in the cytotoxicity exhibited by the antibody, such as humanized anti-glypican 3 antibody. Preferred examples of cytotoxicity are antibody-dependent cell-mediated cytotoxicity (ADCC) and complement-dependent cytotoxicity (CDC). In the present invention, CDC activity denotes cytotoxicity due to the complement system, while ADCC refers to an activity of damaging the target cell when a specific antibody attaches to a cell surface antigen on the target cell and an Fcγ receptor-bearing cell (e.g., an immunocyte) binds to the Fc portion of the antibody through the Fcγ receptor. Whether a test antibody has ADCC activity or has CDC activity can be measured by known methods (for example, *Current Protocols in Immunology*, Chapter 7, Immunologic studies in humans. Editor, John E. Coligan et al., John Wiley & Sons, Inc., (1993)).

In specific terms, effector cells, a complement solution, and target cells are first prepared.

(1) Preparation of Effector Cells

The spleen is isolated from, for example, CBA/N mouse, and the spleen cells are separated on RPMI1640 medium (Invitrogen). After washing with the same medium containing 10% fetal bovine serum (FBS, HyClone) the cell concentration is adjusted to $5\times10^6$ cells/mL to prepare the effector cells.

(2) Preparation of Complement Solution

The complement solution can be prepared by a 10× dilution of Baby Rabbit Complement (CEDARLANE) with 10% FBS-containing medium (Invitrogen).

(3) Preparation of Target Cells

Cells that express an antigen protein to which the test antibody binds are cultured with 0.2 mCi $^{51}$Cr sodium chromate (GE Healthcare Bioscience) for 1 hour at 37° C. in DMEM medium containing 10% FBS in order to radiolabel the target cells. The following, inter alia, can be used as the cells that express an antigen protein to which the test antibody binds: cells transformed with a gene that encodes an antigen protein to which the test antibody binds, ovarian cancer cells, prostate cancer cells, breast cancer cells, uterine cancer cells, liver cancer cells, lung cancer cells, pancreatic cancer cells, kidney cancer cells, bladder cancer cells, and colon cancer cells. After radiolabeling, the cells are washed three times with RPMI1640 medium containing 10% FBS and the cell concentration is adjusted to $2\times10^5$ cells/mL to prepare the target cells.

The ADCC activity and the CDC activity can be measured by the following methods. In order to measure the ADCC activity, 50 μL of the target cells and 50 μL of the test antibody are added to a 96-well U-bottom plate (Becton Dickinson) and reacted for 15 minutes on ice. To the reaction mixture is added 100 μL effector cells and incubated for 4 hours in a carbon dioxide incubator. A final concentration of test antibody is preferably within the range from 0 to 10 μg/mL. After incubation, 100 μL of the supernatant is recovered and the radioactivity of the supernatant is measured using a gamma counter (COBRA II AUTO-GAMMA, MODEL D5005, Packard Instrument Company). The cytotoxicity can be calculated using the radioactivity according to the following equation:

$$(A-C)/(B-C)\times100$$

wherein A is the radioactivity (cpm) for the sample using the particular test antibody; B is the radioactivity (cpm) of the sample to which 1% NP-40 (Nacalai Tesque) has been added; and C is the radioactivity (cpm) for the sample containing only the target cells.

To measure the CDC activity, 50 μL of the target cells and 50 μL of the test antibody are added to a 96-well flat-bottom plate (Becton Dickinson) and reacted for 15 minutes on ice. To the reaction mixture is added 100 μL complement solution and incubated for 4 hours in a carbon dioxide incubator. A final concentration of test antibody is preferably within the range from 0 to 3 μg/mL. After cultivation, 100 μL of the supernatant is recovered and the radioactivity of the supernatant is measured with a gamma counter. The cytotoxicity can be calculated in the same manner as for measurement of the ADCC activity.

When the cytotoxicity due to an antibody conjugate is to be measured, 50 μL of the target cells and 50 μL of the test antibody conjugate are each added to a 96-well flat-bottom plate (Becton Dickinson) and reacted for 15 minutes on ice. The plate is then incubated for from 1-4 hours in a carbon dioxide incubator. A final test antibody concentration is preferably within the range from 0 to 3 μg/mL. After incubation, 100 μL of the supernatant is recovered and the radioactivity of the supernatant is measured with a gamma counter. The cytotoxicity can be calculated in the same manner as for measurement of the ADCC activity.

The heavy chain and light chain variable regions of the antibody (e.g. anti-glypican 3 antibody) are, as described above, generally composed of 3 CDRs and 4 FRs. The amino acid residues subjected to "modification" in a preferred embodiment of the present invention can be suitably selected, for example, from the amino acid residues constituting the CDRs or FRs. Modification of the amino acid residues constituting the CDRs may in some cases cause a reduction in the antigen binding activity of the antibody (e.g. anti-glypican 3 antibody) involved in the modification. Accordingly, the antibody (e.g. anti-glypican 3 antibody) amino acid residues subjected to "modification" in the present invention are preferably selected from the amino acids residues constituting the FRs, but not limited to. When it is confirmed that modification of amino acid residues located in the CDRs do not cause a reduction in the antigen binding activity of the antibody (e.g. anti-glypican 3 antibody) involved in the modification, then such amino acid residues may be selected for modification.

Those skilled in the art can readily find in a public database, such as the Kabat database, amino acid sequences constituting the antibody variable region FR that actually occur in an organism such as mouse or human.

A preferred embodiment of the present invention provides a humanized antibody (e.g. anti-glypican 3 antibody) having plasma kinetics modulated by the method of the present invention. For example, the humanized antibody (e.g. anti-glypican 3 antibody) is a humanized antibody comprising a complementarity-determining region (CDR) derived from a nonhuman animal, a framework region (FR) of human origin, and a human constant region, wherein at least one amino acid residue that can be exposed on the antibody surface in the CDR or FR has a different charge from that of the amino acid residue in the corresponding position of the CDR or FR of the original antibody and wherein the humanized antibody has plasma kinetics modulated in comparison to the chimeric antibody having the same constant region.

Another preferred embodiment of the present invention provides a human antibody (e.g. human anti-glypican 3 antibody) having plasma kinetics modulated by the method of the present invention. The human antibody, for example, is a human antibody comprising a complementarity-determining region (CDR) of human origin, a framework region (FR) of human origin, and a human constant region, wherein at least one amino acid residue that can be exposed on the antibody surface in the CDR or FR has a different charge from that of the amino acid residue in the corresponding position of the CDR or FR of the original antibody and wherein the human antibody has plasma kinetics modulated in comparison to a chimeric antibody having the same constant region.

The aforementioned human constant region preferably denotes a region comprising a wild-type human Fc region, but a modified Fc can also be suitably used. Such a "modified Fc" may include a modified Fc as prepared by the modification of an amino acid residue constituting the Fc as well as a modified Fc as prepared by a modification of a modification already executed in the Fc moiety. A preferred example of such a modification of a modification is the modification of the nature of the sugar chain modification attached to the Fc portion. One preferred specific example is the "antibody having reduced content of fucose attached to the Fc region" that is specifically disclosed herein as a reference example.

The term "antibody having reduced content of fucose attached to the Fc region" denotes an antibody for which the amount of bound fucose has been significantly reduced in comparison to the control antibody, and preferably fucose is undetectable. Fucose is generally bound to the N-glycoside linked sugar chains that are bound at the two sugar chain-binding sites present in the Fc region of the two heavy chain molecules that form a single antibody molecule. The term "antibody having reduced content of fucose attached to the Fc region" denotes an antibody that, in comparison with the ordinary antibody as the control, has a fucose content no greater than 50%, preferably no greater than 25%, more preferably no greater than 10%, and particularly preferably no greater than 0% of the total sugar chain content of the control antibody. The fucose content can be measured using the analytical procedure provided in the reference examples below. The method for preparing such a fucose-depleted antibody may include the method described in the reference examples of the present invention, as well as a method for producing antibodies with fucosyl transferase-deficient animal cells (*Biotechnol. Bioeng.* (2004) 87(5), 614-22) and a method for preparing antibodies with animal cells in which the complex branched sugar chain modification is modified (*Biotechnol. Bioeng.* (2006) 93(5), 851-61). In addition, suitable examples of preparation methods using non-animal cells as the host cells may include a method for producing antibodies with plant cells (*Nature Biotechnology* (2006) 24, 1591-7) and with yeast cells (*Nature Biotechnology* (2006) 24, 210-5).

A preferred embodiment of the preparation method of the present invention is a method of preparing an antibody (e.g. anti-glypican 3 antibody) having modulated plasma kinetics, comprising (a) modifying a nucleic acid that encodes a polypeptide comprising at least one amino acid residue that can be exposed on the surface of the antibody (e.g. anti-glypican 3 antibody), such that the charge of the amino acid residue(s) is changed; (b) culturing a host cell in such a manner that the nucleic acid modified in the step (a) is expressed; and (c) recovering the antibody (e.g. anti-glypican 3 antibody) from the host cell culture.

In the method of the present invention, the term "modifying a nucleic acid" refers to a modification of the nucleic acid sequence so as to provide a codon that corresponds to the amino acid residue that is introduced by the "modification" of the present invention. More specifically, this term refers to a modification of a nucleic acid that contains a codon that will undergo modification, wherein said modification changes the codon corresponding to the pre-modification amino acid residue to the codon of the amino acid residue that is introduced by the modification. Generally this term means the implementation of a genetic process or mutagenic treatment so as to replace at least one base of the codon-comprising nucleic acid to provide a codon that encodes the target amino acid residue. That is, a codon encoding the amino acid residue subjected to modification is replaced by a codon encoding the amino acid residue that is introduced by the modification. The nucleic acid modification can be suitably carried out by those skilled in the art using known technology, for example, site-specific mutagenesis, PCR mutagenesis, and so forth.

The nucleic acid prepared in the present invention is generally placed (inserted) into a suitable vector and introduced into a host cell. There are no particular limitations on the vector as long as it has the capability to stably maintain the inserted nucleic acid. For example, with reference to the use of *E. coli* as the host, pBluescript vector (Stratagene) is preferred as a cloning vector, although various commercially available vectors can be used. An expression vector is particularly useful in those instances where the vector is used to produce polypeptide of the present invention. There are no particular limitations on the expression vector as long as it can express polypeptide in vitro, in *E. coli*, in cell culture, or within an organism. Preferred examples include pBEST vector (Promega) for in vitro expression, pET vector (Invitrogen) for *E. coli*, pME18S-FL3 vector (GenBank Accession No. AB009864) for cell culture, and pME18S vector (*Mol. Cell Biol.* (1988) 8, 466-472) for an organism. DNA according to the present invention can be inserted into the vector by standard methods, for example, by the ligase reaction utilizing restriction enzyme sites (*Current Protocols in Molecular Biology*, edited by Ausubel et al. (1987) Publish. John Wiley & Sons, sections 11.4-11.11).

There are no particular limitations on the host cell referenced above, and various host cells can be used depending on the purpose. Examples of cells for the expression of polypeptide include bacterial cells (e.g., *Streptococcus, Staphylococcus, E. coli, Streptomyces, Bacillus subtilus*), fungi cells (e.g., yeast, *Aspergillus*), insect cells (e.g., *Drosophila* S2, *Spodoptera* Sf9), animal cells (e.g., CHO, COS, HeLa, C127, 3T3, BHK, HEK293, Bowes melanoma cells), and plant cells. The vector can be introduced into the host cell by known methods, for example, calcium phosphate precipitation, electropulse poration (*Current Protocols in Molecular Biology*, edited by Ausubel et al. (1987) John Wiley & Sons, sections 9.1-9.9), lipofection, and microinjection.

An appropriate secretory signal can be suitably incorporated into the antibody (e.g. anti-glypican 3 antibody) in order to bring about secretion of the antibody expressed in the host cell into a lumen of endoplasmic reticulum, the periplasmic space, or the extracellular environment. Such a signal can suitably be the native signal sequence characteristic of the antibody (e.g. anti-glypican 3 antibody) or can be a heterologous signal sequence.

The antibody (e.g. anti-glypican 3 antibody) produced as described above can be recovered by collecting the culture medium in those instances where the antibody of the present invention is secreted into the culture medium. In those instances where the antibody (e.g. anti-glypican 3 antibody) of the present invention is produced within the cell, the cell is first lysed and then the antibody is recovered.

Known methods can be suitably used to purify the antibody (e.g. anti-glypican 3 antibody) of the invention recovered from the recombinant cell culture, for example, ammonium sulfate and ethanol precipitation, acid extraction, anion- or cation-exchange chromatography, phosphocellulose chromatography, hydrophobic interaction chromatography, affinity chromatography, hydroxyapatite chromatography, and lectin chromatography.

The present invention also relates to a composition (a drug) comprising a pharmaceutically acceptable carrier and the antibody (e.g. anti-glypican 3 antibody) (for example, IgG antibody) having plasma kinetics modulated by the method of the invention.

The pharmaceutical composition in the context of the present invention generally refers to an agent for the treatment or prevention of a disease or for the detection or diagnosis of a disease.

The pharmaceutical composition of the present invention can be formulated by a method known to those skilled in the art. For example, the formulation can be used by a non-oral route in the form of an injectable, i.e., a suspension or aseptic solution with water or other pharmaceutically acceptable liquid. For example, the formulation can be prepared by combining the antibody with a pharmacologically acceptable carrier or medium, in particular with sterile water or physiological saline, plant oil, emulsifying agent, suspending agent, surfactant, stabilizer, flavorant, diluent, carrier, preservative, binder, and so forth, and mixing in the unit dosage state required by generally established pharmaceutical practice. The amount of active ingredient in the formulations is selected in such a manner that a suitable dose in the indicated range is obtained.

A sterile composition for injection can be suitably formulated in accordance with standard pharmaceutical practice using a carrier such as distilled water for injection.

The aqueous solution for injection can be, for example, an isotonic solution containing physiological saline, dextrose, and other adjuvants (for example, D-sorbitol, D-mannose, D-mannitol, sodium chloride). Suitable solubilizing agents (e.g., an alcohol such as ethanol or a polyalcohol such as propylene glycol or polyethylene glycol) and nonionic surfactant (e.g., Polysorbate 80™, HCO-50) can also be used as appropriate.

Oily liquids include sesame oil and soy oil. Benzyl benzoate and/or benzyl alcohol can also be suitably used as solubilizing agents. A buffer (for example, phosphate buffer solution, sodium acetate buffer solution), soothing agent (for example, procaine hydrochloride), stabilizer (for example, benzyl alcohol and phenol), and oxidation inhibitor can also be incorporated as appropriate. The injection solution prepared as described above is generally filled into suitable ampoules.

The pharmaceutical composition of the present invention can be administered preferably by non-oral administration. For example, it can be formulated as an injectable composition, a transnasal composition, a composition for inhalation administration, or a transdermal composition. It can be suitably administered systemically or locally by, for example, intravenous injection, intramuscular injection, intraperitoneal injection, or subcutaneous injection.

The method of administration can be selected as appropriate depending on the patient's age and symptoms. The dosage of the pharmaceutical composition comprising the antibody or polynucleotide encoding the antibody can be selected, for example, in the range of 0.0001 mg to 1000 mg per 1 kg body weight per unit dose. Or, the dosage can be formulated or set at a dosage of 0.001 to 100,000 mg per patient; however, the present invention is not necessarily limited to these numerical values. The dosage and method of administration will vary depending on the patient's body weight, age, and symptoms, and an appropriate dosage and method of administration can be selected by those skilled in the art based on a consideration of these factors.

The present invention also provides nucleic acid encoding the antibody (e.g. anti-glypican 3 antibody) (for example, humanized anti-glypican 3 antibody) having plasma kinetics modulated by the method of the present invention. A vector carrying such a nucleic acid is also encompassed by the present invention.

The present invention also provides a host cell that comprises the aforementioned nucleic acid. The type of the host cell is not particularly limited, and it may be, for example, a bacterial cell such as E. coli or any of various animal cells. The host cell can be used as appropriate in a production system for the production or expression of the antibody (e.g. anti-glypican 3 antibody) of the present invention. Thus, the present invention also provides a production system that may be used to produce the antibody (e.g. anti-glypican 3 antibody) using the aforementioned host cell. An in vitro or in vivo production system can suitably be used as the production system. Eukaryotic cells and prokaryotic cells are suitably employed as the host cells used in the in vitro production system.

The eukaryotic cells used as the host cell may include animal cells, plant cells, and fungi cells. The animal cells may include mammalian-type cells such as CHO (*J. Exp. Med.* (1995) 108, 945), COS, HEK293, 3T3, myeloma, BHK (baby hamster kidney), HeLa, Vero, and so forth; amphibian cells such *Xenopus laevis* oocytes (Valle et al., *Nature* (1981) 291, 338-340); and insect cells such as Sf9, Sf21, and Tn5. For example, CHO-DG44, CHO-DX11B, COST cells, HEK293 cells, and BHK cells are suitably used for expression of the anti-glypican 3 antibody of the present invention. The use of CHO cells as the host cell is particularly preferred when high levels of expression in animal cells is intended. Transfection of the recombinant vector into the host cell is suitably carried out using the calcium phosphate technique, DEAE dextran technique, techniques that employ the cationic liposome DOTAP (Boehringer Mannheim), electroporation technique, lipofection technique, and so forth.

With regard to plant cells, *Lemna minor* and cells derived from *Nicotiana tabacum* are known as protein production systems, and the anti-glypican 3 antibody of the present invention can be produced by callus culture techniques using these cells. With regard to fungi cells, protein expression systems using yeast cells, e.g., *Saccharomyces* (e.g., *Saccharomyces cerevisiae, Schizosaccharomyces pombe*), and protein expression systems using filamentous fungi, e.g., *Aspergillus* (e.g., *Aspergillus niger*), are known and can be used as host cells to produce the anti-glypican 3 antibody of the present invention.

With regard to the use of prokaryotic cells, any production systems using bacterial cells are suitably used. Production systems that use *E. coli* as described above or *B. subtilus* are known for the bacterial cells, and any of these bacterial cells can be suitably used to produce the antibody (e.g. anti-glypican 3 antibody) of the present invention.

In order to produce the antibody (e.g. anti-glypican 3 antibody) using a host cell of the present invention, the host cell transformed with the expression vector comprising polynucleotide encoding the antibody of the present invention is cultured to express a polynucleotide coding for the antibody (e.g. anti-glypican 3 antibody). The host cells can be cultured according to known methods. When an animal cell is used as the host, for example, DMEM, MEM, RPMI1640, or IMDM is suitably used as the culture medium. A serum auxiliary, e.g., FBS, fetal calf serum (FCS), and so forth, may be added. The cells can also be cultured in a serum-free medium. The cells can be cultured at a pH of about 6-8, depending on the host cell. Culture is generally run for about 15 to 200 hours at about 30 to 40° C., with medium replacement, aeration, and stirring as necessary.

On the other hand, production systems based on an animal or plant are available as in vivo systems for producing the antibody (e.g. anti-glypican 3 antibody) of the present invention. Polynucleotide encoding the antibody (e.g. anti-glypican 3 antibody) of the present invention is introduced into an animal or plant and the antibody is produced within the animal or plant and is recovered. The term "host" as used herein encompasses such animals and plants.

When an animal is used as the host, production systems based on mammals and insects are available. Goat, pig, sheep, mouse, cow, and so forth, are suitably used as the mammal (Vicki Glaser, SPECTRUM Biotechnology Applications (1993)). A transgenic animal may also be employed.

For example, a polynucleotide encoding the antibody (e.g. anti-glypican 3 antibody) of the present invention can be produced in the form of a fusion gene with a gene encoding a polypeptide that is specifically produced in milk, such as goat β-casein. A polynucleotide fragment comprising the fusion gene is then injected into a goat embryo and is transplanted into a female goat. The antibody (e.g. anti-glypican 3 antibody) of interest is obtained from milk produced by the transgenic goat born out of the goat that received the embryo or from milk produced by the offspring of the transgenic goat. Suitable hormones may be administered as appropriate to the transgenic goat in order to increase the amount of antibody (e.g. anti-glypican 3 antibody)-containing milk produced from the transgenic goat (Ebert et al., *Bio/Technology* (1994) 12, 699-702).

The silkworm is an example of an insect that can be used to produce the antibody (e.g. anti-glypican 3 antibody) of the present invention. When the silkworm is employed, the silkworm may be infected with a baculovirus having a polynucleotide encoding the desired antibody (e.g. anti-glypican 3 antibody) inserted into its viral genome. The antibody (e.g. anti-glypican 3 antibody) of interest is obtained from the body fluids of the infected silkworm (Susumu et al., *Nature* (1985) 315, 592-4).

The tobacco plant is an example of a plant that may be used to produce the antibody (e.g. anti-glypican 3 antibody) of the present invention. When the tobacco plant is used, polynucleotide encoding the antibody (e.g. anti-glypican 3 antibody) of interest is inserted into a plant expression vector, such as pMON 530, and the resulting recombinant vector is transfected into a bacterium such as *Agrobacterium tumefaciens*. This bacterium is then used to infect a tobacco plant (for example, *Nicotiana tabacum*) (Ma et al., *Eur. J. Immunol.* (1994) 24, 131-8), and the desired antibody (e.g. anti-glypican 3 antibody) is obtained from the leaves of the infected tobacco plant. *Lemna minor* can be similarly infected with such a bacterium and the desired antibody (e.g. anti-glypican 3 antibody) can be obtained from cells of the cloned infected *Lemna minor* (Cox K. M. et al., *Nat. Biotechnol.* (2006) 24(12), 1591-7).

The antibody (e.g. anti-glypican 3 antibody) of the present invention obtained in the manner described above can be isolated from inside or outside of the host cells (e.g., culture medium or milk) and can be purified into a substantially pure homogeneous antibody. The separation and purification techniques generally used for polypeptide purification can be suitably used for antibody separation and purification in the present invention, but is not limited. For example, the antibody can be suitably separated and purified by a suitable selection and combination of column chromatography, filtration, ultrafiltration, salting out, solvent precipitation, solvent extraction, distillation, immunoprecipitation, SDS-polyacrylamide gel electrophoresis, isoelectric electrophoresis, dialysis, recrystallization, and so forth.

The chromatographic techniques include affinity chromatography, ion-exchange chromatography, hydrophobic chromatography, gel filtration chromatography, reverse-phase chromatography, adsorption chromatography, and so forth (*Strategies for Protein Purification and Characterization: A Laboratory Course Manual*. Ed. Daniel R. Marshak et al. (1996) Cold Spring Harbor Laboratory Press). Chromatography can be carried out using liquid-phase chromatography, for example, HPLC, FPLC, and so forth. The column used in affinity chromatography includes, for example, a protein A column or protein G column. Hyper D, POROS, and Sepharose F. F. (Pharmacia) are examples of protein A based columns.

Another preferred embodiment of the present invention is a method of preparing the antibody (e.g. anti-glypican 3 antibody) with modulated plasma kinetics of the present invention, comprising the step of culturing a host cell of the present invention as described above and recovering the antibody (e.g. anti-glypican 3 antibody) from the cell culture.

All of the literature cited in the specification are incorporated herein by reference.

The present invention is specifically described in the following, but the present invention is not limited to the examples provided below.

EXAMPLES

Example 1

(1) Construction of Point-Mutation Genes of the Humanized H0L0 Antibody

Various point-mutation genes were constructed starting from a gene encoding anti-glypican 3 antibody comprising the CDR of the humanized GC33 antibody disclosed in WO 2006/046751. OligoDNAs designed based on the sequences of the sense and antisense chains containing the modification sites were synthesized. A plurality of point-mutation genes were constructed using the commercial QuikChange Site-Directed Mutagenesis Kit (Stratagene). Construction of the point-mutation genes was carried out by PCR under the following conditions. After heating for 30 seconds at 95° C., a reaction mixture of 10 ng template plasmid, 10 pmol forward chain and reverse chain synthetic oligo-DNAs and 10× buffer, dNTP mix, and Pfu Turbo DNA Polymerase provided with the kit was subjected to 18 cycles of 95° C. 30 sec, 55° C. 1 min and 68° C. 4 min. The DpnI provided with the kit was added to the reaction mixture, and restriction digestion with the restriction enzyme was carried for 1 hour at 37° C. DH5α competent cells (Toyobo) were transformed with the resulting reaction solution to obtain transformants. The introduction of point mutation was confirmed by determining the nucleotide sequence of the plasmid DNA isolated from the transformants. Each point-mutation gene was cloned into expression vectors capable of expressing the insert gene in animal cells. Modified genes were prepared by modifications as described below.

Transient expression of the humanized H0L0 antibody and its point mutation-modified antibodies was carried out using polyethyleneimine (Polysciences Inc.). HEK293 cells were separated by trypsin EDTA (Invitrogen), and seeded to a 10 $cm^2$ culture dish at $6\times10^6$ cells/10 mL. The next day, SFMII culture medium and polyethyleneimine were mixed with a heavy chain expression plasmid DNA and a light chain expression plasmid DNA according to the manufacturer's instructions, and the resulting mixture was left stand for 10 minutes at room temperature. The entire mixture was added dropwise to the culture dish containing the HEK293 cells seeded as described above. The culture supernatant was recovered after approximately 72 hours and the expressed humanized H0L0 antibody and its point mutation-modified antibodies were purified using rProteinA Sepharose™ Fast Flow (GE Healthcare) according to the manufacturer's instructions.

(1-1) Modification of the Tm Value of the Humanized H0L0 Antibody

The thermal denaturation midpoint temperature (Tm) was determined by the top of the denaturation peak in the thermogram (Cp versus T) obtained after heating the test sample solution at a constant programmed heating rate. The Tm value of the humanized H0L0 antibody was measured using a sample solution for DSC measurement prepared as described in the following. The antibody solution (corresponding to 50 to 100 μg) filled in a dialysis membrane was first dialyzed for 24 hours against a dialysis external solution of 20 mol/L sodium acetate buffer solution (pH 6.0) containing 150 mmol/L sodium chloride. Subsequently, the sample solution was adjusted at its antibody concentration of 50 to 100 μg/mL with dialysis external solution and used as the sample solution for DSC measurement.

A suitable DSC instrument, for example, DSC-II (Calorimetry Sciences Corporation), is used for this experiment. The sample solution prepared as described above and the reference solution (dialysis external solution) were thoroughly degassed, and each of these test specimens was placed in a calorimeter cell and was thermally equilibrated at 40° C. A DSC scan was then run from 40° C. to 100° C. at a scan rate of approximately 1 K/minute. The results of this measurement are given as the top of the denaturation peak as a function of temperature. The thermal denaturation midpoint temperature of the humanized H0L0 antibody was calculated by peak assignment of the Fab domain according to Rodolfo et al., *Immunology Letters* (1999), 47-52. As a specific example, the chart obtained from differential scanning calorimetry (DSC) on the Hspu2.2Lspu2.2 (Hu2.2Lu2.2) antibody is shown in FIG. 1.

The humanized H0L0 antibody, comprising the heavy chain shown in SEQ ID NO: 1 and the light chain shown in SEQ ID NO: 7, has a Tm value of 76.6° C. as calculated by the method described above. The Tm values of Synagis and Herceptin, provided as examples of existing antibodies, are measured at 85.4° C. and 81.8° C., respectively. It was thus shown that the Tm value of the humanized H0L0 antibody is lower than that of existing antibodies.

Modified antibodies were therefore prepared from humanized H0L0 antibody with the aim of raising the Tm value. Modifications of V37I, A40P, M48I, and L51I were introduced into FR2 of the H0L0 antibody heavy chain shown in SEQ ID NO: 1 to prepare the antibody H15 (SEQ ID NO: 2), where its subclass was changed from VH1b to VH4. The Tm value was improved to 79.1° C. Also the H0L0 antibody light chain shown in SEQ ID NO: 7 was modified by introducing L42Q, S48A, and Q50R modifications into the FR2 which changed the subclass from VK2 to VK3, and introducing V2I modification to replace the V2 of FR1 with I (germline sequence), thereby L4 (SEQ ID NO: 8) was prepared. The Tm value of each antibody was measured as described above. The Tm value of H15L0 and H0L4 was 79.2° C. and 77.2° C., respectively, which shows improvement from the Tm value 76.6° C. of H0L0. The Tm value of the H15L4 antibody comprising the combination of these two modifications was improved to 80.5° C.

(1-2) Modification of the pI Value of the Humanized H0L0 Antibody

The plasma half-life of an antibody is extended by lowering the pI value exhibited by the antibody. In contrast, the tissue translocation characteristics of an antibody are improved by increasing the antibody's pI. It is unknown whether either increase or decrease in the pI value of an antibody effective in cancer treatment would enhance the tumor-suppressing effect. Therefore, modified humanized H0L0 antibody with a lowered pI and modified humanized H0L0 antibody with an increased pI were prepared and the antitumor activity of them was compared to investigate if either modification had a higher tumor-suppressing activity.

The pI value of each antibody was calculated based on the analysis by isoelectric electrophoresis. Electrophoresis was carried out as described in the following. Using PhastSystem Cassette (Amersham Bioscience), Phast-Gel Dry IEF (Amersham Bioscience) gel was swollen for about 60 minutes with a swelling solution with the composition given below.

(a) Composition of the swelling solution for high pI:
1.5 mL 10% glycerol
100 μL Pharmalyte 8-10.5 for IEF (Amersham Bioscience)

(b) Composition of the swelling solution for low pI:
1.5 mL purified water
20 μL Pharmalyte 8-10.5 for IEF (Amersham Bioscience)
80 μL Pharmalyte 5-8 for IEF (Amersham Bioscience)

Approximately 0.5 μg antibody was loaded on the swollen gel and isoelectric electrophoresis was run using the PhastSystem (Amersham Bioscience) controlled by the program described below. The sample was added to the gel at Step 2 of this program. A Calibration Kit for pI (Amersham Bioscience) was used for the pI markers.

Figure 2:
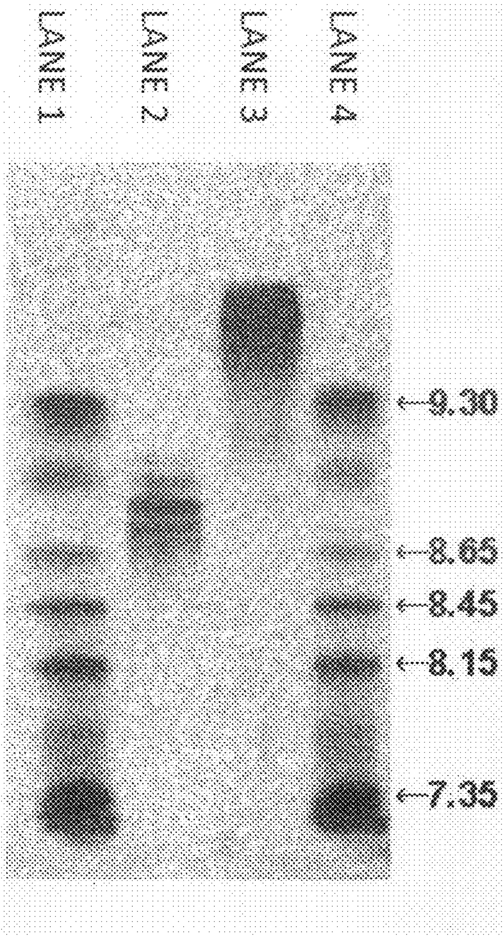
FIG. 2 is an electrophoretogram of H0L0 antibody and Hspu2.2Lspu2.2 (Hu2.2Lu2.2) antibody in high pI isoelectric electrophoresis, wherein lanes 1 and 4 show pI markers, lane 2 shows. H0L0 antibody, and lane 3 shows Hspu2.2Lspu2.2 (Hu2.2Lu2.2) antibody, where the numerical values show the pI values of the pI marker molecules and the arrows show the electrophoretic mobilities of the corresponding pI marker molecules.
Figure 3:
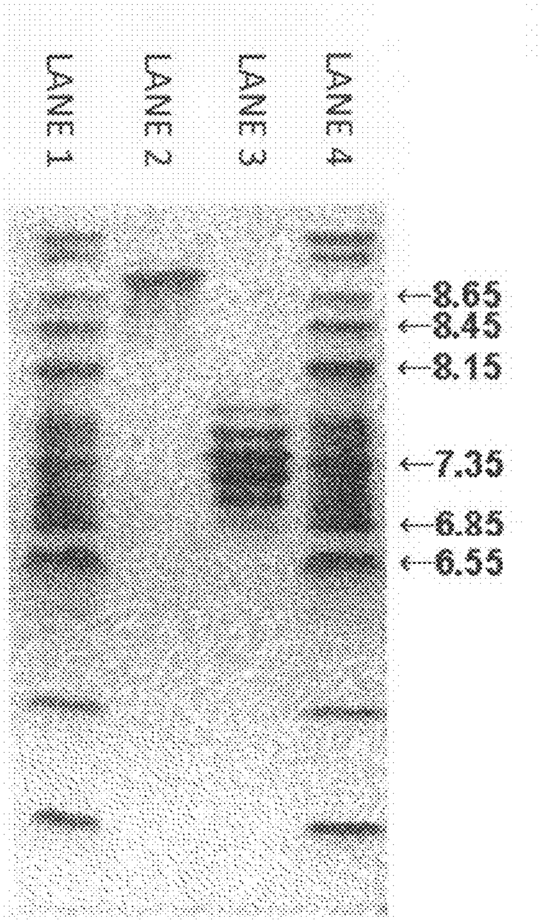
FIG. 3 is an electrophoretogram of H0L0 antibody and Hspd1.8Lspd1.6 (Hd1.8Ld1.6) antibody in low pI isoelectric electrophoresis, wherein lanes 1 and 4 show pI markers, lane 2 shows H0L0 antibody, and lane 3 shows Hspd1.8Lspd1.6 (Hd1.8Ld1.6) antibody, where the numerical values show the pI values of the pI marker molecules and the arrows show the electrophoretic mobilities of the corresponding pI marker molecules.

Step 1: 2000 V, 2.5 mA, 3.5 W, 15° C., 75 Vh
Step 2: 200 V, 2.5 mA, 3.5 W, 15° C., 15 Vh
Step 3: 2000 V, 2.5 mA, 3.5 W, 15° C. 410 Vh After electrophoresis, the gel was fixed with 20% TCA and silver staining was then carried out using Silver Staining Kit, Protein (Amersham Bioscience) according to the instructions provided with the kit. After staining, the isoelectric point of each antibody (test sample) was calculated based on the already known isoelectric points of the pI markers. The electrophoretogram from the high pI isoelectric electrophoresis is shown in FIG. 2 and the electrophoretogram from the low pI isoelectric electrophoresis is shown in FIG. 3.

(a) Modifications that Raised the pI

Hspu2.2 (Hu2.2) (SEQ ID NO: 6) was prepared, in which the Q43K, D52N, and Q107R modifications were additionally implemented in H15. Lspu2.2 (Lu2.2) (SEQ ID NO: 12) was also prepared, in which the E17Q, Q27R, Q105R and S25A modifications were implemented in L4, where the S25A modification replaces S25 in CDR2 with A (abundant in a germline). The Tm value of the Hspu2.2Lspu2.2 (Hu2.2Lu2.2) antibody composed of Hspu2.2 (Hu2.2) and Lspu2.2 (Lu2.2) was measured at 76.8° C. and its pI value was measured at 9.6. Since the pI of the H0L0 antibody is 8.9, the pI of the Hspu2.2Lspu2.2 (Hu2.2Lu2.2) antibody was increased by 0.7.

(b) Modifications that Lowered the pI

Hspd1.8 (Hd1.8) (SEQ ID NO: 5) was prepared, in which the K19T, Q43E, K63S, K65Q, and G66D modifications were additionally implemented in H15. Lspd1.6 (Ld1.6) (SEQ ID NO: 11) was prepared by making the following modifications: the Q27E modification in L4; modification of KISRVE at 79-84 of the FR3 in L4 to TISSLQ; and the S25A modification to achieve the same modification as for Lspu2.2 (Lu2.2). The pI value of the Hspd1.8Lspd1.6 (Hd1.8Ld1.6) antibody composed of Hspd1.8 (Hd1.8) and Lspd1.6 (Ld1.6), was measured at 7.4. Since the pI of the H0L0 antibody is 8.9, the pI of the Hspd1.8Lspd1.6 (Hd1.8Ld1.6) antibody was reduced by 1.5.

(2) Evaluation by Competitive ELISA of the Binding Activity of the Point-Mutation Modified Antibodies from the H0L0 Antibody The H0L0 antibody and its point mutation-modified antibodies purified in (1) was evaluated by competitive ELISA. 100 μL of the soluble GPC3 core polypeptide (SEQ ID NO: 13) at 1 μg/mL was added to each well of a 96-well plate. The soluble GPC3 core polypeptide was immobilized on the plate by allowing the plate to stand overnight at 4° C. The soluble GPC3 core polypeptide immobilized on the plate was washed 3 times with a washing buffer using Skan WASHER400 (Molecular Devices); and blocked with 200 μL blocking buffer at 4° C. for at least 30 min. The blocked plate on which soluble GPC3 core polypeptide was immobilized was then washed 3 times with washing buffer using the Skan WASHER400. Subsequently, each well of the plate received 200 μL of a mixture containing 100 μL of biotinylated H0L0 antibody (final concentration=0.3 μg/mL) and 100 μL of the H0L0 antibody or its point mutation-modified antibody (at various concentrations). The H0L0 antibody was biotinylated using Biotin Labeling Kit (Roche) according to the instructions provided with the kit. The plate was left stand for 1 hour at room temperature, then washed 5 times with washing buffer using the Skan WASHER400 (Molecular Devices). 100 μL goat anti-streptavidin alkaline phosphatase (ZYMED), diluted 20,000× with substrate buffer, was added to each well, and the resulting plate was left stand for 1 hour at room temperature, and then washed 5 times with washing buffer using the Skan WASHER400. Phosphatase Substrate (Sigma) was prepared at 1 mg/mL in the substrate buffer, added at 100 μL per well for 1 hour. The absorbance at 405 nm of the reaction solution in each well was measured using Benchmark Plus (BIO-RAD), with the control absorbance at 655 nm.

Figure 4:
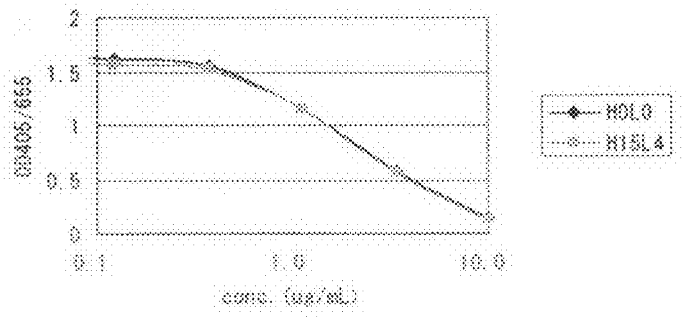
FIG. 4 is a diagram that shows the binding affinity of H15L4 antibody and H0L0 antibody for glypican 3 antigen in competitive ELISA, wherein the black diamond refers to the binding affinity of the H0L0 antibody and the grey square refers to the binding affinity of the H15L4 antibody.
Figure 5:
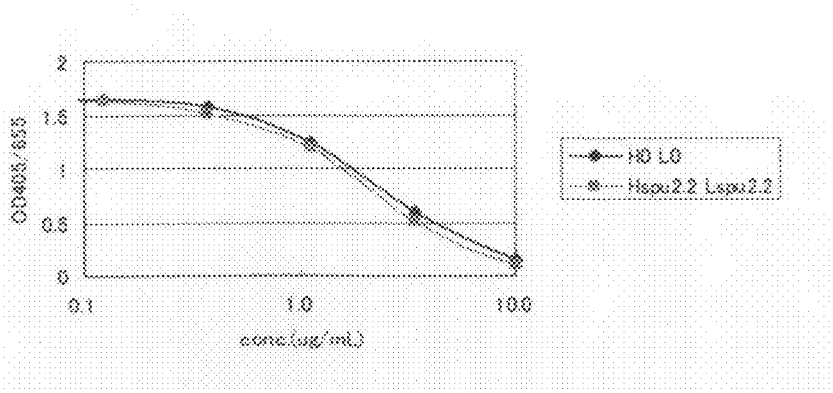
FIG. 5 is a diagram that shows the binding affinity of Hspu2.2Lspu2.2 (Hu2.2Lu2.2) antibody and H0L0 antibody for glypican 3 antigen in competitive ELISA, wherein the black diamond refers to the binding affinity of the H0L0 antibody and the grey square refers to the binding affinity of the Hspu2.2Lspu2.2 (Hu2.2Lu2.2) antibody.
Figure 6:
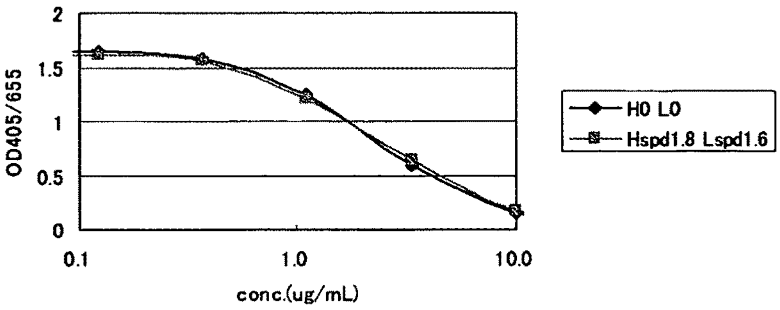
FIG. 6 is a diagram that shows the binding affinity of Hspd1.8Lspd1.6 (Hd1.8Ld1.6) antibody and H0L0 antibody for glypican 3 antigen in competitive ELISA, wherein the black diamond refers to the binding affinity of the H0L0 antibody and the grey square refers to the binding affinity of the Hspd1.8Lspd1.6 (Hd1.8Ld1.6) antibody.

As shown by FIG. 4, the antigen binding activity of the H15L4 antibody was shown to be almost the same as that of the H0L0 antibody that had been subjected to the modification. In addition, as shown in FIG. 5, the antigen binding activity of the Hspu2.2Lspu2.2 (Hu2.2Lu2.2) antibody was shown to be about the same as that of the H0L0 antibody subjected to the modification. Moreover, as shown in FIG. 6, the antigen binding activity of the Hspd1.8Lspd1.6 (Hd1.8Ld1.6) antibody was shown to be about the same as that of the H0L0 antibody subjected to the modification.

Reference Example 2

Disruption of the Fucose Transporter Gene in CHO Cells (1) Construction of the Targeting Vector (1-1) Construction of the KO1 Vector The BamHI site and the TGCGC sequence were added at the 5' side of the start codon of the hygromycin resistance gene (Hygr) by PCR using pcDNA3.1/Hygro (Invitrogen) with primers Hyg5-BH and Hyg3-NT to obtain the same sequence as on the 5' side of the start codon of the fucose transporter gene. Also the NotI site was added on the 3' side including the region up to the SV40 polyA addition signal. Then the Hygr gene was excised.

```
forward primer
                                          (SEQ ID NO: 14)
Hyg5-BH   5'-GGATCCTGCGCATGAAAAAGCCTGAACTCACC-3'

reverse primer
                                          (SEQ ID NO: 15)
Hyg3-NT   5'-GCGGCCGCCTATTCCTTTGCCCTCGGACG-3'
```

Fucose transporter targeting vector ver. 1 (referred to as the KO1 vector) was constructed by inserting the 5' side of the fucose transporter (from the SmaI at No. 2,780 of SEQ ID NO: 16 to the BamHI at No. 4,232), the 3' side (from No. 4,284 to the SacI at No. 10,934), and the Hygr fragment into the pMC1DT-A vector (Yagi T., *Proc. Natl. Acad. Sci. USA* (1990) 87, 9918-22). A characteristic feature of this vector is that, when homologous recombination has occurred, Hygr is expressed under the promoter of the fucose transporter, since a promoter is not attached to the Hygr gene. However, when only one copy of the vector is introduced into the cell by homologous recombination, Hygr is not always expressed to a degree sufficient for exhibiting hygromycin B resistance. The KO1 vector was cleaved at the NotI site and was transfected into the cell. It is thought that 41 base pairs in exon 1, including the start codon, will be deleted from the fucose transporter by introduction of the KO1 vector, resulting in a loss of function.

(1-2) Construction of pBSK-pgk-1-Hygr pBSK-pgk-1 was constructed by excising the mouse pgk-1 gene promoter from the pKJ2 vector (Popo H., *Biochemical Genetics* (1990) 28, 299-308) with EcoRI-PstI and cloning it into the EcoRI-PstI sites of pBluescript (Stratagene). With regard to Hygr, an EcoT22I site and a Kozak sequence were added on the 5' side of Hygr and a BamHI site was added on the 3' side including the region up to the SV40 polyA addition signal by PCR using pcDNA3.1/Hygro with the Hyg5-AV and Hyg3-BH primers. Then the Hygr gene was excised.

```
forward primer
                                          (SEQ ID NO: 17)
Hyg5-AV   5'-ATGCATGCCACCATGAAAAAGCCTGAACTCACC-3'

reverse primer
                                          (SEQ ID NO: 18)
Hyg3-BH   5'-GGATCCCAGGCTTTACACTTTATGCTTC-3'
```

pBSK-pgk-1-Hygr was constructed by inserting the Hygr fragment (EcoT22I-BamHI) into the PstI-BamHI sites of pBSK-pgk-1.

(1-3) Construction of the KO2 Vector

Fucose transporter targeting vector ver. 2 (referred to hereafter as the KO2 vector) was constructed by inserting the 5' side of the fucose transporter (from the SmaI site at No. 2,780 of SEQ ID NO: 16 to the BamHI at No. 4,232), the 3' side (from No. 4,284 to the SacI site at No. 10,934), and the pgk-1-Hygr fragment into the pMC1DT-A vector. Unlike the case for the KO1 vector, the KO2 vector has the pgk-1 gene promoter attached to Hygr, thus will acquire hygromycin B resistance even when only one copy of the vector is introduced into the cell by homologous recombination. The KO2 vector was cleaved at Not1 and was transfected into the cell. By introducing the KO2 vector, 46 base pairs in exon 1 including the start codon will be deleted from the fucose transporter, resulting in a loss of function.

(1-4) Construction of pBSK-pgk-1-Puror

The pPUR vector (BD Biosciences) was cleaved by PstI and BamHI and the excised fragment (Puror) was inserted into the PstI-BamHI sites of pBSK-pgk-1 to construct pBSK-pgk-1-Puror.

(1-5) Construction of the KO3 Vector

Fucose transporter targeting vector ver. 3 (referred to hereafter as the KO3 vector) was constructed by inserting the 5' side of the fucose transporter (from the SmaI site at No. 2,780 of SEQ ID NO: 16 to the BamHI at No. 4,232), the 3' side (from No. 4,284 to the SacI site at No. 10,934), and the pgk-1-Puror fragment into the pMC1DT-A vector. A sequence for binding to the screening primer shown below was preliminarily attached to the 3' end of pgk-1-Puror. The KO3 vector was cleaved by NotI and was transfected into the cell. By introducing the KO3 vector, 46 base pairs in exon 1 including the start codon will be deleted from the fucose transporter, resulting in a loss of function.

```
reverse primer
RSGR-A
5'-GCTGTCTGGAGTACTGTGCATCTGC-3'   (SEQ ID NO: 19)
```

The fucose transporter gene was knocked out using the three targeting vectors described above.

(2) Introduction of Vector Into CHO Cells

HT Supplement (100×) (Invitrogen) and penicillin-streptomycin (Invitrogen) were added to CHO-S-SFMII HT- (Invitrogen), each at 1/100th the volume of the CHO-S-SFMII HT- to prepare a culture medium (hereafter referred to as SFMII (+)). CHO DXB11 cells were subcultured in SFMII(+). $8\times10^6$ CHO cells were suspended in 0.8 mL Dulbecco's phosphate buffer (Invitrogen) (referred to hereafter as PBS). 30 μg of targeting vector was added to the cell suspension, and transferred to a Gene Pulser cuvette (4 mm) (BioRad). After holding for 10 minutes on ice, the vector was transfected into the cells by electroporation with GENE PULSER II (BioRad) at 1.5 kV and 25 μFD. After vector transfection, the cells were suspended in 200 mL SFMII(+) medium and were seeded into twenty 96-well flat-bottom plates (Iwaki) at 100 μl/well. The plates were cultured for 24 hours at 37° C. in a $CO_2$ incubator, then the reagent was added.

(3) Knockout: Step 1

KO1 vector or KO2 vector was transfected into the CHO cells, and selected with hygromycin B (Invitrogen) 24 hours after vector transfection. The hygromycin B was dissolved in SFMII(+) at 0.3 mg/mL, and 100 μL was added per well.

(4) Screening for Homologous Recombinants by PCR (4-1) Preparation of the Sample for PCR Homologous recombinants were screened by PCR. The CHO cells were cultured on 96-well flat-bottom plates, the culture supernatant was removed and a cell lysis buffer was added at 50 μL/well, and incubated at 55° C. for 2 hours. Then proteinase K was deactivated by heating at 95° C. for 15 minutes to prepare a PCR template. The cell lysis buffer was composed of the following per well: 5 μL 10× LA Buffer II (supplied with Takara LA Taq), 2.5 μL 10% NP-40 (Roche), 4 μL proteinase K (20 mg/mL, Takara), and 38.5 μL distilled water (Nacalai Tesque).

(4-2) PCR Conditions

The PCR reaction mixture was comprised of 1 μL of the PCR sample as described above, 5 μL 10× LA Buffer II, 5 μL $MgCl_2$ (25 mM), 5 μL dNTP (2.5 mM), 2 μL primer (10 μM each), 0.5 μL LA Taq (5 IU/μL), and 29.5 μL distilled water (total of 50 μL). The TP-F4 and THygro-Rl primers were used as the PCR primers to screen the KO1 vector-transfected cells, and the TP-F4 and THygro-F1 primers were used as the PCR primers to screen the KO2 vector-transfected cells.

PCR screening for the KOl vector-transfected cells was carried out by preheating for 1 minute at 95° C.; 40 cycles of 95° C./30 seconds, 60° C./30 seconds, and 60° C./2 minutes; and reheating at 72° C. for 7 minutes. PCR screening for the KO2 vector-transfected cells was carried out by preheating for 1 minute at 95° C.; 40 cycles of 95° C./30 seconds and 70° C./3 minutes; and reheating at 70° C. for 7 minutes.

The primers are given below. In cell samples where homologous recombination had occurred, approximately 1.6 kb DNA is amplified for the KO1 vector and approximately 2.0 kb DNA is amplified for the KO2 vector. TP-F4 primer was designed in the genomic region of the fucose transporter on the 5' side outside the vector, and the THygro-FI and THygro-R1 primers were designed in the Hygr within the vector.

```
forward primer (KO1, KO2)
TP-F4
5'-GGAATGCAGCTTCCTCAAGGGACTCGC-3'  (SEQ ID NO: 20)

reverse primer (KO1)
THygro-R1
5'-TGCATCAGGTCGGAGACGCTGTCGAAC-3'  (SEQ ID NO: 21)

reverse primer (KO2)
THygro-F1
5'-GCACTCGTCCGAGGGCAAAGGAATAGC-3'  (SEQ ID NO: 22)
```

(5) Results of the PCR Screening

918 KO1 vector-transfected cells were analyzed, and 1 cell was thought to be a homologous recombinant (homologous recombination efficiency=approximately 0.1%). 537 KO2 vector-transfected cells were analyzed; and 17 cells were thought to be homologous recombinants (homologous recombination efficiency=approximately 3.2%).

(6) Southern Blotting Analysis

Further confirmation was carried out by Southern blotting. 10 µg genomic DNA was prepared from the cultured cells by a standard method and was subjected to Southern blotting. Using the two primers given below, a 387 by probe was prepared by PCR spanning the region from No. 2,113 to No. 2,500 in the nucleotide sequence shown in SEQ ID NO: 16, and used for Southern blotting. The genomic DNA was cleaved with Bg1II.

```
forward primer
Bgl-F
5'-TGTGCTGGGAATTGAACCCAGGAC-3'  (SEQ ID NO: 23)

reverse primer
Bgl-R
5'-CTACTTGTCTGTGCTTTCTTCC-3'    (SEQ ID NO: 24)
```

Cleavage by BglII provides an approximately 3.0 kb band from the fucose transporter chromosome, an approximately 4.6 kb band from the chromosome where homologous recombination occurred with the KO1 vector, and an approximately 5.0 kb band from the chromosome where homologous recombination occurred with the KO2 vector. One cell obtained by homologous recombination with the KO1 vector and 7 cells obtained by homologous recombination with the KO2 vector were used in the experiments. The only cell obtained with the KO1 vector was designated 5C1; however, it was shown by subsequent analysis to comprise multiple cell populations. Thus cloning by limiting dilution was carried out before using it in the subsequent experiments. One of the cells obtained with the KO2 vector was designated 6E2.

(7) Knockout: Step 2

In order to establish cell lines having a completely defective fucose transporter gene, one of three vectors was introduced into the cells in which homologous recombination had been achieved by the KO1 vector or KO2 vector. The vector/cell combinations were as follows: method 1: KO2 vector and 5C1 cells (KO1); method 2: KO2 vector and 6E2 cells (KO2); method 3: KO3 vector and 6E2 cells (KO2). The vector was transfected into the respective cell, and selection with hygromycin B and puromycin (Nacalai Tesque) was initiated 24 hours after vector transfection. The final hygromycin B concentration was 1 mg/mL in method 1 and 7 mg/mL in method 2. In method 3, the hygromycin B was added at a final concentration of 0.15 mg/mL and the puromycin was added at a final concentration of 8 µg/mL.

(8) PCR Screening of the Homologous Recombinants

The samples were prepared as described above. In the screening for method 1, both PCRs by which cells were detected where homologous recombination had occurred with the KO1 vector and the KO2 vector were performed. The PCR primers shown below were designed for method 2. TPS-F1 corresponds to the region from No. 3,924 to No. 3,950 in the nucleotide sequence shown in SEQ ID NO: 16, while SHygro-R1 corresponds to the region from No. 4,248 to 4,274. These PCR primers will amplify 350 by of the fucose transporter gene region that is otherwise deleted by the KO2 vector. Therefore, in the PCR screening in method 2, cells producing no 350 by amplification product are considered to be the cells completely lacking the fucose transporter gene. The PCR conditions were as follows: preheating for 1 minute at 95° C.; 35 amplification cycles of 95° C./30 seconds and 70° C./1 minute; and reheating at 70° C. for 7 minutes.

```
forward primer
TPS-F1
5'-CTCGACTCGTCCCTATTAGGCAACAGC-3'  (SEQ ID NO: 25)

reverse primer
SHygro-R1
5'-TCAGAGGCAGTGGAGCCTCCAGTCAGC-3'  (SEQ ID NO: 26)
```

In the case of method 3, TP-F4 was used as the forward primer and RSGR-A was used as the reverse primer. The PCR conditions were as follows: preheating for 1 minute at 95° C.; 35 amplification cycles of 95° C./30 seconds, 60° C./30 seconds, and 72° C./2 minutes; reheating at 72° C. for 7 minutes. Approximately 1.6 kb DNA will be amplified from the cell samples in which homologous recombination by the KO3 vector has occurred. By this PCR, the cells in which homologous recombination occurred by the KO3 vector were detected, and it was also confirmed that the cells retained the homologous recombination by the KO2 vector while detecting (9) Results of PCR Screening 18 cells out of 616 cells analyzed by method 1 were considered to be homologous recombinants (homologous recombination efficiency=2.9%). 2 cells out of 524 cells analyzed by method 2 were considered to be homologous recombinants (homologous recombination efficiency=approximately 0.4%). 7 cells out of 382 cells analyzed by method 3 were considered to be homologous recombinants (homologous recombination efficiency=approximately 1.8%).

(10) Southern Blotting Analysis

Southern blotting analysis was carried out by the method described above, and 1 cell was identified to have the fucose transporter gene being completely lost. The analytical results from PCR and Southern blotting were consistent in the knockout step 1, but not in the knockout step 2.

(11) Fucose Expression Analysis 26 cells found to be homologous recombinants were analyzed for fucose expression by PCR. $1\times10^6$ cells were stained in 100 μL PBS containing 5 μg/mL *Lens culinaris* agglutinin, FITC conjugate (Vector Laboratory), 2.5% FBS, and 0.02% sodium azide (referred to hereafter as FACS solution) for 1 hour with ice cooling. The cells were then washed 3 times with FACS solution and were analyzed by FACSCalibur (Becton Dickinson). The results showed that fucose expression was reduced only in FTP-KO cells, which were found to exhibit a complete loss of the fucose transporter gene in the Southern blot analysis.

Reference Example 3

Establishment of Antibody-Producing Cells Derived from the FTP-KO Line and Purification of Antibody Produced by these Cells The fucose transporter-deficient line obtained in Example 1 (FTP-KO cells, clone name: 3F2) were subcultured in SFMII(+) containing hygromycin B at a final concentration of 1 mg/mL. $8\times10^6$ 3F2 cells were suspended in 0.8 mL Dulbecco's phosphate buffer. 25 μg of a humanized anti-glypican 3 antibody expression vector was added to the cell suspension and transferred to a Gene Pulser cuvette. After holding for 10 minutes on ice, the vector was transfected into the cells by electroporation with GENE PULSER II at 1.5 kV and 25 μFD. After vector transfection, the cells were suspended in 40 mL SFMII(+) medium and were seeded on a 96-well flat-bottom plate (Iwaki) at 100 μL/well. After the plate was incubated for 24 hours at 37° C. in a $CO_2$ incubator, geneticin (Invitrogen) was added to a final concentration of 0.5 mg/mL. The antibody production of the drug-resistant cells was measured to obtain humanized anti-glypican 3 antibody-producing cell lines.

The culture supernatant from the antibody-expressing lines was collected and applied to Hitrap rProtein A column (Pharmacia) using P-1 pump (Pharmacia). The column was washed with a binding buffer (20 mM sodium phosphate (pH 7.0)), and the bound antibody was subsequently eluted with elution buffer (0.1 M glycine-HCl (pH 2.7)). The eluate was immediately neutralized with neutralization buffer (1 M Tris-HCl (pH 9.0)). The eluted antibody fractions were selected using DC protein assay (BioRad) and pooled, and was concentrated to about 2 mL with Centriprep-YM10 (Millipore). The concentrated solution was then subjected to gel filtration on Superdex200 26/60 (Pharmacia) equilibrated with 20 mM acetic acid buffer (pH 6.0) containing 150 mM NaCl. The peak of the monomer fraction in the eluate was collected and concentrated with Centriprep-YM10. The concentrated solution was filtered using a MILLEX-GW 0.22 μm filter unit (Millipore) and was stored at 4° C. The purified antibody concentration was determined by calculation from the molar absorption coefficient based on the absorbance at 280 nm.

Reference Example 4

Analysis of Sugar Chains Attached to the Humanized Anti-Glypican 3 Antibody Produced by FTP-KO Cells (1) Preparation of 2-aminobenzamide-Labeled Sugar Chains (2-AB-Labeled Sugar Chains)

The antibody of the present invention produced by FTP-KO cells and antibody produced by CHO cells (control) were treated with N-glycosidase F (Roche Diagnostics) to release the antibody-bound sugar chains (Weitzhandler M. et al., *Journal of Pharmaceutical Sciences* (1994) 83(12), 1670-5). After deproteination with ethanol (Schenk B. et al., *The Journal of Clinical Investigation* (2001), 108(11), 1687-95), the released sugar chains were concentrated to dryness and fluorescent-labeled with 2-aminopyridine (Bigge J. C. et al., *Analytical Biochemistry* (1995) 230(2), 229-238). The resulting 2-AB-labeled sugar chains were separated from the reagent by solid-phase extraction using a cellulose cartridge, concentrated by centrifugation to obtain purified 2-AB-labeled sugar chains. The purified 2-AB-labeled sugar chains was treated with β-galactosidase (Seikagaku Kogyo Co., Ltd.) to prepare agalactosyl 2-AB-labeled sugar chains which were analysed as described below.

(2) Analysis of agalactosyl 2-AB-Labeled Sugar Chains by Normal-Phase HPLC

The agalactosyl 2-AB-labeled sugar chains prepared by the above-described method, the sugar chains released from the antibody of the present invention produced by FTP-KO cells and antibody produced by CHO cells (control), were analyzed by normal-phase HPLC with TSKgel Amide-80 amide column (TOSOH Corp.) and the chromatograms were compared. The following assessment was made with respect to the antibody produced by the CHO cells: G(0) was present as the main component of the sugar chains, while G(0)-Fuc lacking fucose accounted for about 4% of the total sugar chains, as assessed by calculation from the peak area ratio. In the case of the antibody produced by FTP-KO cells, G(0)-Fuc was the main component. For all the antibody producing cell lines, at least 90% of the total sugar chain in the produced antibody was fucose-free sugar chains, as assessed by on calculation from the peak area ratio.

TABLE 1

Relative ratios of each sugar chain estimated from normal-phase HPLC analysis for agalactosyl 2-AB-labeled sugar chains

| sugar chain | CHO | FTP-KO-a | FTP-KO-b | FTP-KO-c |
|---|---|---|---|---|
| G(0)-Fuc | 4.0% | 92.4% | 92.5% | 93.2% |
| G(0) | 96.0% | 7.6% | 7.5% | 6.8% |

Example 5

Establishment of Cell Lines Stably Expressing Humanized H0L0 Antibody and Point Mutation-Modified Antibodies The genes encoding Hspu2.2Lspu2.2 (Hu2.2Lu2.2) antibody, Hspd1.8Lspd1.6 (Hd1.8Ld1.6) antibody (H0L0 antibody-sourced modified antibodies produced by the method described in Example 1) or the H0L0 antibody subjected to the modifications were cloned into an expression vector. In the cloning, the genes encoding the heavy chain and light chain were inserted into different expression vectors in order to express each gene encoding the heavy chain and light chain of the antibody. Two expression vectors were selected so as to provide a desired combination of the genes encoding the heavy chain and light chain as described above, digested with PvuI and transfected by electroporation into the FTP-KO line produced in Reference Example 2.

Transformants that stably produce H0L0 antibody or modified antibody were prepared by electroporation using the Gene Pulser II (BioRad). 0.75 mL CHO cells ($1\times10^7$ cells/mL) suspended in PBS was mixed with 10 μg each of expression plasmid DNA providing the desired combination of heavy chain and light chain, and the mixture was left stand on ice for 10 minutes. The mixture was transferred to a Gene Pulser II cuvette and a 1.5 kV electrical pulse was applied at a capacitance of 25 μFD. The pulsed mixture was incubated for 10 minutes at room temperature and suspended in CHO- S-SFMII/1% HT/1% PS medium. 100 μL of the diluted suspension (5 fold, 10 fold, and 50 fold, made in the same medium) was added to each well of 96-well culture plates. The plates were incubated for 24 hours in $CO_2$ incubator maintained at 5% $CO_2$. Then, geneticin (Gibco) was added to each well to a final concentration of 500 μg/mL and zeocin (Invitrogen) was added to each well to a final concentration of 600 μg/mL. The plates were incubated for 2 weeks. The colonies of transformed cells that exhibited geneticin and zeocin resistance were further selected by subculture on the same medium containing 500 μg/mL geneticin (Gibco) and 600 μg/mL zeocin (Invitrogen). The culture supernatant of the transformed cells selected in this manner was evaluated for the antibody concentration using BiacoreQ (BIACORE) to establish transformant cell lines expressing the desired antibody at a high level. The antibody concentration in the culture supernatant was measured according to the instructions provided with the BiacoreQ (BIACORE). The cell line thus established was cultured in CHO-S-SFMII medium (Invitrogen) containing 500 μg/ml of Geneticin (Invitrogen) and 600 μg/ml of Zeocin (Invitrogen). After cultivating for an appropriate period of time, the culture supernatant was collected, and purified using rProteinA-Sepharose column (GE Healthcare). The purified antibody was concentrated with Amicon Ultra-4 (MILLIPORE) and subjected to buffer exchange on PD-10 Desalting column (Amersham Biosciences) with 20 mM acetic acid buffer (pH6.0) containing 200 mM NaCl. The purified antibody was quantified by the absorption at 280 nm in ND-1000 Spectrophotometer (NanoDrop) or DU-600 Spectrophotometer (BECKMAN). The antibody concentration was calculated with the RACE method.

Example 6

Therapeutic Efficacy in an In Vivo Model of the Humanized H0L0 Antibody and the Point Mutation-Modified Antibodies (1) Maintenance of the Cell Line Used for Transplantation Into the In Vivo Model HepG2 cells (ATCC) were used. The HepG2 cells were maintained by subculture in Eagle's minimum essential medium (Sigma) containing sodium pyruvate (Invitrogen) at 1 mmol/L MEM and non-essential amino acids (Invitrogen) at 1 mmol/L MEM (this medium is referred to as the subculture medium).

(2) Preparation of an HepG2 Cell-Transplanted Mouse Model

Using a solution containing subculture medium and MATRIGEL Matrix (BD Bioscience) at 1:1, a suspension of HepG2 cells was prepared at $5\times10^7$ cells/mL. 100 μL of the cell suspension ($5\times10^6$ cells/mouse) was transplanted subcutaneously in the abdominal region of SCID mice (male, 5 week old, CLEA Japan, Inc.). On the day prior to cell transplantation, the mice received 100 μL anti-asialo GM1 antibody (content of 1 vial was dissolved in 5 mL of the aforementioned solution, Wako Pure Chemical Industries, Ltd.) by interperitoreal administration. The tumor volume was calculated according to the following formula.

$$\text{tumor volume}=\text{long diameter}\times\text{short diameter}\times\text{short diameter}/2$$

When the average tumor volume reached 130 to 330 $mm^3$, the mouse was used as a model.

(3) Preparation of Administration Sample Containing the Test Antibody

The administration samples containing H0L0 antibody, Hu2.2Lu2.2 antibody, or Hd1.8Ld1.6 antibody at 0.5 mg/mL (5 mg/kg group) or 0.1 mg/mL (1 mg/kg group) were prepared with physiological saline on the day of administration.

(4) Administration of the Antibody-Containing Administration Sample

The administration sample prepared according to (3) was administered at a dose of 10 mL/kg through the tail vein to the mouse model prepared in (2) at once per week for three weeks beginning 27 days after HepG2 cell transplantation. As a negative control, physiological saline was administered at a dose of 10 mL/kg through the tail vein at once per week for three weeks. All the groups contained 5 animals, and each test antibody-containing administration sample was administered to a respective group. At about the same time as the administration, venous blood was collected from 3 animals in each group was analyzed for the murine plasma concentration of the antibody. Specifically, blood was collected from a dorsal foot vein at two time points: 0.5 hour after the initial administration and immediately before the second administration. 20 μL of collected blood was treated with heparin and the plasma was isolated by centrifugation.

(5) Evaluation of the Antitumor Activity of the Test Antibodies

Figure 7:
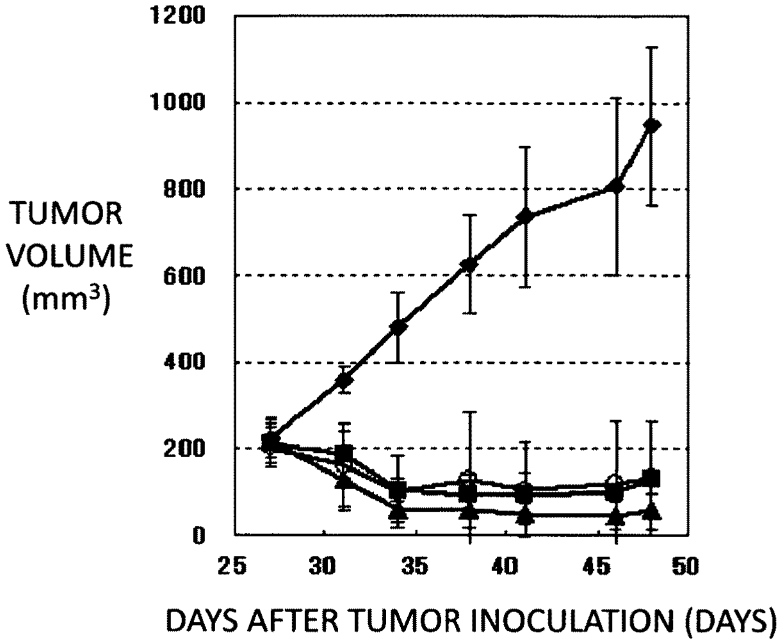
FIG. 7 shows the antitumor activity of the H0L0 antibody, Hspu2.2Lspu2.2 (Hu2.2Lu2.2) antibody, and Hspd1.8Lspd1.6 (Hd1.8Ld1.6) antibody in a human liver cancer-transplant mouse model.
Figure 7:
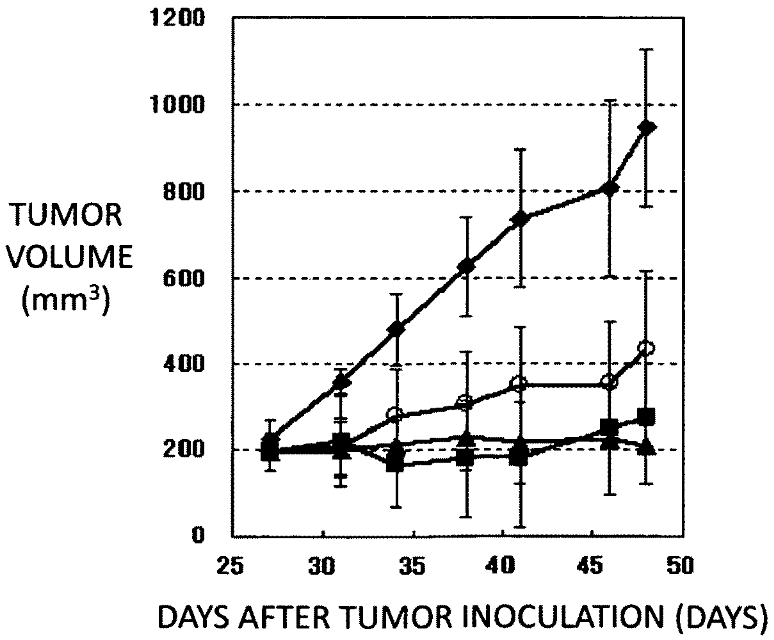

The antitumor activity of each test antibody was evaluated in the mouse model transplanted with human liver cancer. The tumor volume was measured at one week after the last day of the sample administration. The results are shown in FIG. 7. Hspd1.8Lspd1.6 (Hd1.8Ld1.6) antibody showed a stronger therapeutic efficacy, while the Hspu2.2Lspu2.2 (Hu2.2Lu2.2) antibody showed a weak therapeutic efficacy.

(6) Plasma Concentrations of the Test Antibodies

The concentration of the test antibody in murine plasma was measured by an ELISA-based method described in Example 1. Standard samples were prepared at the plasma concentration of 12.8, 6.4, 3.2, 1.6, 0.8, 0.4, and 0.2 μg/mL. The standard samples and the murine plasma test samples (suitably diluted to a desired concentration) were added to immunoplates (Nunc-ImmunoPlate, MaxiSorp (Nalge Nunc International)) on which soluble glypican 3 core (Chugai Seiyaku Kabushiki Kaisha) is immobilized, and the plates were incubated for 1 hour at room temperature. Goat Anti-Human IgG-BIOT (Southern Biotechnology Associates) and then streptavidin-alkaline phosphatase conjugate (Roche Diagnostics) were added and a chromogenic reaction was carried out using the BluePhos Microwell Phosphatase Substrates System (Kirkegaard & Perry Laboratories) as a substrate. Using a microplate reader, the color of the reaction solution in each well was determined by measuring the absorbance of the reaction solution at 650 nm. The murine plasma antibody concentration was then calculated using SOFTmax PRO analytical software (Molecular Devices) with reference to the standard curve prepared with the absorbance values obtained from the standard samples.

Figure 8:
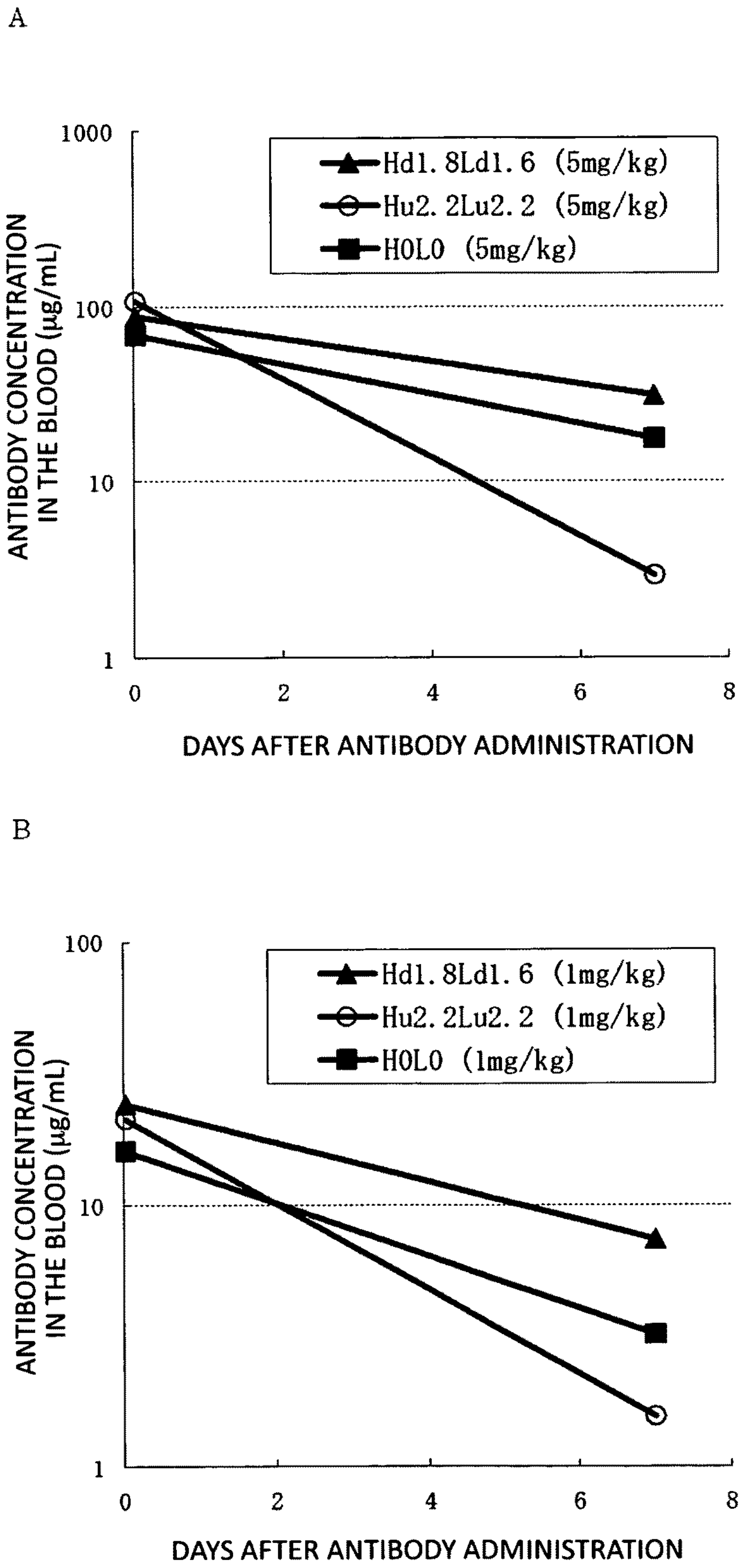
FIG. 8 shows the plasma concentrations of the antibody for the H0L0 antibody, Hspu2.2Lspu2.2 (Hu2.2Lu2.2) antibody, and Hspd1.8Lspd1.6 (Hd1.8Ld1.6) antibody in a human liver cancer-transplant mouse model.

The murine plasma concentrations after 30 minutes and 7 days from administration are shown in FIG. 8. A higher antibody concentration was observed in murine plasma after 7 days from administration of the test antibody having lower pI values for both administration doses tested.

Example 7

ADCC Activity of the Test Antibodies Measured Using Human Peripheral Blood Monocytes as the Effector Cell The ADCC activity of the test antibodies was tested as described below using a human peripheral blood monocyte (referred to as PBMC) as the effector cell).

(1) Preparation of a Human PBMC Solution

Using a syringe previously loaded with 200 μL, of a 1000 unit/mL heparin solution (Novo Heparin Injection 5000 Units, Novo Nordisk), 50 mL peripheral blood was collected from a healthy volunteer (adult male) from Chugai Seiyaku Kabushiki Kaisha. The blood was diluted twofold with PBS (−), divided into 4 equal parts, and introduced into a Leucosep lymphocyte separation tube (Greiner Bio-one) that was previously loaded with 15 mL Ficoll-Paque PLUS and subjected to centrifugation. The separation tube loaded with the peripheral blood was centrifuged for 10 minutes at room temperature at 2150 rpm, and the monocyte fraction layer was collected. The cells contained in the layer were washed once with Dulbecco's Modified Eagle's Medium (Sigma) containing 10% FBS (referred to below as 10% FBS/D-MEM) and suspended in 10% FBS/D-MEM at a cell density of $5\times10^6$/mL. The cell suspension was subjected to the following experiment as a human PBMC solution.

(2) Preparation of Target Cells

HepG2 cells were detached from a dish and seeded on a 96-well U-bottom plate at $1\times10^4$ cells/well. The plate was incubated overnight at 37° C. in a 5% $CO_2$ incubator. On the next day, 5.55 MBq Cr-51 was added to each well of the plate and the plate was incubated for 3 hours at 37° C. in a 5% $CO_2$ incubator. The HepG2 cells contained in the wells of the plate were used as target cells in the ADCC activity assay as described below.

(3) Chromium Release Assay (ADCC Activity)

The ADCC activity was evaluated from the specific chromium release rate determined by the chromium release method. The target cells prepared as in (2) were washed with the medium, and 100 μL of each antibody (H0L0 antibody, Hu2.2Lu2.2 antibody, or Hd1.8Ld1.6 antibody) was added at a concentration of 0, 0.004, 0.04, 0.4, 4, or 40 μg/mL. The plate was reacted for 15 minutes at room temperature, and the antibody solution was removed. 100 μL of subculture medium was added to each well and the plate was incubated for 1 hour at 37° C. in a 5% $CO_2$ incubator. 100 μL of the human PBMC solution prepared as in (1) was added to each well ($5\times10^5$ cells/well), and the plate was incubated for 4 hours at 37° C. in a 5% $CO_2$ incubator and centrifuged. The radioactivity in 100 μL of the culture supernatant in each well of the plate was measured by a gamma counter. The specific chromium release rate was determined according to the following formula. Specific chromium release rate (%)

$$(A-C)\times100/(B-C)$$

wherein A represents the mean value of the radioactivity (cpm) of the 100 μL culture supernatant in each well; B represents the mean value of the radioactivity (cpm) of the 100 μL culture supernatant in wells where 100 μL of 2% aqueous NP-40 solution (Nonidet P-40, Nacalai Tesque) and 50 μL of 10% FBS/D-MEM medium were added to the target cells; and C represents the mean value of the radioactivity (cpm) of the 100 μL culture supernatant in wells where 150 μL of 10% FBS/D-MEM medium was added to the target cells. The tests were carried out in triplicate, and the mean value and standard deviation of the specific chromium release rate (%), which is reflective of the ADCC activity of the antibody, were calculated form the test results.

(4) Evaluation of the ADCC Activity of the Test Antibodies

Figure 9:
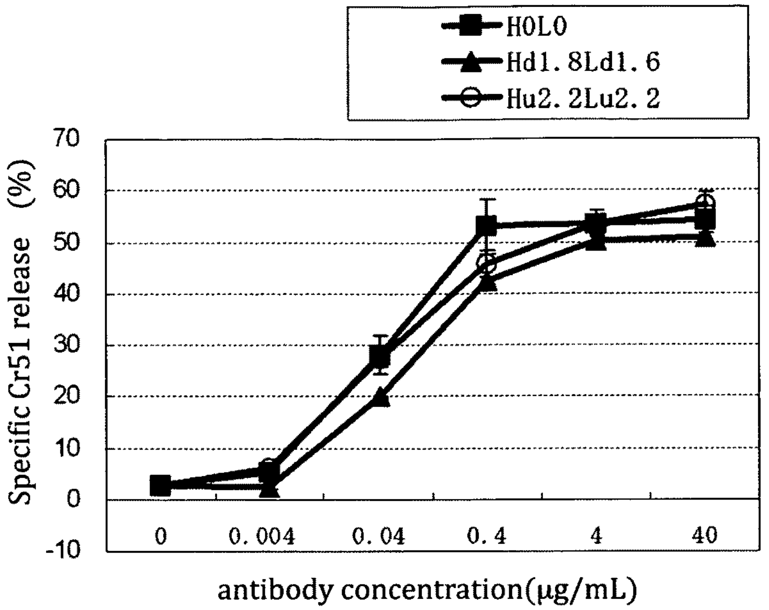
FIG. 9 shows the ADCC activity of test antibodies against HepG2 cells, a human liver cancer cell line, wherein the black triangle shows the ADCC activity by the Hspd1.8Lspd1.6 (Hd1.8Ld1.6) antibody, the white circle shows the ADCC activity by the Hspu2.2Lspu2.2 (Hu2.2Lu2.2) antibody, and the black square shows the ADCC activity by the H0L0 antibody.

The results of the evaluation of the ADCC activity exhibited by human PBMCs via the test antibody revealed that all of the test antibodies exhibited ADCC activity. The results are shown in FIG. 9. Significant difference test revealed that no significant difference was observed between test, antibodies at any concentrations tested in the specific chromium release rate of the test antibodies. The statistical analyses were run using the SAS Preclinical Package (SAS Institute Inc.). These results showed that there was no difference between the ADCC activities of the pI-modified test antibodies.

Example 8

Preparation and Characterization of pI Modified Antibody by Point Mutation (1) Selection of Modification Sites for Decreasing pI To improve the tumor suppression activity of the Hd1.8Ld1.6 antibody, modification sites were selected for the ability of decreasing in the pI value of the variable region. Amino acid residues involving the decrease in the pI value of the variable region were found, which are summarized in Table 2 (heavy chain) and Table 3 (light chain). Specific examples of these modifications for decreasing the pI value are pH7pL14 antibody and pH7pL16 antibody. These pI modification antibodies were prepared as follows.

The modification sites were created by Assemble PCR. Oligo DNAs designed based on the sense and antisense sequences containing the modification site were synthesized. A pair of an antisense oligo DNA containing the modification site and a sense oligo DNA corresponding to the vector bearing the gene to be modified, or a pair of a sense oligo DNA containing the modification site and an antisense oligo DNA corresponding to the vector bearing the gene to be modified was used in PCR with PrimeSTAR (TAKARA) to obtain 5'-side and 3'-side fragments containing the modification site. The two fragments were linked using Assemble PCR to prepare each mutant.

The mutant thus obtained was inserted into an expression vector which allows for expression of the inserted gene in animal cells. The nucleotide sequence of the expression vector was determined by a method known in the art. Introduction of the point mutation was confirmed by the nucleotide sequence of the plasmid DNA. The gene containing the point mutation was cloned into an expression vector which allows for expression of the inserted gene in animal cells. The expression and purification of the antibody was according to the method described in Example 1 or a similar method.

Starting from Hd1.8, the 61st glutamine (Q) (according to the Kabat numbering) present in CDR1 of Hd1.8 was substituted with glutamic acid (E) to prepare pH7 (SEQ ID NO:27). Starting from Ld1.6, the 24th arginine (R) (according to the Kabat numbering) present in CDR1 of Ld1.6 was substituted with glutamine (Q), the 37th glutamine (Q) was substituted with leucine (L), the 43rd alanine (A) was substituted with serine (S), the 45th arginine (R) was substituted with glutamine (Q), the 74th threonine (T) was substituted with lysine (K), the 77th serine (S) was substituted with arginine (R), the 78th leucine (L) was substituted with valine (V), and the 79th glutamine (Q) was substituted with glutamic acid (E), each present in FR2 and FR3, to prepare pL14 (SEQ ID NO:28).

Starting from pL14, the 104th leucine (L) (according to the Kabat numbering) was substituted with valine (V), the 107th lysine (K) was substituted with glutamic acid (E), each present in FR4 of pL14, to prepare pL16 (SEQ ID NO:29).

(2) Measurement of pI Value of Point Mutation pI Modified Antibodies

The pI values of the Hd1.8Ld1.6 antibody, pH7pL14 antibody and pH7pL16 antibody were measured by electrophoresis with PhastGel IEF 4-6.5 (GE Healthcase) using the method described in Example 1 or similar method. The pI value of Hd1.8Ld1.6 antibody, pH7pL14 antibody and pH7pL16 antibody was 7.47, 7.07 and 6.52, respectively, indicating that the pI values of pH7pL14 antibody and pH7pL16 antibody were lower than that of the Hd1.8Ld1.6 antibody by 0.4 and 0.95, respectively.

(3) Measurement of Tm Value of Point Mutation pI Modified Antibodies

The Tm values of Fabs obtained from Hd1.8Ld1.6 antibody, pH7pL14 antibody and pH7pL16 antibody were measured with VP-DSC (Micro Cal) using the method similar to Example 1. In this experiment, PBS was used as a dialysis solution, and the antibody concentration in the test solution for DSC measurement was adjusted to 25-100 μg/ml. DSC scanning was set from 20° C. to 115 ° C. at the scanning rate of about 4K/min, with the reference solution (dialysis solution) and DSC measurement test solution. The thermal denaturation midpoint temperature of the Fabs of the Hd1.8Ld1.6 antibody, pH7pL14 antibody and pH7pL16 antibody was 77.5, 78.0 and 74.7 ° C., respectively.

Figure 10:
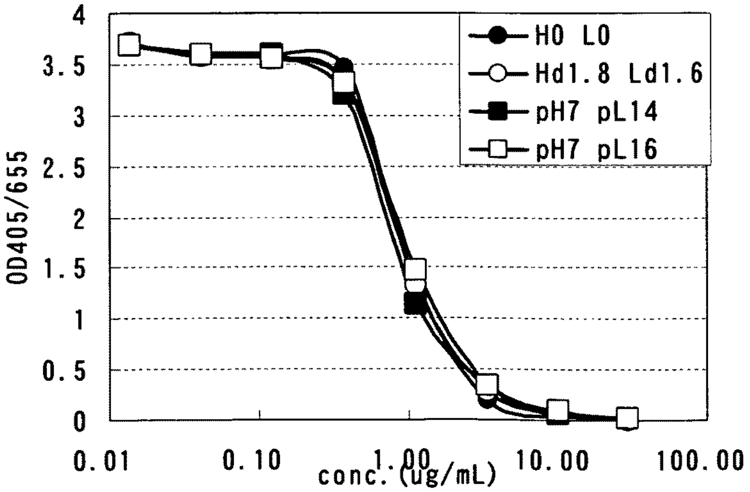
FIG. 10 shows the binding affinity of the H0L0 antibody, Hd1.8Ld1.6 antibody, pH7pL14 antibody and pH7pL16 antibody for the antigen glypican 3 measured by a competitive ELISA, wherein the black circle shows the binding activity of the H0L0 antibody, the white circle shows the binding activity of the Hd1.8Ld1.6 antibody, the black square shows the binding activity of the pH7pL14 antibody, and the white square shows the binding activity of the pH7pL16 antibody.

(4) Evaluation of Binding Activity to Antigen of Point Mutation pI Modified Antibodies by Competitive ELISA The binding activity to the antigen glypican 3 of each point mutation pI modified antibody was measured using the method described in Example 1 (FIG. 10). The binding activity to glypican 3 of the pH7pH14 antibody and pH7pL16 antibody was shown to be comparative to that of the H0L0 antibody.

Example 9

Preparation of Point Mutation pI Modified Antibody Using FTP-KO Cell Line

The expression vector carrying the gene coding for each point mutation pI modified antibody prepared in Example 8 was introduced into the cells of FTP-KO cell line prepared in Reference Example 2 using Polyethylenimine (Polysciences Inc.), and the antibody was expressed. The modified antibody was purified from the cell culture supernatant using rProtein A Sepharose™ Fast Flow (Amersham Biosciences). The purified antibody solution was prepared according to the method described in Example 5 and the antibody concentration was measured.

Example 10

Therapeutic Efficacy in an In Vivo Model of Humanized GC33 Antibody and Point Mutation pI Modified Antibodies (1) Maintenance of the Cell Line Used for Transplantation Into the In Vivo Model Hep G2 cells (ATCC) were used. The Hep G2 cells were maintained by subculture in Minimun Essential Medium Eagle medium (SIGMA) supplemented with 10% FBS, 1 mmol/1 MEM Sodium Pyruvate (Invitrogen), and 1 mmol/1 MEM non-essential amino acids (Invitrogen) (referred to as the subculture medium).

(2) Preparation of HepG2 Cell-Transplanted Mouse Model

Using a solution containing subculture medium and MATRIGEL Matrix (BD Bioscience) at 1:1, a suspension of HepG2 cells was prepared at $5\times10^7$ cells/mL. 100 μL of the cell suspension ($5\times10^6$ cells/mouse) was transplanted subcutaneously in the abdominal region of SCID mice (male, 5 week old, CLEA Japan, Inc.). On the day prior to cell transplantation, the mice received 100 μL anti-asialo GM1 antibody (content of 1 vial was dissolved in 5 mL of the solution, Wako Pure Chemical Industries, Ltd.) by interperitoreal administration. The tumor volume was calculated according to the following formula.

$$\text{tumor volume}=\text{long diameter}\times\text{short diameter}\times\text{short diameter}/2$$

When the average tumor volume reached 400 $mm^3$, the mouse was used as a model.

(3) Preparation of Administration Sample Containing the Test Antibody

The administration samples containing H0L0 antibody, Hd1.8Ld1.6 antibody, pH7pL14 antibody or pH7pL16 antibody at 0.1 mg/mL (1 mg/kg group) were prepared with physiological saline on the day of administration.

(4) Administration of the Antibody-Containing Administration Sample

The administration sample prepared according to (3) was administered at a dose of 10 mL/kg through the tail vein to the mouse model prepared in (2) at once per week for five weeks beginning 34 days after HepG2 cell transplantation. As a negative control, physiological saline was administered at a dose of 10 mL/kg through the tail vein at once per week for five weeks. All the groups contained 5 animals, and a each test antibody-containing administration sample was administered to a respective group. At about the same time as the administration, venous blood was collected from 3 animals in each group and was analyzed for the murine plasma concentration of the antibody. Specifically, blood was collected from a dorsal foot vein at two time points: 0.5 hour after the initial administration and immediately before the second administration. 20 μL collected blood was treated with heparin and the plasma was isolated by centrifugation.

(5) Evaluation of the Antitumor Activity of the Test Antibodies

Figure 11:
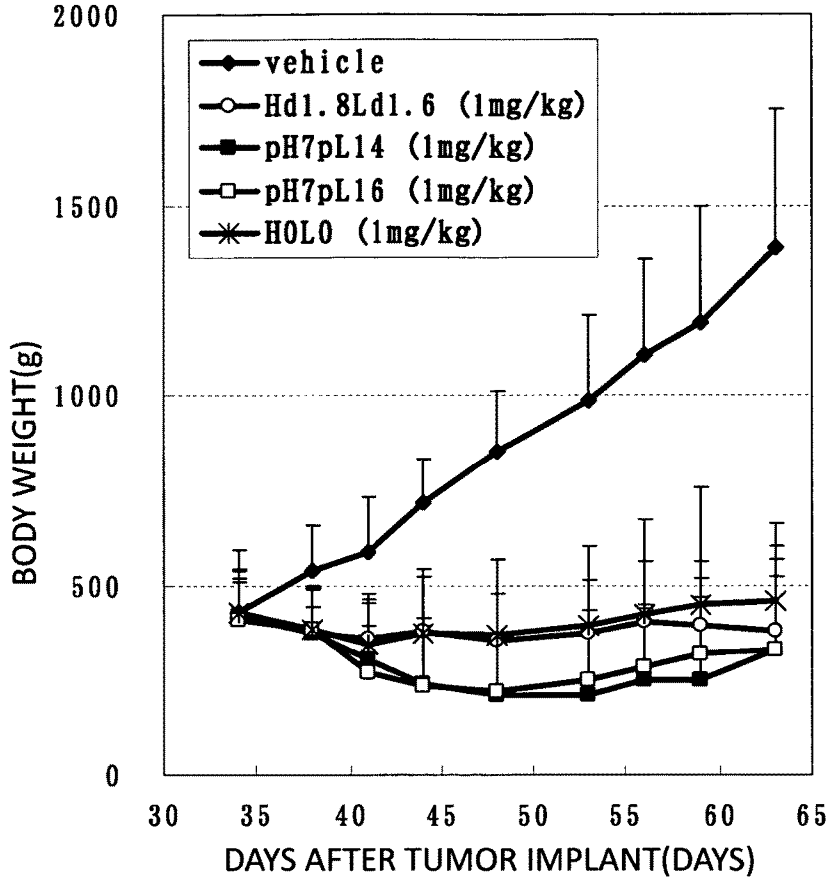
FIG. 11 shows the antitumor activity of the H0L0 antibody, pH7pL14 antibody and pH7pL16 antibody in a mouse model implanted with human hepatic cancer, wherein * shows the antitumor activity of the H0L0 antibody, the white circle shows the antitumor activity of the Hd1.8Ld1.6 antibody, the black square shows the antitumor activity of the pH7pL14 antibody, and the white square shows the antitumor activity of the pH7pL16 antibody.

The antitumor activity of each test antibody was evaluated in the mouse model transplanted with human liver cancer. The tumor volume was measured at one week after the last day of the sample administration. As shown in FIG. 11, a stronger therapeutic efficacy was found in pH7pL14 antibody and pH7pL16 antibody compared to H0L0 antibody and Hd1.8Ld1.6 antibody.

Example 11

The PK Test of Humanized GC33 Antibody and Point Mutation Antibodies Using In Vivo Model (1) Preparation of Test Antibody-Containing Administration Sample The administration samples containing H0L0 antibody, Hd1.8Ld1.6 antibody, pH7pL14 antibody, pH7pL16 antibody or pH7M85pL16 antibody at 0.5 mg/mL (5 mg/kg group) were prepared with physiological saline on the day of administration.

(2) Administration of the Antibody-Containing Administration Sample

The administration sample prepared according to (1) was administered at a dose of 10 mL/kg through the tail vein to the C.B-17/Icr-scid mouse. All the groups contained 3 animals, and each test antibody-containing administration sample was administered to a respective group. Venous blood was collected from the animals and was analyzed for the murine plasma concentration of the antibody. Specifically, blood was collected from a dorsal foot vein at seven time points: 0.5 hours, 2 hours, 8 hours, 24 hours, 72 hours, 168 hours after the initial administration. 20 μL of collected blood was treated with heparin and the plasma was isolated by centrifugation.

(3) Plasma Concentrations of the Test Antibodies

The concentration of the test antibody in murine plasma was measured by an ELISA-based method described in Example 6. Standard samples were prepared at a plasma concentration of 12.8, 6.4, 3.2, 1.6, 0.8, 0.4, and 0.2 μg/mL. The standard samples and the murine plasma test samples (suitably diluted to a desired concentration) were added to immunoplates (Nunc-ImmunoPlate, MaxiSorp (Nalge Nunc International)) on which soluble glypican 3 core (Chugai Seiyaku Kabushiki Kaisha) is immobilized, and the plates were incubated for 1 hour at room temperature. Goat Anti-Human IgG-BIOT (Southern Biotechnology Associates) and then streptavidin-alkaline phosphatase conjugate (Roche Diagnostics) were added, and a chromogenic reaction was carried out using the BluePhos Microwell Phosphatase Substrates System (Kirkegaard & Perry Laboratories) as a substrate. Using a microplate reader, the color of the reaction solution in each well was determined by measuring the absorbance of the reaction solution at 650 nm. The murine plasma antibody concentration was then calculated using SOFTmax PRO analytical software (Molecular Devices) with reference to the standard curve prepared with the absorbance values obtained from the standard samples.

Figure 12:
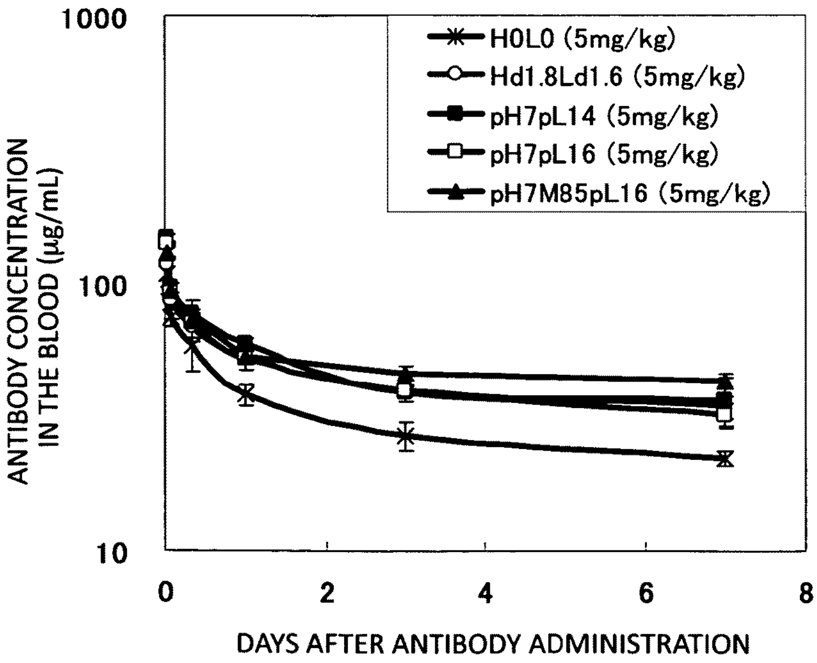
FIG. 12 shows the plasma concentration of the antibody for the H0L0 antibody, Hd1.8Ld1.6 antibody, pH7pL14 antibody, pH7pL16 antibody and pH7M85pL16 in mice, wherein * shows the plasma concentration of the H0L0 antibody, the white circle shows the plasma concentration of the Hd1.8Ld1.6 antibody, the black square shows the plasma concentration of the pH7pL14 antibody, the white square shows the plasma concentration of the pH7pL16 antibody, the black triangle shows the plasma concentration of the pH7M85pL16 in mouse.

The murine plasma concentrations after administration are shown in FIG. 12. A higher antibody concentration was observed in the plasma of mice that received the test antibody having lower pI value.

Example 12

ADCC Activity of the Test Antibodies Using Human Peripheral Blood Monocytes as the Effector Cell The ADCC activity of the test antibodies was tested as described below using a human peripheral blood monocyte (referred to as PBMC) as the effector cell).

(1) Preparation of a Human PBMC Solution

Using a syringe previously loaded with 200 μL of a 1000 unit/mL heparin solution (Novo Heparin Injection 5000 Units, Novo Nordisk), 50 mL peripheral blood was collected from a healthy volunteer (adult male) from Chugai Seiyaku Kabushiki Kaisha. The blood was diluted twofold with PBS (−), divided into 4 equal parts and introduced into a Leucosep lymphocyte separation tube (Greiner Bio-one) that was previously loaded with 15 mL Ficoll-Paque PLUS and subjected to centrifugation. The separation tube loaded with the peripheral blood was centrifuged for 10 minutes at room temperature at 2150 rpm, and the monocyte fraction layer was collected. The cells contained in the layer were washed once with Dulbecco's Modified Eagle's Medium (Sigma) containing 10% FBS (referred to below as 10% FBS/D-MEM) and suspended in 10% FBS/D-MEM at a cell density of $5\times10^6$/mL. The cell suspension was subjected to the following experiment as a human PBMC solution.

(2) Preparation of Target Cells

HepG2 cells were detached from a dish and seeded on a 96-well U-bottom plate at $1\times10^4$ cells/well. The plate was incubated overnight at 37° C. in a 5% CO2 incubator. On the next day, 5.55 MBq Cr-51 was added to each well of the plate and the plate was incubated for 3 hours at 37° C. in a 5% CO2 incubator. The HepG2 cells contained in the wells of the plate were used as target cells in the ADCC activity assay as described below.

(3) Chromium Release Assay (ADCC Activity)

The ADCC activity was evaluated from the specific chromium release rate determined by the chromium release method. The target cells prepared as in (2) were washed with medium, and 100 μL of each antibody (H0L0 antibody, Hd1.8Ld1.6 antibody, pH7pL14 antibody or pH7pL16 antibody) was added at a concentration of 0, 0.004, 0.04, 0.4, 4, or 40 μg/mL. The plate was reacted for 15 minutes at room temperature, and the antibody solution was removed. 100 μL of subculture medium was added to each well and the plate was incubated for 1 hour at 37° C. in a 5% $CO_2$ incubator. 100 μL of the human PBMC solution prepared as in (1) was added to each well ($5\times10^5$ cells/well) and the plate was incubated for 4 hours at 37° C. in a 5% $CO_2$ incubator, and centrifuged. The radioactivity in 100 μL of the culture supernatant in each well of the plate was measured by a gamma counter. The specific chromium release rate was determined according to the following formula. Specific chromium release rate (%)=(A−C)×100/(B−C) wherein A represents the mean value of the radioactivity (cpm) of the 100 μL culture supernatant in each well; B represents the mean value of the radioactivity (cpm) of the 100 μL culture supernatant in wells where 100 μL of 2% aqueous NP-40 solution (Nonidet P-40, Nacalai Tesque) and 50 μL of 10% FBS/D-MEM medium were added to the target cells; and C represents the mean value of the radioactivity (cpm) of the 100 μL culture supernatant in wells where 150 μL of 10% FBS/D-MEM medium was added to the target cells. The tests were carried out in triplicate, and the mean value and standard deviation of the specific chromium release rate (%), which is reflective of the ADCC activity of the antibody, were calculated from the test results.

(4) Evaluation of the ADCC Activity of the Test Antibodies

Figure 13:
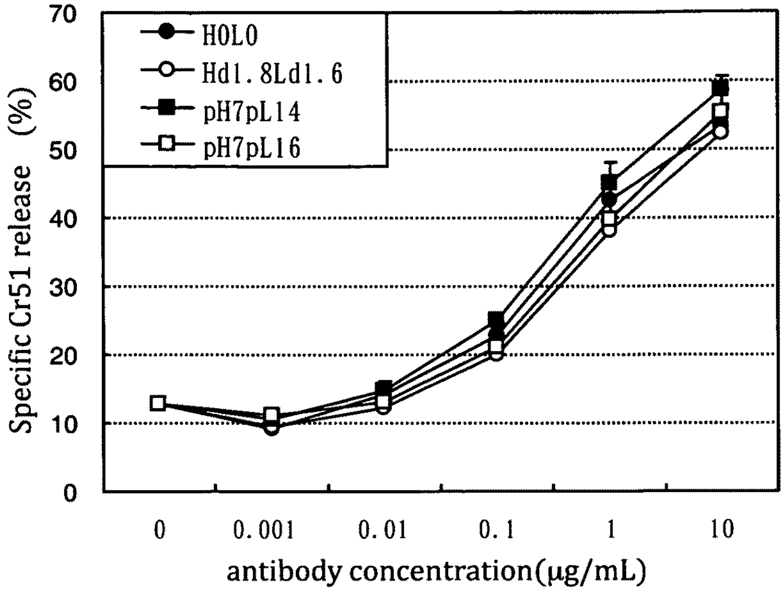
FIG. 13 shows the ADCC activity by H0L0 antibody, Hd1.8Ld1.6 antibody, pH7pL14 antibody, and pH7pL16 antibody against HepG2 cells, a human liver cancer cell line, wherein the black circle shows the ADCC activity by the H0L0 antibody, the white circle the ADCC activity by the Hd1.8Ld1.6 antibody, the black square the ADCC activity by the pH7pL14 antibody, and the white square the ADCC activity by the pH7pL16 antibody.

The results of the evaluation of the ADCC activity exhibited by human PBMCs via the test antibody reveled that all of the test antibodies exhibited ADCC activity. The results are shown in FIG. 13. Significant difference test revealed that no significant difference was observed at any concentrations tested between test antibodies and the control H0L0 antibody in the specific chromium release rate of the antibodies. The statistical analyses were run using the SAS Preclinical Package (SAS Institute Inc.). These results showed that there was no difference between the ADCC activities of the pI-modified test antibodies.

Example 13

Preparation and Evaluation of Modified Antibodies Capable of Decreasing in the pI Value of the Constant Region (1) Selection of Modification Sites for Decreasing the pI Value of the Constant Region IgG1ΔGK (SEQ ID NO:32) is the IgG1 constant region having the amino acid sequence as shown in SEQ ID NO:31, which lacks the 446th Gly and the 447th Lys (according to the EU numbering) of the IgG1 constant region. Deletion of these two amino acid residues allows for the decrease in heterogeneity caused by the heavy chain terminal constant region of an antibody.

The antibody was modified to have decreased pI value in the constant region by substituting some of the amino acid residues in IgG1ΔGK with the corresponding amino acid residues in the sequence of the human IgG4 constant region according to the EU numbering.

Specifically, the 268th histidine (H) of IgG1ΔGK (according to the EU numbering) was substituted with glutamine (Q) of the IgG4 sequence, the 274th lysine (K) was substituted with glutamine (Q), the 355th arginine (R) was substituted with glutamine (Q), the 356th aspartic acid (D) was substituted with glutamic acid (E), the 358th leucine (L) was substituted with methionine (M), and the 419th glutamine (Q) was substituted with glutamic acid (E). These substitutions contain sequence of 9-12 amino acids which can serve as a T-cell epitope only derived from a human constant region and thus are expected to have lower risk of immunogenicity. These 6 modifications were introduced into IgG1ΔGK to obtain M85 (SEQ ID NO:33).

The constant region M85 was combined with the variable region pH7 and H0to prepare pH7M85 (SEQ ID NO:34) and HOM85 (SEQ ID NO:35), respectively. HOM85L0 antibody was prepared from H0M85 as the heavy chain and L0 as the light chain, and pH7M85pL16 antibody was prepared from pH7M85 as the heavy chain and pL16 as the light light chain. Also, the H0L0 antibody and pH7pL16 antibody having the constant region of IgG1 were prepared as in Example 1 and Example 8. The antibodies HOM85LO, pH7M85pL16, H0L0, and pH7pL16 were expressed in FTP-KO cell line or HEK293 cells, and purified as described in Example 1 or 9.

(2) Measurement of pI Value of Vonstant Region pI Modified Antibodies

The pI value of the H0L0 antibody, HOM85L0 antibody, pH7pL16 antibody, and pH7M85pL16 antibody was measured by electrophoresis with PhastGel IEF 4-6.5 (GE Healthcase) under the same electrophoresis conditions using the method similar to that described in Example 1. The pI values of the H0L0 antibody, HOM85L0 antibody, pH7pL16 antibody and pH7M85pL16 antibody was 8.85, 8.16, 6.52 and 5.78, respectively, indicating that the modification in the constant region contributes to further decrease in the pI value without affecting to the immunogenicity of the antibody.

Figure 14:
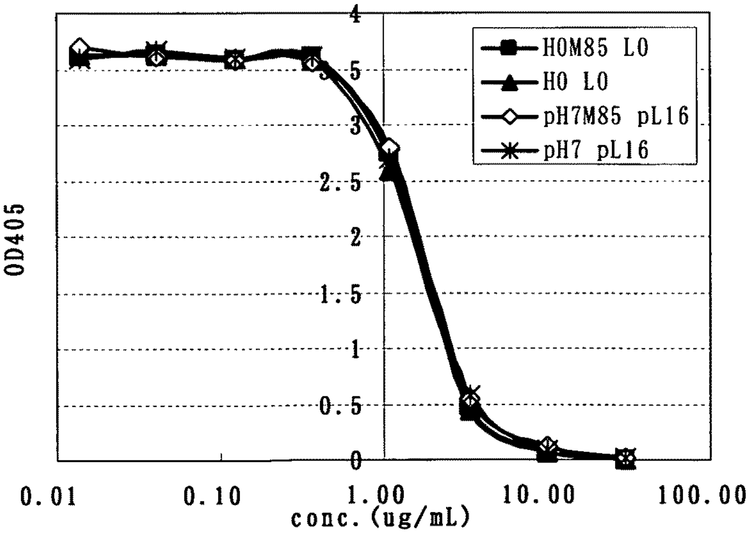
FIG. 14 shows the binding affinity of the H0L0 antibody, H0M85L0 antibody, pH7pL16 antibody and pH7M85pL16 antibody for the antigen glypican 3 measured by a competitive ELISA, wherein the black triangle shows the binding activity of the H0L0 antibody, the black square shows the binding activity of the H0M85L0 antibody, * shows the binding activity of the pH7pL16 antibody, and the white diamond shows the binding activity of the pH7M85pL16 antibody.

(3) Evaluation of Binding Activity of Constant Region pI Modified Antibodies by Competitive ELISA The binding activity to the antigen of each constant region pI modified antibody was measured using the method described in Example 1 (FIG. 14). The binding activity to glypican 3 of the H0L0 antibody, HOM85L0 antibody, pH7pL16 antibody, pH7M85pL16 antibody were shown to be about the same.

Example 14

Figure 15:
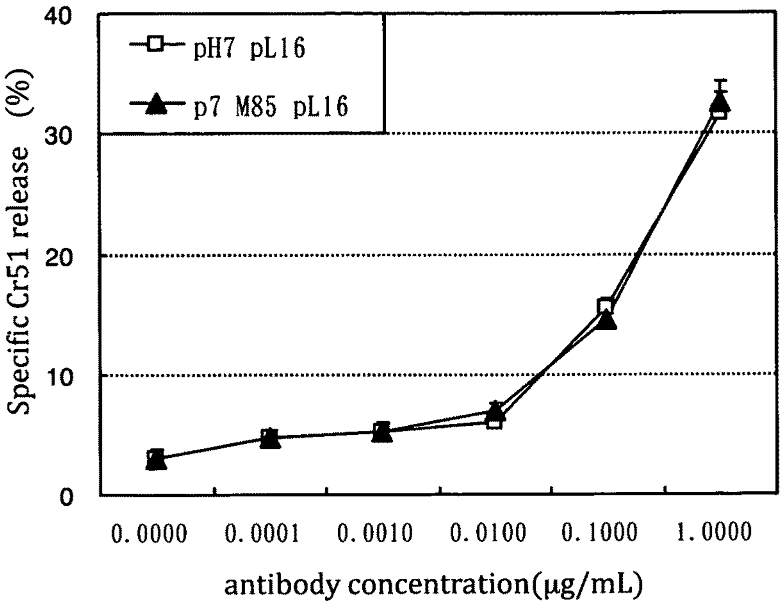
FIG. 15 shows the ADCC activity by the pH7pL16 antibody and pH7M85pL16 antibody against HepG2 cells, a human liver cancer cell line, wherein the white square shows the ADCC activity by the pH7pL16 antibody, and the black triangle shows the ADCC activity by the pH7M85pL16 antibody.

ADCC Activity of the Constant Region pI Modified Antibodies Using Human Peripheral Blood Monocytes as the Effector Cell The ADCC activity of the pH7pL16 antibody and pH7M85pL16 antibody was tested using the method as described in Example 12. The results are shown in FIG. 15. Significant difference test revealed that no significant difference was observed between test antibodies at any concentrations tested in the specific chromium release rate of the test antibodies. The statistical analyses were run using the SAS Preclinical Package (SAS Institute Inc.). These results showed that there was no difference between the ADCC activities of the pH7pL16 antibody and pH7M85pL16 antibody.

The invention claimed is:

1. An isolated anti-glypican 3 antibody which comprises a heavy chain variable region shown in SEQ ID NO: 27 and a light chain variable region shown in SEQ ID NO: 29.

2. The antibody according to claim 1, comprising a constant region of a human antibody.

3. The antibody according to claim 2, wherein the constant region comprises a sequence shown in SEQ ID NO: 32 or SEQ ID NO: 33.

4. The antibody according to claim 1, wherein the antibody has a reduced content of fucose attached to the Fc region of the antibody in comparison with the antibody which has a wild-type human Fc region.

5. A composition comprising the antibody according to any one of claims 2-4 and a pharmaceutically acceptable carrier.

6. An anticancer agent comprising as an active ingredient the antibody according to anyone of claims 2-4, wherein the cancer expresses glypican-3.

7. The anticancer agent according to claim 6, wherein the cancer is liver cancer.

8. An isolated nucleic acid that encodes a heavy or light chain variable region polypeptide of the antibody according to anyone of claims 2- 4.

9. An isolated host cell comprising the nucleic acid according to claim 8.

10. The host cell according to claim 9, wherein the host cell is a fucose transporter-deficient animal cell, a fucosyltransferase-deleted animal cell, or an animal cell in which a complex branched sugar chain modification is modified.

11. A method for preparing an antibody comprising culturing the host cell according to claim 9 and recovering the antibody from the cell culture.

12. A method for treating a cancer comprising administering to a subject in need of such treatment the antibody according to any one of claims 2-4, wherein the cancer expresses glypican-3.

13. The method according to claim 12, wherein the cancer is liver cancer.

14. A method for treating a cancer comprising administering to a subject in need of such treatment the composition according to claim 5, wherein the cancer expresses glypican-3.

15. The method according to claim 14, wherein the cancer is liver cancer.

16. A method for preparing an antibody comprising culturing the host cell according to claim 10 and recovering the antibody from the cell culture.

* * * * *

SEQUENCE LISTING

```
<160> NUMBER OF SEQ ID NOS: 35

<210> SEQ ID NO 1
<211> LENGTH: 115
<212> TYPE: PRT
<213> ORGANISM: Artificial Sequence
<220> FEATURE:
<223> OTHER INFORMATION: Humanized antibody H chain

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115


<210> SEQ ID NO 2
<211> LENGTH: 115
<212> TYPE: PRT
<213> ORGANISM: Artificial Sequence
<220> FEATURE:
<223> OTHER INFORMATION: Humanized antibody H chain

<400> SEQUENCE: 2

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Asp Tyr
            20                  25                  30

Glu Met His Trp Ile Arg Gln Pro Pro Gly Gln Gly Leu Glu Trp Ile
        35                  40                  45

Gly Ala Ile Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115


<210> SEQ ID NO 3
<211> LENGTH: 115
<212> TYPE: PRT
<213> ORGANISM: Artificial Sequence
<220> FEATURE:
<223> OTHER INFORMATION: Humanized antibody H chain

<400> SEQUENCE: 3

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Val Arg Gln Ala Pro Gly Glu Gly Leu Glu Trp Met
        35                  40                  45

Gly Ala Leu Asp Pro Lys Thr Gly Asp Thr Ala Tyr Ser Gln Ser Phe
    50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115


<210> SEQ ID NO 4
<211> LENGTH: 115
<212> TYPE: PRT
<213> ORGANISM: Artificial Sequence
<220> FEATURE:
<223> OTHER INFORMATION: Humanized antibody H chain

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Lys Gly Leu Glu Trp Met
        35                  40                  45

Gly Ala Leu Asn Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80
```

```
Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Arg Gly Thr Leu Val Thr
            100                 105                 110

Val Ser Ser
        115


<210> SEQ ID NO 5
<211> LENGTH: 115
<212> TYPE: PRT
<213> ORGANISM: Artificial Sequence
<220> FEATURE:
<223> OTHER INFORMATION: Humanized antibody H chain

<400> SEQUENCE: 5

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Glu Gly Leu Glu Trp Ile
        35                  40                  45

Gly Ala Ile Asp Pro Lys Thr Gly Asp Thr Ala Tyr Ser Gln Ser Phe
    50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115


<210> SEQ ID NO 6
<211> LENGTH: 115
<212> TYPE: PRT
<213> ORGANISM: Artificial Sequence
<220> FEATURE:
<223> OTHER INFORMATION: Humanized antibody H chain

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Ile Arg Gln Pro Pro Gly Lys Gly Leu Glu Trp Ile
        35                  40                  45

Gly Ala Ile Asn Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Arg Gly Thr Leu Val Thr
            100                 105                 110

Val Ser Ser
        115


<210> SEQ ID NO 7
<211> LENGTH: 112
```

<212> TYPE: PRT
<213> ORGANISM: Artificial Sequence
<220> FEATURE:
<223> OTHER INFORMATION: Humanized antibody L chain

<400> SEQUENCE: 7

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110
```

<210> SEQ ID NO 8
<211> LENGTH: 112
<212> TYPE: PRT
<213> ORGANISM: Artificial Sequence
<220> FEATURE:
<223> OTHER INFORMATION: Humanized antibody L chain

<400> SEQUENCE: 8

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110
```

<210> SEQ ID NO 9
<211> LENGTH: 112
<212> TYPE: PRT
<213> ORGANISM: Artificial Sequence
<220> FEATURE:
<223> OTHER INFORMATION: Humanized antibody L chain

<400> SEQUENCE: 9

```
Asp Val Val Met Thr Gln Ser Pro Leu Ser Leu Pro Val Thr Pro Gly
1               5                   10                  15

Glu Pro Ala Ser Ile Ser Cys Arg Ala Ser Glu Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60
```

```
Asp Arg Phe Ser Gly Ser Gly Ser Gly Thr Asp Phe Thr Leu Thr Ile
65                  70                  75                  80

Ser Ser Leu Gln Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110


<210> SEQ ID NO 10
<211> LENGTH: 112
<212> TYPE: PRT
<213> ORGANISM: Artificial Sequence
<220> FEATURE:
<223> OTHER INFORMATION: Humanized antibody L chain

<400> SEQUENCE: 10

Asp Val Val Met Thr Gln Ser Pro Leu Ser Leu Pro Val Thr Pro Gly
1               5                   10                  15

Gln Pro Ala Ser Ile Ser Cys Arg Ala Ser Arg Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Arg Gly Thr Lys Leu Glu Ile Lys
            100                 105                 110


<210> SEQ ID NO 11
<211> LENGTH: 112
<212> TYPE: PRT
<213> ORGANISM: Artificial Sequence
<220> FEATURE:
<223> OTHER INFORMATION: Humanized antibody L chain

<400> SEQUENCE: 11

Asp Ile Val Met Thr Gln Ser Pro Leu Ser Leu Pro Val Thr Pro Gly
1               5                   10                  15

Glu Pro Ala Ser Ile Ser Cys Arg Ala Ser Glu Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110


<210> SEQ ID NO 12
<211> LENGTH: 112
<212> TYPE: PRT
<213> ORGANISM: Artificial Sequence
<220> FEATURE:
<223> OTHER INFORMATION: Humanized antibody L chain
```

<400> SEQUENCE: 12

Asp Ile Val Met Thr Gln Ser Pro Leu Ser Leu Pro Val Thr Pro Gly
1 5 10 15

Gln Pro Ala Ser Ile Ser Cys Arg Ala Ser Arg Ser Leu Val His Ser
20 25 30

Asn Arg Asn Thr Tyr Leu His Trp Tyr Gln Gln Lys Pro Gly Gln Ala
35 40 45

Pro Arg Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ser Gln Asn
85 90 95

Thr His Val Pro Pro Thr Phe Gly Arg Gly Thr Lys Leu Glu Ile Lys
100 105 110

<210> SEQ ID NO 13
<211> LENGTH: 545
<212> TYPE: PRT
<213> ORGANISM: homo sapiens

<400> SEQUENCE: 13

Gln Pro Pro Pro Pro Pro Pro Asp Ala Thr Cys His Gln Val Arg Ser
1 5 10 15

Phe Phe Gln Arg Leu Gln Pro Gly Leu Lys Trp Val Pro Glu Thr Pro
20 25 30

Val Pro Gly Ser Asp Leu Gln Val Cys Leu Pro Lys Gly Pro Thr Cys
35 40 45

Cys Ser Arg Lys Met Glu Glu Lys Tyr Gln Leu Thr Ala Arg Leu Asn
50 55 60

Met Glu Gln Leu Leu Gln Ser Ala Ser Met Glu Leu Lys Phe Leu Ile
65 70 75 80

Ile Gln Asn Ala Ala Val Phe Gln Glu Ala Phe Glu Ile Val Val Arg
85 90 95

His Ala Lys Asn Tyr Thr Asn Ala Met Phe Lys Asn Asn Tyr Pro Ser
100 105 110

Leu Thr Pro Gln Ala Phe Glu Phe Val Gly Glu Phe Phe Thr Asp Val
115 120 125

Ser Leu Tyr Ile Leu Gly Ser Asp Ile Asn Val Asp Asp Met Val Asn
130 135 140

Glu Leu Phe Asp Ser Leu Phe Pro Val Ile Tyr Thr Gln Leu Met Asn
145 150 155 160

Pro Gly Leu Pro Asp Ser Ala Leu Asp Ile Asn Glu Cys Leu Arg Gly
165 170 175

Ala Arg Arg Asp Leu Lys Val Phe Gly Asn Phe Pro Lys Leu Ile Met
180 185 190

Thr Gln Val Ser Lys Ser Leu Gln Val Thr Arg Ile Phe Leu Gln Ala
195 200 205

Leu Asn Leu Gly Ile Glu Val Ile Asn Thr Thr Asp His Leu Lys Phe
210 215 220

Ser Lys Asp Cys Gly Arg Met Leu Thr Arg Met Trp Tyr Cys Ser Tyr
225 230 235 240

Cys Gln Gly Leu Met Met Val Lys Pro Cys Gly Gly Tyr Cys Asn Val
245 250 255

Val Met Gln Gly Cys Met Ala Gly Val Val Glu Ile Asp Lys Tyr Trp

-continued

```
            260                 265                 270

Arg Glu Tyr Ile Leu Ser Leu Glu Glu Leu Val Asn Gly Met Tyr Arg
        275                 280                 285

Ile Tyr Asp Met Glu Asn Val Leu Leu Gly Leu Phe Ser Thr Ile His
    290                 295                 300

Asp Ser Ile Gln Tyr Val Gln Lys Asn Ala Gly Lys Leu Thr Thr Thr
305                 310                 315                 320

Ile Gly Lys Leu Cys Ala His Ser Gln Gln Arg Gln Tyr Arg Ser Ala
                325                 330                 335

Tyr Tyr Pro Glu Asp Leu Phe Ile Asp Lys Lys Val Leu Lys Val Ala
            340                 345                 350

His Val Glu His Glu Glu Thr Leu Ser Ser Arg Arg Arg Glu Leu Ile
        355                 360                 365

Gln Lys Leu Lys Ser Phe Ile Ser Phe Tyr Ser Ala Leu Pro Gly Tyr
    370                 375                 380

Ile Cys Ser His Ser Pro Val Ala Glu Asn Asp Thr Leu Cys Trp Asn
385                 390                 395                 400

Gly Gln Glu Leu Val Glu Arg Tyr Ser Gln Lys Ala Ala Arg Asn Gly
                405                 410                 415

Met Lys Asn Gln Phe Asn Leu His Glu Leu Lys Met Lys Gly Pro Glu
            420                 425                 430

Pro Val Val Ser Gln Ile Ile Asp Lys Leu Lys His Ile Asn Gln Leu
        435                 440                 445

Leu Arg Thr Met Ser Met Pro Lys Gly Arg Val Leu Asp Lys Asn Leu
    450                 455                 460

Asp Glu Glu Gly Phe Glu Ala Gly Asp Cys Gly Asp Asp Glu Asp Glu
465                 470                 475                 480

Cys Ile Gly Gly Ala Gly Asp Gly Met Ile Lys Val Lys Asn Gln Leu
                485                 490                 495

Arg Phe Leu Ala Glu Leu Ala Tyr Asp Leu Asp Val Asp Asp Ala Pro
            500                 505                 510

Gly Asn Ser Gln Gln Ala Thr Pro Lys Asp Asn Glu Ile Ser Thr Phe
        515                 520                 525

His Asn Leu Gly Asn Val His Ser Pro Leu Lys His His His His His
    530                 535                 540

His
545
```

<210> SEQ ID NO 14
<211> LENGTH: 32
<212> TYPE: DNA
<213> ORGANISM: Artificial Sequence
<220> FEATURE:
<223> OTHER INFORMATION: Primer

<400> SEQUENCE: 14
ggatcctgcg catgaaaaag cctgaactca cc 32

<210> SEQ ID NO 15
<211> LENGTH: 29
<212> TYPE: DNA
<213> ORGANISM: Artificial Sequence
<220> FEATURE:
<223> OTHER INFORMATION: Primer

<400> SEQUENCE: 15
gcggccgcct attcctttgc cctcggacg 29

<210> SEQ ID NO 16
<211> LENGTH: 10939
<212> TYPE: DNA
<213> ORGANISM: Cricetulus griseus

<400> SEQUENCE: 16
gagctcaatt aaccctcact aaagggagtc gactcgatcc tttacagaaa acttgcaaac 60
cctcttggag tagaaaagta gtagtatctg acacaagtat cagcaaaatg caaacttctc 120
cccatcccca gaaaaccatt ataaaaaccc ccatatctta tgcccaactg tagtgatata 180
ttatttatga tttattaaaa cttgcttaag gattcagaaa gcaaagtcag ccttaagcta 240
tagagaccag gcagtcagtg gtggtacaca cctttaatcc caggactcag gattaagaag 300
tagacggacc tctgttagtt caagtctacc attacctaca caagagtgaa gagtaaccga 360
tctcatgcct ttgatcccag cagctgggat catgtgcatt caatcccagc attcgggagt 420
tatataagac aggagcaagg tctcagagct ggcattcatt ctccagccac attgaggata 480
ggaaaacatt gaagtgtcag gatgctgagg agaggcagca gtttgaggtt tggtagaacc 540
aggatcacct tttggtctga ggtagagtaa gaactgtggc tggctgcttt gcttttctga 600
tcttcagctt gaagcttgaa ctccaatatt tgtctctggg tctattatta tcatgttaca 660
cctaacttta aagctgattt acgcaagaca gttgtaggtg gacctttctt tcctgcccac 720
cagttcccaa ataactgaca cggagactca atattaatta taaatgattg gttaatagct 780
cagtcttgtt actggctaac tcttacattt taaattaact catttccatc cctttacttg 840
ctgccatgtg gttcatggct tgttcaagtc ctgcttcttc tgtctctggc tggtgatgcc 900
tctggttctg ccctttatcc cagaattctc ctagtctggc tctcctgccc agctataggc 960
cagtcagctg tttattaacc aatgagaata atacatattt atagtgtaca aagattgctc 1020
ctcaacaccc aattttttat gtgcaacctg agaatctgga ctcattgccc tcatgcttgc 1080
agaggcggca cccttaccca ctaagccacc tttctagccc tgttgctttt gtttttgag 1140 acaggttcca ctatgtagcc caggctggcc tcaaactgac cattctcctg cctaaacctc 1200
ccgaacactg gaattatagt caaggcctac ctgccctggc attttcacac ttttatttcc 1260
tggctgagtc cattgacttt acactcatca aggttgaacc agttggagtt taattacagt 1320
gccaatcgca ctgaatccca cataatcaaa caacttcaag gaagcaaaaa accagttttt 1380
cctgaagatc aatgtcagct tgcctgattc agaatagacc cccgaaaaaa ggcaaatgct 1440
tgataaccaa tttcttctta ttgttcaatc ccctgctgct gtgtgtaagc tcctgagaaa 1500
ggacagtaag gggacattca tgatcagaga aagagcccca actccccccc cagccccacc 1560
cccaccctgt ccacagtctg ttggtttggt ttccccctgg ctgacaccca gaaatcacaa 1620
cataatcacc taggtcactg taacaagttc ctttctggaa aatgctacaa atgatattgg 1680
taacatgagt aatgaataat gcctggagtc caactccctt gtgacccagc aatgttttcc 1740
gtgggtgctc ccttccccag ctgcaggcct gacatgtacc ttaaaaagcc tcccctggag 1800
gacagaattt tgtgggtact atagtgttct cacaaatact tcccctaata cccttactta 1860
gttaccataa ataacatgca gcccctggtg aggcacacag ggctccaatg tacagcttct 1920
cagacactgc aggaaccttc ctctcctaat gcagcactgg tctcttcagg ctggacagca 1980
ggaacccata ccactccaat cctagtgtgg agtagagctg tctacgaaaa ccagcagatc 2040
tatagctaaa tgtgtttcaa ttttatgctt tgacaaattg tactgacccc acccccaccc 2100 cttcccccctt gctgtgctgg gaattgaacc caggaccttg tgcatgccag gcaagtactc 2160

-continued

```
taacactgag ctatagcccc aatctttcat ccaagtctct atgtgtgccc acactcgctt   2220
tttattttga gacaaaaggt tcttattttg agataaggtc tcactatgtt gccttgactt   2280
tttttttttt tttttttga acttttgacc ttcctacctc agctgagact acaagtcttt    2340
taccatcagg cccggctgat ggtaaaataa cagtatttga aatagtttaa acacatcatc   2400
ttaatggtca accacacaat ttccgaaatg ttgctggctc agtctggggc aaacctgtcc   2460
gccccaacat tggtgctagg aagaaagcac agacaagtag ccctcccagc tcaggagtaa   2520
aagacctgga gggggtggcc cacttcggtc aagttcacgg gatggggagg ggtaccctcc   2580
tccagtagtg gtggtatttg gcagttcctc caccgacgcc ctctggaagc acctgcttgg   2640
acccgcaaag ccaggaatgc agcttcctca agggactcgc cagcgagggt aacaggacag   2700
aggcgtccca agagggctgg ggcggaaggg ggaagacagg gtcggcctta gatagggcaa   2760
agggccttct ggctgtgttc ccggggtaac cgccccacca cgcctggagc ccgacgtggc   2820
gagcgatggg gacagcgagc aggaagtcgt actggggagg gccgcgtagc agatgcagcc   2880
gagggcggcg ctgccaggta cacccgaggg caccgcgggg gtgagcgcca ggtccctgaa   2940
ccagccaggc ctccagagcc gagtccggcg gaccgacggt acgttctgga atgggaaggg   3000
atccgggaca ccgaattgct gcattgaggg gctcagaggt tctgatgtgg gagtccagaa   3060
agggttttat ctaccggagg tgatgtgact tccggcctct ggaagtgctg ttggagtctc   3120
tgggaccttg ggtcctctcg actaggtttg gaaggggtga aataggggta gggagaaagg   3180
agaggactgc agcaatgtct tcccgaacga cctgggttcg ggaggggtcg aaggacaagg   3240
ggctgttgtg gggggtcttc agacgcggag gggtggtatt ctattttctg ggaagatggt   3300
gtcgatgcac ttgaccaagt ctagtcgatc tgaagaggct aggggaacag acagtgagag   3360
aggatggtgg agggagtggc agaacccttc cagaaactgg gagaggctct agcacctgca   3420
acccccttccc tggcctccgg ggagtcccag aagagggcag gaccatggac acaggtgcat  3480
tcgtgccggc gcgctccggc ctggcgaagg tgcgcgctct tggaggccgc gggagggcca   3540
gacgcgcgcc cggagagctg gcccttttaag gctacccgga ggcgtgtcag gaaatgcgcc  3600
ctgagcccgc ccctcccgga acgcggcccg agacctggca agctgagacg gaactcggaa   3660
ctagcactcg gctcgcggcc tcggtgaggc cttgcgcccg ccatgcctct gtcattgccc   3720
ctcgggccgc ctccctgaac ctccgtgacc gccctgcagt cctccctccc cccttcgac    3780
tcggcgggcg cttccgggcg ctcccgcagc ccgccctcca cgtagcccac acctccctct   3840
cggcgctccg cttcccacgc ggtccccgac ctgttctttc ctcctccacc ctgcccttct   3900
gtccctctcc cttcctttct cccctcgact cgtccctatt aggcaacagc ccctgtggtc   3960
cagccggcca tggctgtcaa ggctcacacc cttagctagg ccccttctcc cttccctggg   4020
tcttgtctca tgaccccctg ccccgcccgg gagcgagcgc gatgtggagc agtgcctctg   4080
gcaagcagaa cttcacccaa gccatgtgac aattgaaggc tgtacccccca gaccctaaca  4140
tcttggagcc ctgtagacca gggagtgctt ctggccgtgg ggtgacctag ctcttctacc   4200
accatgaaca gggcccctct gaagcggtcc aggatcctgc gcatggcgct gactggaggc   4260
tccactgcct ctgaggaggc agatgaagac agcaggaaca agccgtttct gctgcgggcg   4320
ctgcagatcg cgctggtcgt ctctctctac tgggtcacct ccatctccat ggtattcctc   4380
aacaagtacc tgctggacag cccctccctg cagctggata ccccctatctt cgtcactttc  4440
taccaatgcc tggtgacctc tctgctgtgc aagggcctca gcactctggc cacctgctgc   4500
cctggcaccg ttgacttccc caccctgaac ctggacctta aggtggcccg cagcgtgctg   4560
```

-continued

```
ccactgtcgg tagtcttcat tggcatgata agtttcaata acctctgcct caagtacgta   4620
ggggtggcct tctacaacgt ggggcgctcg ctcaccaccg tgttcaatgt gcttctgtcc   4680
tacctgctgc tcaaacagac cacttccttc tatgccctgc tcacatgtgg catcatcatt   4740
ggtgagtggg gcccgggggc tgtgggagca ggatgggcat cgaactgaag ccctaaaggt   4800
caacactgta ggtaccttta cttactgtcc caggtccctt gcatcagcag ttacaggaag   4860
agccctgtag aaaacaaata acttccttat ggtcattcaa caagttaggg acccagccag   4920
ggtgaaaata atgttagcag caactacagc aaagatggct ctcgccactt gcatgattaa   4980
aatgtgccag gtactcagat ctaagcattg gatccacatt aactcaacta atccctatta   5040
caaggtaaaa tatatccgaa ttttacagag ggaaaaccaa ggcacagaga ggctaagtag   5100
cttgaccagg atcacacagc taataatcac tgacatagct gggatttaaa cataagcagt   5160
tacctccata gatcacacta tgaccaccat gccactgttc cttctcaaga gttccaggat   5220
cctgtctgtc cagttctctt taaagaggac aacacatctg acattgctac cttgaggtaa   5280
catttgaaat agtgggtaga catatgtttt aagttttatt cttacttttt atgtgtgtgt   5340
gtttgggggg ccaccacagt gtatgggtgg agataagggg acaacttaag aattggtcct   5400
ttctcccacc acatgggtgc tgaggtctga actcaggtca tcaggattgg cacaaatccc   5460
tttacccact gagccatttc actggtccaa tatatgtgtg cttttaagag gctttaacta   5520
ttttcccaga tgtgaatgtc ctgctgatca ttatcccctt ttacccggaa gccctctggg   5580
aggtgccatc cctgtggtcg tctgcataca aatggggaaa ctgcaactca gagaaacaag   5640
gctacttgcc agggccccac aagtaagata ggctgggatg ccatcccaga ctggccacac   5700
tccctggcct gtgcttcaag ccagtttact ttgttcctgc ccattggaag ttagcatgtt   5760
gcagtcaaac acaataacta caggccaaaa gtgcttttaa attaaagtca gatgaacttt   5820
taaacatcca gagctcctca actgcaggag ttacaacctg attctgcaac catctttgca   5880
gtgcccggta gtcatatgta gctagaggct cttggctagg acagcatgtg ttaggaaaca   5940
tctggccctg agatcattga attgagtgac tgctgggtga caaagaccaa ggcatccgtt   6000
ccctgagagt cctgggcaag cagcaatgtg accttcattt gtacctactc aggttcttta   6060
tctgtcctgt ttgacctact tagtctcctc tggtgtctca gaggcccagg ctgggtactc   6120
tggatgtcag gatcaggcca atgcgcacat ctgccctaga aatgtccccc tggttgagca   6180
gctcctgaat ccatcggtaa agggtctgga ccagggagga gtcagataaa aagctgacag   6240
cactggggga ctccatgggg aactcccacc tgcccccaca catccatcct aagagaactg   6300
gtattccttg tttcctcttt gtcctacaag gcaccctggg atcccacttc agtctcccag   6360
ccttgccagg gttagagggc atgagcctcc ttgtggggaa tttagatgca agaaggtaca   6420
gtcactagag aacctgagct cagatcccca aagtaaccag tacctgatag tgaggcagct   6480
gagaaccgca gcagcctgcc tgagtggctg aactctgcgg cctccggaac tggccccaac   6540
tgttgggtct cctcttcctt cctcctgtga gggagggccc atctctgata agtgctgtgg   6600
ggactctaga gtagggagga ggaggagcaa tctaagcagg ccttactgag aagtccttgc   6660
tggcatgtgg ctgcctgagg agtacagact gggaacaccc atttgaatga gtaaggtttt   6720
tcctgaaggc catggggagc cacggaggaa aatcatttta gttacaagac aaagagtaga   6780
ttggttaaca tgggagcaag gacatggccc caattttcat agatgaagga aattggaact   6840
cagagaggtt aagtaacttc tcccaaatag ctcagcttca aaatcacaga acagtcagag   6900
tctagatctc tctgatgcct gtgatggtcc tgccattcca tgttgctgat ccctgtggca   6960
```

-continued

```
tcagtaagcc tctaccttgt gggaatgcag gatctaaatg aagagaggaa gtgctggccc   7020
catgctgtgg tctggaaagc tatgcaggct ctttgagcag agagtgaccc acaagtgaat   7080
agagtcctat gagactcaaa gcaacatcca cccttaagca gctctaacca aatgctcaca   7140
ctgagggagc caaagccaag ttagagtcct gtgcttgccc aaggtcactt tgcctggccc   7200
tcctcctata gcacccgtgt tatcttatag ccctcattac agtgattaca attataatta   7260
gagaggtaac agggccacac tgtccttaca cattcccctg ctagattgta gctgggagag   7320
ggggagatgt aggtggctgg gggagtggga gggaagatgc agattttcat tctgggctct   7380
actccctcag ccatttttg gtgtgggagt tagactttgg atatgttgat gatgaggtaa   7440
gggccacaga acagtctgaa ctgtggtatc agaatcctgt ccctctccct ctctcctcat   7500
ccctcttcac cttgtcactc ctctgtctgc tacaggtggt ttctggctgg gtatagacca   7560
agagggagct gagggcaccc tgtccctcat aggcaccatc ttcggggtgc tggccagcct   7620
ctgcgtctcc ctcaatgcca tctataccaa gaaggtgctc ccagcagtgg acaacagcat   7680
ctggcgccta accttctata acaatgtcaa tgcctgtgtg ctcttcttgc ccctgatggt   7740
tctgctgggt gagctccgtg ccctccttga ctttgctcat ctgtacagtg cccacttctg   7800
gctcatgatg acgctgggtg gcctcttcgg ctttgccatt ggctatgtga caggactgca   7860
gatcaaattc accagtcccc tgacccacaa tgtatcaggc acagccaagg cctgtgcgca   7920
gacagtgctg gccgtgctct actatgaaga gactaagagc ttcctgtggt ggacaagcaa   7980
cctgatggtg ctgggtggct cctcagccta tacctgggtc aggggctggg agatgcagaa   8040
gacccaagag gaccccagct ccaaagaggg tgagaagagt gctattgggg tgtgagcttc   8100
ttcagggacc tgggactgaa cccaagtggg gcctacacag cactgaaggc ttcccatgga   8160
gctagccagt gtggccctga gcaatactgt ttacatcctc cttggaatat gatctaagag   8220
gagccagggt ctttcctggt aatgtcagaa agctgccaaa tctcctgtct gccccatctt   8280
gttttgggaa aaccctacca ggaatggcac ccctacctgc ctcctcctag agcctgtcta   8340
cctccatatc atctctgggg ttgggaccag ctgcagcctt aaggggctgg attgatgaag   8400
tgatgtcttc tacacaaggg agatgggttg tgatcccact aattgaaggg atttgggtga   8460
ccccacacct ctgggatcca gggcaggtag agtagtagct taggtgctat taacatcagg   8520
aacacctcag cctgcctttg aagggaagtg ggagcttggc caagggagga aatggccatt   8580
ctgccctctt cagtgtggat gagtatggca gacctgttca tggcagctgc accctggggt   8640
ggctgataag aaaacattca cctctgcatt tcatatttgc agctctagaa cgggggagag   8700
ccacacatct tttacgggtt aagtagggtg atgagctcct ccgcagtccc taaccccagc   8760
tttacctgcc tggcttccct tggcccagct acctagctgt actccctttc tgtactcttc   8820
tcttctccgt catggcctcc cccaacacct ccatctgcag gcaggaagtg gagtccactt   8880
gtaacctctg ttcccatgac agagcccttt gaatacctga acccctcatg acagtaagag   8940
acatttatgt tctctggggc tggggctgaa ggagcccact ggttctcact tagcctatct   9000
ggctcctgtc acaaaaaaaa aaaaagaaaa aaaaaaagca taaaccaagt tactaagaac   9060
agaagttggt ttataacgtt ctggggcagc aaagcccaga tgaagggacc catcgaccct   9120
ctctgtccat atcctcatgc tgcagaagta caggcaagct cctttaagcc tcatatagga   9180
acactagcct cactcatgag ggttttactc catgacctgt caacctcaaa gccttcaaca   9240
tgaggactcc aacgtaaatt tggggacaga agcactcaga ccatacccca gcaccacacc   9300
ctcctaacct cagggtagct gtcattctcc tagtctcctc tcttgggcct ttagaacccc   9360
```

```
catttccttg gggtaatgtc tgatgttttt gtccctgtca taaaaagatg gagagactgt   9420

gtccagcctt tgattcctac ttcctacaat cccaggttct aatgaagttt gtggggcctg   9480

atgccctgag ttgtatgtga tttaataata aaaaagcaag atacagcatg tgtgtggact   9540

gagtgagggc cacagggatc taaaagccaa gtgtgagggg acccagctac agcaggcagc   9600

atcctgagcc tggaatctct tcaggacaag aattctccat atacctacct actctgggga   9660

gtaggtggcc agagttcaag cttcccttag taccaactac cactggctgt gctcttactg   9720

aaggcagaca tggcactgag tgctgtccat ctgtcactca tctccacagc cattcctaat   9780

gtgtggggtg ggagccatca ccaaacccca ttttcagata aggacacagg ctcagagagg   9840

cttgtgtgga gaaaagtagc agcagaattc agagagctgg gtctcctgca gcaccttgga   9900

ctgccagcag ccacagtgct tgtcacacag cacatactca aaagaatgcc agccccctca   9960

gcctagagtg cctggccttt ctttcagatg aggaagaggg tcaaagctgt tagcttgccc  10020

accatatgac cacatacatg accaacagct tgagggaggg aggattactg tggctcccag  10080

cctgagaggt gggacaccca aatgtattag gtccttgaat cagggctgac cttgtgattc  10140

agtcactcct accagaatgc tggggaatgg ggatgccaaa ggcaaaggag gctttctaag  10200

gtgtggtgta agataggcat ttctgcttcc atgtacacct gtgagcagag taggaaggcc  10260

ctgtggagaa tatatcccac aaaccagtag ccccttcctgg cagtgggtga atactgccac  10320

cctatacccc tatgcaaggc cagtagaacc acccaaccca caacatctag agaaattaca  10380

ggtcatctta agcctctaaa ttgtggagaa actcgacatg cgcacgattc ctaacctgct  10440

agcctagggt gcggggtgga taatttaagg aaactggggt ttcttataga atcggaggct  10500

ccatgaagtc accctgacaa gaggtcagca atagccagca gcagtggcta ctcctaagcc  10560

tccagacaga gcaccctgtg aatgtacctt attctcacat ctgggtgtct ataggtgtga  10620

ctgggtcaga tgtcacccag gccattgcaa tgggccctta gccccatggg gtgttgggat  10680

agcagccaag cagctcccat gctgagatac tgcctgcagt agactgatgg ataagaaaac  10740

aaggcccaaa atgttttctt tccagacttg atctttcttt gttcaaaaat gctgtttccc  10800

cttaaacttg cccaaaccca ttgttttgca gttgaggaaa ataaggcata gaaagattaa  10860

aggaagtttc tgaggttaca gagcaaagta ctggcttcac ctgaaataga caggtgtgcc  10920

ctgatcctga tttgagctc                                                10939
```

<210> SEQ ID NO 17
<211> LENGTH: 33
<212> TYPE: DNA
<213> ORGANISM: Artificial Sequence
<220> FEATURE:
<223> OTHER INFORMATION: Primer

<400> SEQUENCE: 17

```
atgcatgcca ccatgaaaaa gcctgaactc acc                                   33
```

<210> SEQ ID NO 18
<211> LENGTH: 28
<212> TYPE: DNA
<213> ORGANISM: Artificial Sequence
<220> FEATURE:
<223> OTHER INFORMATION: Primer

<400> SEQUENCE: 18

```
ggatcccagg ctttacactt tatgcttc                                         28
```

<210> SEQ ID NO 19

-continued

<211> LENGTH: 25
<212> TYPE: DNA
<213> ORGANISM: Artificial Sequence
<220> FEATURE:
<223> OTHER INFORMATION: Primer

<400> SEQUENCE: 19
gctgtctgga gtactgtgca tctgc 25

<210> SEQ ID NO 20
<211> LENGTH: 27
<212> TYPE: DNA
<213> ORGANISM: Artificial Sequence
<220> FEATURE:
<223> OTHER INFORMATION: Primer

<400> SEQUENCE: 20
ggaatgcagc ttcctcaagg gactcgc 27

<210> SEQ ID NO 21
<211> LENGTH: 27
<212> TYPE: DNA
<213> ORGANISM: Artificial Sequence
<220> FEATURE:
<223> OTHER INFORMATION: Primer

<400> SEQUENCE: 21
tgcatcaggt cggagacgct gtcgaac 27

<210> SEQ ID NO 22
<211> LENGTH: 27
<212> TYPE: DNA
<213> ORGANISM: Artificial Sequence
<220> FEATURE:
<223> OTHER INFORMATION: Primer

<400> SEQUENCE: 22
gcactcgtcc gagggcaaag gaatagc 27

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
tgtgctggga attgaaccca ggac 24

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
ctacttgtct gtgctttctt cc 22

<210> SEQ ID NO 25
<211> LENGTH: 27
<212> TYPE: DNA
<213> ORGANISM: Artificial Sequence
<220> FEATURE:
<223> OTHER INFORMATION: Primer

<400> SEQUENCE: 25
ctcgactcgt ccctattagg caacagc 27

<210> SEQ ID NO 26
<211> LENGTH: 27
<212> TYPE: DNA
<213> ORGANISM: Artificial Sequence
<220> FEATURE:
<223> OTHER INFORMATION: Primer

<400> SEQUENCE: 26
tcagaggcag tggagcctcc agtcagc 27

<210> SEQ ID NO 27
<211> LENGTH: 115
<212> TYPE: PRT
<213> ORGANISM: Artificial Sequence
<220> FEATURE:
<223> OTHER INFORMATION: Modified antibody

<400> SEQUENCE: 27

```
Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Glu Gly Leu Glu Trp Ile
        35                  40                  45

Gly Ala Ile Asp Pro Lys Thr Gly Asp Thr Ala Tyr Ser Glu Ser Phe
    50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115
```

<210> SEQ ID NO 28
<211> LENGTH: 112
<212> TYPE: PRT
<213> ORGANISM: Artificial Sequence
<220> FEATURE:
<223> OTHER INFORMATION: Modified antibody

<400> SEQUENCE: 28

```
Asp Ile Val Met Thr Gln Ser Pro Leu Ser Leu Pro Val Thr Pro Gly
1               5                   10                  15

Glu Pro Ala Ser Ile Ser Cys Gln Ala Ser Glu Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110
```

<210> SEQ ID NO 29
<211> LENGTH: 112
<212> TYPE: PRT
<213> ORGANISM: Artificial Sequence
<220> FEATURE:
<223> OTHER INFORMATION: Modified antibody

<400> SEQUENCE: 29

```
Asp Ile Val Met Thr Gln Ser Pro Leu Ser Leu Pro Val Thr Pro Gly
1               5                   10                  15

Glu Pro Ala Ser Ile Ser Cys Gln Ala Ser Glu Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Val Glu Ile Glu
            100                 105                 110
```

<210> SEQ ID NO 30
<211> LENGTH: 327
<212> TYPE: PRT
<213> ORGANISM: homo sapiens

<400> SEQUENCE: 30

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220
```

```
Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 31
<211> LENGTH: 330
<212> TYPE: PRT
<213> ORGANISM: homo sapiens

<400> SEQUENCE: 31

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

-continued

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 32
<211> LENGTH: 328
<212> TYPE: PRT
<213> ORGANISM: Artificial Sequence
<220> FEATURE:
<223> OTHER INFORMATION: Modified antibody

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr 305 310 315 320

Gln Lys Ser Leu Ser Leu Ser Pro
325

<210> SEQ ID NO 33
<211> LENGTH: 328
<212> TYPE: PRT
<213> ORGANISM: Artificial Sequence
<220> FEATURE:
<223> OTHER INFORMATION: Modified antibody

<400> SEQUENCE: 33

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser Gln Glu Asp Pro Glu Val Gln Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Gln Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Glu Gly Asn
290 295 300

Val Phe Ser Cys Ser Val Met His Glu Ala Leu His Asn His Tyr Thr
305 310 315 320

Gln Lys Ser Leu Ser Leu Ser Pro
325

<210> SEQ ID NO 34

<211> LENGTH: 443
<212> TYPE: PRT
<213> ORGANISM: Artificial Sequence
<220> FEATURE:
<223> OTHER INFORMATION: Modified antibody

<400> SEQUENCE: 34

```
Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Glu Gly Leu Glu Trp Ile
        35                  40                  45

Gly Ala Ile Asp Pro Lys Thr Gly Asp Thr Ala Tyr Ser Glu Ser Phe
    50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380
```

Pro Glu Asn Asn Tyr Lys Thr Thr Pro Pro Val Leu Asp Ser Asp Gly
385 390 395 400

Ser Phe Phe Leu Tyr Ser Lys Leu Thr Val Asp Lys Ser Arg Trp Gln
405 410 415

Glu Gly Asn Val Phe Ser Cys Ser Val Met His Glu Ala Leu His Asn
420 425 430

His Tyr Thr Gln Lys Ser Leu Ser Leu Ser Pro
435 440

<210> SEQ ID NO 35
<211> LENGTH: 443
<212> TYPE: PRT
<213> ORGANISM: Artificial Sequence
<220> FEATURE:
<223> OTHER INFORMATION: Modified antibody

<400> SEQUENCE: 35

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Glu Met His Trp Val Arg Gln Ala Pro Gly Gln Gly Leu Glu Trp Met
35 40 45

Gly Ala Leu Asp Pro Lys Thr Gly Asp Thr Ala Tyr Ser Gln Lys Phe
50 55 60

Lys Gly Arg Val Thr Leu Thr Ala Asp Lys Ser Thr Ser Thr Ala Tyr
65 70 75 80

Met Glu Leu Ser Ser Leu Thr Ser Glu Asp Thr Ala Val Tyr Tyr Cys
85 90 95

Thr Arg Phe Tyr Ser Tyr Thr Tyr Trp Gly Gln Gly Thr Leu Val Thr
100 105 110

Val Ser Ser Ala Ser Thr Lys Gly Pro Ser Val Phe Pro Leu Ala Pro
115 120 125

Ser Ser Lys Ser Thr Ser Gly Gly Thr Ala Ala Leu Gly Cys Leu Val
130 135 140

Lys Asp Tyr Phe Pro Glu Pro Val Thr Val Ser Trp Asn Ser Gly Ala
145 150 155 160

Leu Thr Ser Gly Val His Thr Phe Pro Ala Val Leu Gln Ser Ser Gly
165 170 175

Leu Tyr Ser Leu Ser Ser Val Val Thr Val Pro Ser Ser Ser Leu Gly
180 185 190

Thr Gln Thr Tyr Ile Cys Asn Val Asn His Lys Pro Ser Asn Thr Lys
195 200 205

Val Asp Lys Lys Val Glu Pro Lys Ser Cys Asp Lys Thr His Thr Cys
210 215 220

Pro Pro Cys Pro Ala Pro Glu Leu Leu Gly Gly Pro Ser Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser Gln Glu Asp Pro Glu Val Gln
260 265 270

Phe Asn Trp Tyr Val Asp Gly Val Glu Val His Asn Ala Lys Thr Lys
275 280 285

Pro Arg Glu Glu Gln Tyr Asn Ser Thr Tyr Arg Val Val Ser Val Leu
290 295 300

Thr Val Leu His Gln Asp Trp Leu Asn Gly Lys Glu Tyr Lys Cys Lys

-continued

```
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Pro
        435                 440
```